United States Patent
Meadows et al.

(10) Patent No.: US 7,769,462 B2
(45) Date of Patent: Aug. 3, 2010

(54) RECHARGEABLE SPINAL CORD STIMULATION SYSTEM

(75) Inventors: Paul M. Meadows, Glendale, CA (US); Carla Mann Woods, Los Angeles, CA (US); David K. Peterson, Saugus, CA (US); Joey Chen, Arcadia, CA (US); David H. Payne, Llano, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 803 days.

(21) Appl. No.: 11/625,283

(22) Filed: Jan. 20, 2007

(65) Prior Publication Data

US 2007/0276450 A1 Nov. 29, 2007

Related U.S. Application Data

(63) Continuation of application No. 11/009,508, filed on Dec. 10, 2004, now Pat. No. 7,496,404, which is a continuation of application No. 10/307,098, filed on Nov. 27, 2002, now Pat. No. 6,895,280, which is a continuation of application No. 09/626,010, filed on Jul. 26, 2000, now Pat. No. 6,516,227.

(60) Provisional application No. 60/145,829, filed on Jul. 27, 1999.

(51) Int. Cl.
*A61N 1/00* (2006.01)
(52) U.S. Cl. ..................................................... 607/46
(58) Field of Classification Search ................... 607/47, 607/46, 74; 600/547
See application file for complete search history.

(56) References Cited

U.S. PATENT DOCUMENTS

| | | | |
|---|---|---|---|
| 3,646,940 A | 3/1972 | Timm et al. |
| 3,724,467 A | 4/1973 | Avery et al. |
| 3,822,708 A | 7/1974 | Zilber |
| 4,019,519 A | 4/1977 | Geerling |
| 4,096,866 A | 6/1978 | Fischell |
| 4,197,850 A | 4/1980 | Schulman et al. |
| 4,223,679 A | 9/1980 | Schulman et al. |
| 4,231,027 A | 10/1980 | Mann et al. |

(Continued)

FOREIGN PATENT DOCUMENTS

EP 0 047 822 A1 3/1982

(Continued)

*Primary Examiner*—George Manuel
(74) *Attorney, Agent, or Firm*—Vista IP Law Group LLP

(57) ABSTRACT

A spinal cord stimulation (SCS) system includes multiple electrodes, multiple, independently programmable, stimulation channels within an implantable pulse generator (IPG) which channels can provide concurrent, but unique stimulation fields, permitting virtual electrodes to be realized. The SCS system includes a replenishable power source (e.g., rechargeable battery), that may be recharged using transcutaneous power transmissions between antenna coil pairs. An external charger unit, having its own rechargeable battery can be used to charge the IPG replenishable power source. A real-time clock can provide an auto-run schedule for daily stimulation. An included bi-directional telemetry link in the system informs the patient or clinician the status of the system, including the state of charge of the IPG battery. Other processing circuitry in the IPG allows electrode impedance measurements to be made. Further circuitry in the external battery charger can provide alignment detection for the coil pairs.

14 Claims, 32 Drawing Sheets

U.S. PATENT DOCUMENTS

| | | | |
|---|---|---|---|
| 4,232,679 A | 11/1980 | Schulman | |
| 4,338,945 A | 7/1982 | Kosugi et al. | |
| 4,379,462 A | 4/1983 | Borkan | |
| 4,390,023 A | 6/1983 | Rise | |
| 4,459,989 A | 7/1984 | Borkan | |
| 5,121,754 A | 6/1992 | Mullett | |
| 5,179,950 A | 1/1993 | Stanislaw | |
| 5,314,457 A | 5/1994 | Jeutter et al. | |
| 5,417,719 A | 5/1995 | Hull et al. | |
| 5,501,703 A | 3/1996 | Holsheimer et al. | |
| 5,522,865 A | 6/1996 | Schulman et al. | |
| 5,559,828 A | 9/1996 | Armstrong et al. | |
| 5,571,148 A | 11/1996 | Loeb et al. | |
| 5,643,330 A | 7/1997 | Holsheimer et al. | |
| 5,733,313 A | 3/1998 | Barreras, Sr. et al. | |
| 5,735,887 A | 4/1998 | Barreras, Sr. et al. | |
| 5,769,877 A | 6/1998 | Barreras, Sr. | |
| 5,807,397 A | 9/1998 | Barreras | |
| 5,814,092 A | 9/1998 | King | |
| 5,891,180 A | 4/1999 | Greeninger et al. | |
| 5,925,070 A | 7/1999 | King et al. | |
| 5,938,690 A | 8/1999 | Law et al. | |
| 5,941,906 A | 8/1999 | Barreras, Sr. et al. | |
| 6,052,624 A | 4/2000 | Mann | |
| 6,185,452 B1 | 2/2001 | Schulman et al. | |
| 6,198,969 B1 | 3/2001 | Kuzma | |
| 6,205,359 B1 | 3/2001 | Boveja | |
| 6,205,361 B1 | 3/2001 | Kuzma et al. | |
| 6,317,628 B1 * | 11/2001 | Linder et al. | 600/547 |
| 6,393,325 B1 | 5/2002 | Mann et al. | |
| 6,516,227 B1 | 2/2003 | Meadows et al. | |
| 6,553,263 B1 | 4/2003 | Meadows et al. | |
| 6,577,900 B1 | 6/2003 | Silvian | |
| 6,735,474 B1 | 5/2004 | Loeb et al. | |
| 2004/0098068 A1 | 5/2004 | Carbunaru et al. | |

FOREIGN PATENT DOCUMENTS

| | | |
|---|---|---|
| WO | WO 99/42173 | 8/1999 |
| WO | WO 00/00251 | 1/2000 |
| WO | WO 02/09808 A1 | 2/2002 |

* cited by examiner

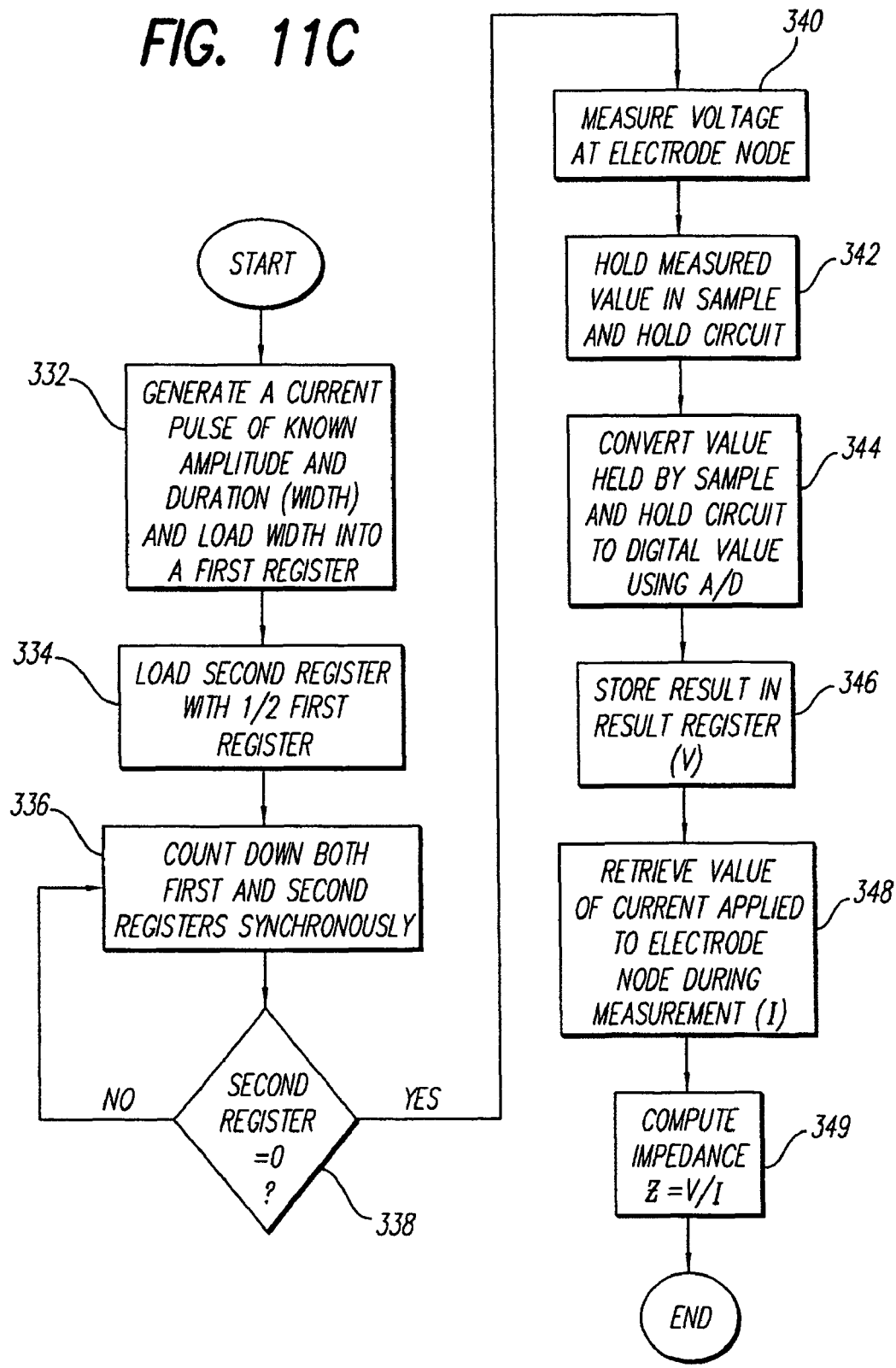

RECHARGEABLE SPINAL CORD STIMULATION SYSTEM

This application is a continuation of U.S. application Ser. No. 11/009,508, filed Dec. 10, 2004, now U.S. Pat. No. 7,496, 404 which is a continuation of, and claims the benefit of priority to U.S. application Ser. No. 10/307,098, filed Nov. 27, 2002, issued as U.S. Pat. No. 6,895,280, which is a continuation of, and claims the benefit of priority to U.S. application Ser. No. 09/626,010, filed Jul. 26, 2000, issued as U.S. Pat. No. 6,516,227, which claims the benefit of U.S. Provisional Application Ser. No. 60/145,829, filed Jul. 27, 1999, the disclosure of which is hereby incorporated by reference.

The present invention relates to a spinal cord stimulation system for stimulating nerves in the spinal cord.

BACKGROUND OF THE INVENTION

The present invention relates to a Spinal Cord Stimulation System. A spinal cord stimulation system is a programmable implantable pulse generating system used to treat chronic pain by providing electrical stimulation pulses from an electrode array placed epidurally near a patient's spine. The present invention emphasizes the following specific features included within a spinal cord stimulation system: (1) a recharging system, (2) a system for mapping current fields, (3) optional pulse ramping control, and (4) electrode impedance measurements.

Spinal cord stimulation (SCS) is a well accepted clinical method for reducing pain in certain populations of patients. SCS systems typically include an implanted pulse generator, lead wires, and electrodes connected to the lead wires. The pulse generator generates electrical pulses that are delivered to the dorsal column fibers within the spinal cord through the electrodes which are implanted along the dura of the spinal cord. In a typical situation, the attached lead wires exit the spinal cord and are tunneled around the torso of the patient to a sub-cutaneous pocket where the pulse generator is implanted.

Spinal cord and other stimulation systems are known in the art. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neuro-stimulation of the spinal cord. A relatively thin and flexible strip of physiologically inert plastic is provided with a plurality of electrodes formed thereon. The electrodes are connected by leads to an RF receiver, which is also implanted, and which is controlled by an external controller. The implanted RF receiver has no power storage means, and must be coupled to the external controller in order for neuro-stimulation to occur.

In U.S. Pat. No. 3,822,708, another type of electrical spinal cord stimulating device is shown. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of from 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; 5,121,754; 5,417,719 and 5,501,703.

The dominant SCS products that are presently commercially available attempt to respond to three basic requirements for such systems: (1) providing multiple stimulation channels to address variable stimulation parameter requirements and multiple sites of electrical stimulation signal delivery; (2) allowing modest to high stimulation currents for those patients who need it; and (3) incorporating an internal power source with sufficient energy storage capacity to provide years of reliable service to the patient.

Unfortunately, not all of the above-described features are available in any one device. For example, one well-known device has a limited battery life at only modest current outputs, and has only a single voltage source, and hence only a single stimulation channel, which must be multiplexed in a fixed pattern to up to four electrode contacts. Another well-known device offers higher currents that can be delivered to the patient, but does not have a battery, and thus requires the patient to wear an external power source and controller. Even then, such device still has only one voltage source, and hence only a single stimulation channel, for delivery of the current stimulus to multiple electrodes through a multiplexer. Yet a third known device provides multiple channels of modest current capability, but does not have an internal power source, and thus also forces the patient to wear an external power source and controller.

It is thus seen that each of the systems, or components, disclosed or described above suffers from one or more shortcomings, e.g., no internal power storage capability, a short operating life, none or limited programming features, large physical size, the need to always wear an external power source and controller, the need to use difficult or unwieldy surgical techniques and/or tools, unreliable connections, and the like. What is clearly needed, therefore, is a spinal cord stimulation (SCS) system that is superior to existing systems by providing longer life, easier programming and more stimulating features in a smaller package without compromising reliability. Moreover, the surgical tools and interconnections used with such SCS system need to be easier and faster to manipulate. Further, the stimulating features available with the system need to be programmable using programming systems which are easy to understand and use, and which introduce novel programming methods that better address the patient's needs.

SUMMARY OF THE INVENTION

In accordance with a first aspect of the present inventions, an implantable stimulator device is provided. The implantable stimulator device comprises a plurality of electrode nodes implantable adjacent to tissue to be stimulated. The implantable stimulator device further comprises programmable current source circuitry configured for sourcing a first one or more output currents respectively to a first one or more of the plurality of electrode nodes, and programmable current sink circuitry configured for sinking a second one or more output currents respectively from a second one or more of the plurality of electrode nodes. In one embodiment, the output currents are pulsed. In one embodiment, the implantable stimulator device comprises one or more stimulation electrode leads coupled to the electrode nodes. In another embodiment, the implantable stimulator device comprises a case coupled to one of the electrode nodes.

The implantable stimulator device further comprises control circuitry configured for programming the current source circuitry and the current sink circuitry, such that the a total sum of the first one or more output currents equals a total sum of the second one or more output currents in each of one or more channels. In one embodiment, the control circuitry comprises a microcontroller. In another embodiment, the control circuitry is configured for storing stimulation parameters with which the control circuitry is configured for programming the current source circuitry and the current sink circuitry. The stimulation parameters may be telemetrically programmed within the control circuitry.

In one embodiment, the current source circuitry comprises a plurality of adjustable positive current sources (e.g., PDACs), and the current sink circuitry comprises a plurality of adjustable negative current sources (e.g., NDACs). One of the positive current sources and one of the negative current sources may be coupled to one of the electrodes nodes via a common node. In this embodiment, the implantable stimulator device may comprise a programmable switch matrix, wherein the control circuitry is configured for programming the switch matrix to selectively couple one or more of the positive current sources respectively to the first one or more of the electrode nodes, and for programming the switch matrix to selectively couple one or more of the negative current sources respectively to the second one or more of the electrode nodes. Alternatively, the positive current sources may be respectively coupled to the plurality of electrode nodes in a dedicated manner, and the negative current sources may be respectively coupled to the plurality of electrode nodes in a dedicated manner.

In accordance with a second aspect of the present inventions, a method of treating a patient is provided. The method comprises implanting the previously described implantable stimulator device into a patient, and respectively coupling a plurality of electrodes to the electrode nodes. One method comprises stimulating neural tissue (e.g., spinal cord tissue) of the patient with the first one or more output currents.

BRIEF DESCRIPTION OF THE DRAWINGS

The above and other aspects, features and advantages of the present invention will be more apparent from the following more particular description thereof, presented in conjunction with the following drawings wherein:

FIG. 11C is a flow diagram that depicts an alternate technique that may be used by the invention to make electrode impedance measurements Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention.

The scope of the invention should be determined with reference to the claims.

Figure 1:
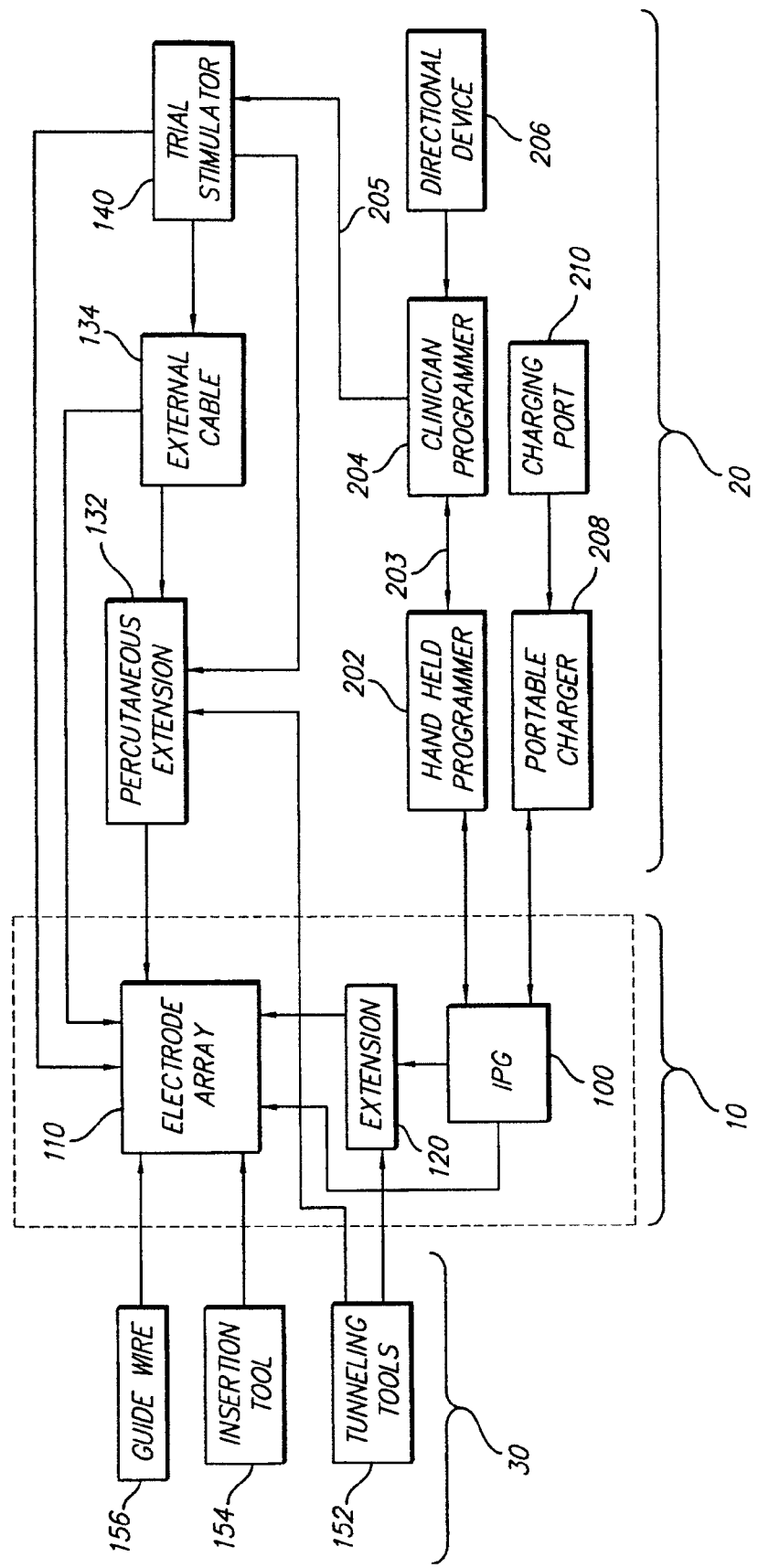
FIG. 1 is a block diagram that identifies the various implantable, external, and surgical components of the invention.

Turning first to FIG. 1, there is shown a block diagram that illustrates the various components of a spinal cord stimulation (SCS) system. These components may be subdivided into three broad categories: (1) implantable components 10, (2) external components 20, and (3) surgical components 30. As seen in FIG. 1, the implantable components 10 include an implantable pulse generator (IPG) 100, an electrode array 110, and (as needed) an extension 120. The extension 120 is used to electrically connect the electrode array 110 to the IPG 100. In a preferred embodiment, the IPG 100, described more fully below in connection with FIGS. 4A, 4B and 4C, comprises a rechargeable, multichannel, sixteen-contact, telemetry-controlled, pulse generator housed in a rounded titanium case. A novel tool-less connector that forms an integral part of the IPG 100 allows the electrode array 110 or extension 120 to be detachably secured, i.e., electrically connected, to the IPG 100. This connector may be of the type described in U.S. patent application Ser. No. 09/239,926, filed Jan. 28, 1999, now U.S. Pat. No. 6,198,969 or any other suitable design.

The IPG 100 contains stimulating electrical circuitry ("stimulating electronics"), a power source, e.g., a rechargeable battery, and a telemetry system. Typically, the IPG 100 is placed in a surgically-made pocket either in the abdomen, or just at the top of the buttocks. It may, of course, also be implanted in other locations of the patient's body. It is noted that while the preferred embodiment of the IPG 100 includes a rechargeable battery as its power source, and while such a rechargeable power source is described herein, any power source may be used with the IPG, including non-rechargeable power sources, e.g., an implantable battery of the type commonly used in implantable pacemakers.

Once implanted, the IPG 100 is connected to a lead system. The lead system comprises the lead extension 120, if needed, and the electrode array 110. The lead extension 120, for example, may be tunneled up to the spinal column. Once implanted, the electrode array 110 and lead extension 120 are intended to be permanent. In contrast, the IPG 100 may be replaced when its power source fails or is no longer rechargeable.

Figure 2A:
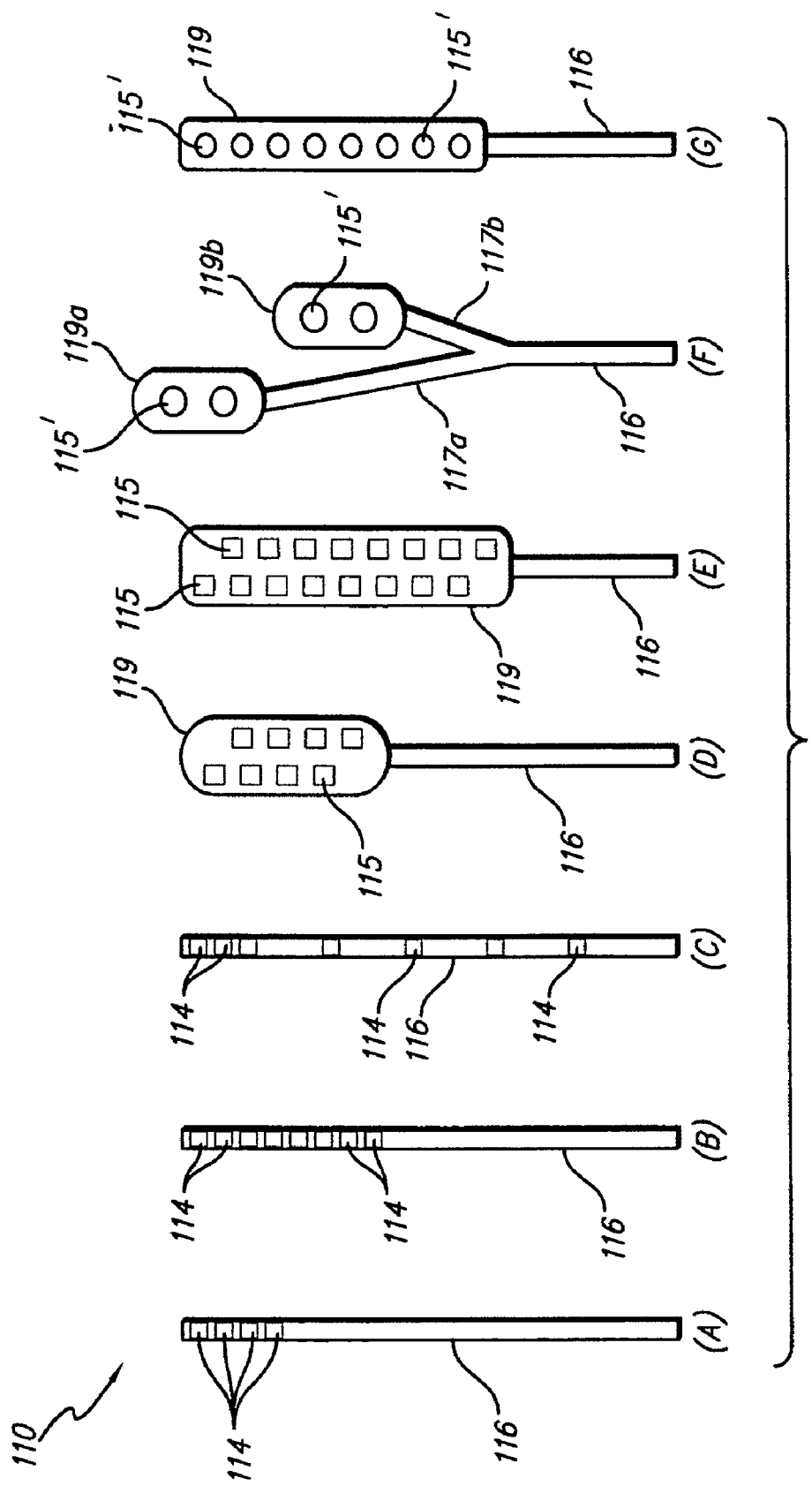
FIG. 2A illustrates examples of various types of electrode arrays that may be used with the present invention.

Advantageously, the IPG 100 provides electrical stimulation through a multiplicity of electrodes, e.g., sixteen electrodes, included within the electrode array 110. Different types of electrode arrays 110 that may be used with the invention are depicted in FIG. 2A. A common type of electrode array 110, for example, is the "in-line" lead, as shown at (A), (B), and (C) in FIG. 2A. An in-line lead includes individual electrode contacts 114 spread longitudinally along a small diameter flexible cable or carrier 116. The flexible cable or carrier 116 has respective small wires embedded (or otherwise carried therein) for electrically contacting each of the individual electrode contacts. The advantage of an in-line lead relates to its ease of implantation, i.e., it can be inserted into the spinal canal through a small locally-anesthetized incision while the patient is kept awake. When the patient is awake, he or she can provide valuable feedback as to the effectiveness of stimulation applied to a given electrode contact or contacts 114 for a given positioning of the array 110. One of the disadvantages of the in-line lead is that it is prone to migrating in the epidural space, either over time or as a result of a sudden flexion movement. Such migration can disadvantageously change the location and nature of the paresthesia and the required stimulation level. Either or both of the these conditions may require reprogramming of the IPG 100 and/or surgical correction (repositioning) of the electrode array 110. Note, as used herein, the term "paresthesia" refers to that area or volume of the patient's tissue that is affected by the electrical stimuli applied through the electrode array. The patient may typically describe or characterize the paresthesia as an area where a tingling sensation is felt.

To overcome the migration problems associated with an in-line electrode, the present invention provides a lead anchor (LA) and/or suture sleeve (SS) that may be used after insertion of the electrode array into the spinal canal in order to secure and maintain the position of the electrode and prevent is dislodgement due to axial loads that are placed upon the lead. Any suitable lead anchor and/or suture sleeve may be used for this purpose. A preferred type of lead anchor that may be used for this purpose is described in U.S. Patent Application Ser. No. 60/187,674, filed Mar. 8, 2000, incorporated herein by reference.

To further overcome the migration problems associated with an in-line electrode, a different type of electrode array 110 may be used, known as a paddle lead. Various types of paddle leads are illustrated at (D), (E), (F) and (G) of FIG. 2A. In general, each type of paddle lead is shaped with a wide platform 119 on which a variety of electrode contact configurations or arrays are situated. For example, the paddle lead shown at (D) in FIG. 2A has two columns of four rectangular-shaped electrode contacts 115 carried on a wide platform 119, with the electrode contacts in one column being offset from the electrode contacts in the other column. (Here, the term "offset" refers to the vertical position of the electrode contacts, as the leads are oriented in FIG. 2A.) The flexible cable or carrier 116 carries wires from each electrode contact to a proximal end of the paddle lead (not shown), where such wires may be connected to the IPG 100 (or to a lead extension 119, which in turn connects to the IPG 100). The paddle lead shown at (E) in FIG. 2A similarly has two columns of eight electrode contacts 115 in each row, with the electrode contacts in one column being offset from the electrode contacts in the other column, and with each electrode contact being connected to one or more wires carried in the flexible cable or carrier 116. It should be noted that two eight-contact in-line electrodes, placed side by side, may achieve the same overall array configuration as does the paddle electrode shown at (E) in FIG. 2A.

Still referring to FIG. 2A, other types of paddle leads are illustrated. As seen at (F) in FIG. 2A, one type of paddle lead has its carrier or cable 116 branch into two separate branches 117a and 117b, with a wide platform 119a and 119b being located at a distal end of each branch. Within each wide platform 119a and 119b an array of at least two circular-shaped electrode contacts 115' is situated. As seen in (G) in FIG. 2A, another type of paddle lead has a wide platform 119 at its distal end on which a single column of circular-shaped electrode contacts 115' is situated.

Still other types of leads may be used with the IPG 100 (FIG. 1) in addition to the representative leads shown in FIG. 2A. For example, the deployable electrode array disclosed in U.S. patent application Ser. No. 09/239,927, filed Jan. 28, 1999, now U.S. Pat. No. 6,205,361, represents a type of lead and electrode array that may be used with the invention.

Whichever type of lead and electrode array is used, an important feature of the SCS system of the present invention is the ability to support more than one lead with two or more channels. Here, a "channel" is defined as a specified electrode, or group of electrodes, that receive a specified pattern or sequence of stimulus pulses. Thus, where more than one "channel" is available, each channel may be programmed to provide its own specified pattern or sequence of stimulus pulses to its defined electrode or group of electrodes. In operation, all of the stimulus patterns applied through all of the channels of such multi-channel system thus combine to provide an overall stimulation pattern that is applied to the tissue exposed to the individual electrodes of the electrode array(s).

There are many instances when it is advantageous to have multiple channels. For example, left and right sides, or upper and lower extremities, may require different stimulus parameter settings. Low back pain typically requires a different stimulation site and stimulation parameters than any of the extremities. Moreover, many patients exhibit conditions better suited to horizontal stimulation paths, while other patients may have conditions better suited to vertical stimulation paths. Therefore, having multiple channels that may be connected to multiple electrodes, positioned within one or more electrode arrays, so as to cover more tissue/nerve area, greatly facilitates providing the type of stimulation pattern and stimulation parameters needed to treat a particular patient.

One type of preferred electrode configuration uses a multiple lead system, e.g., two or four leads, with the leads placed side by side, or at different vertical locations. The individual electrodes on each vertical lead of such multiple lead system effectively create a desired electrode array that covers a large, or relatively large, tissue area. The respective electrodes of each vertical lead may be aligned horizontally, offset horizontally, or randomly or systematically arranged in some other pattern As seen best in FIG. 2B, and as also illustrated in FIG. 1, the electrode array 110 and its associated lead system typically interface with the implantable pulse generator (IPG) 100 via a lead extension system 120. As needed, e.g., for testing and/or fitting purposes, the electrode array 110 may also interface with an external trial stimulator (ETS) 140 through one or more percutaneous lead extensions 132, connected to the trial stimulator 140 through an external cable 134. In this manner, the individual electrodes included within the electrode array 110 may receive an electrical stimulus from either the trial stimulator 140 or the IPG 100.

As suggested in the block diagram of FIG. 1, the lead extension(s) 120, as well as the percutaneous extension(s) 132 are inserted through the patient's tissue through the use of appropriate surgical tools (ST) 30, and in particular through the use of tunneling tools 152, as are known in the art, or as are especially developed for purposes of spinal cord stimulation systems. In a similar manner, the electrode array 110 is implanted in its desired position, e.g., adjacent the spinal column of the patient, through the use of an insertion needle 154 and a guide wire 156. The insertion needle, for example, may be a 15 gauge Touhy needle. Additionally, as required, a lead blank may be used to aid in the insertion process. A lead blank is a somewhat flexible wire that approximates the lead diameter of the lead that is to eventually be implanted. The clinician uses the lead blank to clear the path through the insertion needle and into the epidural space before inserting the epidural electrode array. Use of the lead blank prevents damage to the electrode array when tissue is obstructing its insertion path.

One manner of using surgical tools 30 during an implant operation is described in the referenced deployable electrode patent application Ser. No. 09/239,927, filed Jan. 28, 1999, now U.S. Pat. No. 6,205,361, previously referenced.

Another manner of using surgical tools 30 (FIG. 1) during an implant operation of an in-line electrode array may be summarized as follows: A fifteen gauge hollow needle is used to create an opening in the spinal canal to insert the in-line array, e.g., an in-line array of the type shown in FIG. 2A (A), (B), or (C). The hollow needle includes a removable stylet (solid core) for use during the needle insertion, as explained above. After the needle has been situated, the stylet is removed to create a hollow opening. A 3-5 ml syringe is inserted in the needle to inject saline (3-5 cc) to ensure the needle tip has entered the epidural space. The in-line electrode array is then passed through the needle into the epidural space. The size of the needle must be capable of entering the epidural space through small vertebral openings at less than a forty-five degree angle to the spine. After the electrode array is inserted, the needle must be pulled out. Hence, if the connector at the end of the lead is larger than the fifteen gauge needle tube, a split needle, or some other mechanism, must be used to allow removal of the needle over the over-sized connector.

One type of surgical tool that may be used to help implant an electrode array, and lead extension, if needed, for use with the present invention is described in U.S. Patent Application Ser. No. 60/166,560, filed Nov. 19, 1999, entitled "Integrated Subcutaneous Tunneling and Carrying Tool", incorporated herein by reference. Another type of surgical tool that may be used with the invention is described in U.S. Patent Application Ser. No. 60/182,392, filed Feb. 14, 2000, entitled "Versatile Implantable Lead System with Pull-Through Connector and Retainer", also incorporated herein by reference.

Once the electrode array 110 has been located in the spinal canal and the insertion needle is removed, an anchor is placed around the lead at the exit site. The anchor is then sutured in place to prevent movement of the electrode array and its lead. Advantageously, such suturing is performed so as not to damage the delicate wires that are carried within the lead body 116 (FIG. 2A). The anchor is slid over the lead body, much like a collar, or is placed over the lead body through other simple means. It is positioned along the length of the lead body at a desired position and then tightened around the lead body using a tightening method other than suturing. In a preferred embodiment, the lead anchor is relatively soft and pliable, is about 5 to 10 mm in length, and has easy-to-use suturing holes, or other means, to allow it to be sutured in its desired location. Such a lead anchor is described in U.S. Patent Application Ser. No. 60/187,674, filed Mar. 8, 2000, previously referenced.

When one or more lead extensions 120 are employed, a suitable multiple in-line contact connector may be used to electrically connect the electrode array 110 with the lead extension 120. One type of lead connector that may be used for this purpose is shown in U.S. Patent Application Ser. No. 60/202,259, filed May 5, 2000, entitled "Multiple In-Line Contact Connector", incorporated herein by reference.

Figure 3A:
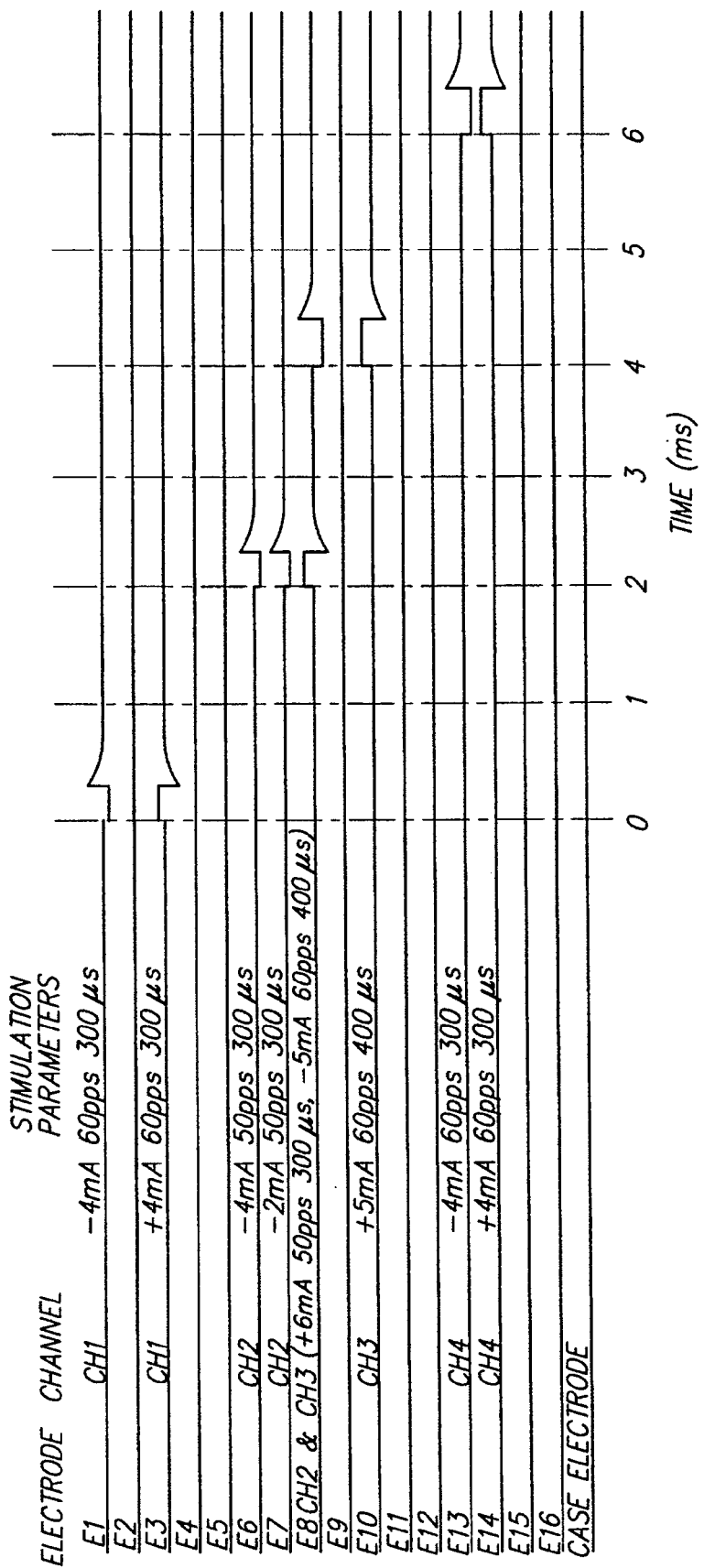
FIG. 3A is a timing waveform diagram that depicts representative current waveforms that may be applied to various ones of the electrode contacts of the electrode arrays through one or more stimulus channels.

The operation of multiple channels used to provide a stimulus pattern through multiple electrodes is illustrated in FIG. 3A. FIG. 3A assumes the use of an electrode array 110 having sixteen electrodes connected to the implantable pulse generator (IPG) 100. In addition to these sixteen electrodes, which are numbered E1 through E16, a case electrode (or return electrode) is also available. In FIG. 3A, the horizontal axis is time, divided into increments of 1 millisecond (ms), while the vertical axis represents the amplitude of a current pulse, if any, applied to one of the sixteen electrodes. Thus, for example, at time t=0 ms, FIG. 3A illustrates that a current pulse of 4 mA (milliamps) appears on channel 1 at electrode E1 and E3. FIG. 3A further shows that this current pulse is negative (−4 mA) on electrode E1 and positive (+4 mA) on electrode E3. Additionally, FIG. 3 shows that the stimulation parameters associated with this current pulse are set at a rate of 60 pulses per second (pps), and that the width of the pulse is about 300 microseconds (μs).

Still with reference to FIG. 3A, it is seen that at time t=2 ms, channel 2 of the IPG 100 is set to generate and apply a 6 mA pulse, having a repetition rate of 50 pps and a width of 300 μs, between electrode E8 (+6 mA) and electrodes E6 and E7 (−4 mA and −2 mA, respectively). That is, channel 2 of the IPG supplies a current pulse through electrode E8 (+6 mA) that is shared on its return path through electrode E6 (−4 mA) and electrode E7 (−2 mA).

As further seen in FIG. 3A, at time t=4 ms, channel 3 of the IPG 100 is set to generate and supply a 5 mA pulse to electrode E10 (+5 mA) which is returned through electrode E8 (−5 mA). This pulse has a rate of 60 pps, and a width of 400 μs. Similarly, it is seen that at time t=6 ms, channel 4 of the IPG is set to generate and supply a 4 mA pulse to electrode E14 (+4 mA) which is returned through electrode E13 (−4 mA). This channel 4 pulse has a rate of 60 pps and a width of 300 μs.

The particular electrodes that are used with each of the four channels of the IPG 100 illustrated in FIG. 3A are only exemplary of many different combinations of electrode pairing and electrode sharing that could be used. That is, any channel of the IPG may be programmably connected to any grouping of the electrodes, including the reference (or case) electrode. While it is typical that only two electrodes be paired together for use by a given channel of the IPG, as is the case with channels 1, 3 and 4 in the example of FIG. 3, it is to be noted that any number of electrodes may be grouped and used by a given channel. When more than two electrodes are used with a given channel, the sum of the current sourced from the positive electrodes should be equal to the sum of the current sunk (returned) through the negative electrodes, as is the case with channel 2 in the example of FIG. 3A (+6 mA sourced from electrode E8, and a total of −6 mA sunk to electrodes E6 [−4 mA] and E7 [−2 mA]).

As described above, it is thus seen that the IPG has, in a preferred embodiment, sixteen electrode contacts, each of which is independently programmable relative to stimulus polarity and amplitude for each of up to four different programmable channel assignments (groups or phase generators). In operation, each channel identifies which electrodes among the sixteen electrodes, E1, E2, E3, ... E16 and the IPG case electrode (reference electrode), are to output stimulation pulses in order to create an electric current field. All electrodes assigned to a given channel deliver their stimulation pulses simultaneously with the same pulse width and at the same pulse rate. For each channel, the IPG case electrode is programmable either as a Positive (passive anode) or OFF. Thus, monopolar stimulation is provided when the only electrode contact programmed to Positive is the IPG case electrode, and at least one other electrode is programmed to Negative. For each of the other electrodes, E1, E2, E3, ... E16, on each channel, the polarity is programmable to Negative (cathode) with associated negative current amplitude, Positive (anode) with an associated positive current limit amplitude, or Off. The amplitude is programmable from −12.7 mA to +12.7 mA in 0.1 mA steps. The total simultaneous current capability from all of the anodes to all of the cathodes is at least 20 mA when operating at 120 Hz and with a 0.5 millisecond pulse width into an equivalent 500 ohms load. (Equivalent load means all cathodes ganged through a single 500 ohm load into all anodes ganged.) The programming of the total current capability into all cathodes while a given channel pulse is active is limited to the maximum IPG channel current capability.

Because of power limitations, it is not possible to program the average stimulus current delivered by the IPG during all active phase periods to exceed 2 mA. An "active" phase period is a phase period of the stimulus current during which the stimulus current is being provided by one or more of the turned ON current sources. In contrast, a "passive" phase period (also sometimes referred to as a "recharge" phase period) is a phase period of the stimulus current during which the current sources are turned OFF, and the stimulus current results from a recharge or redistribution of the charge flowing from the coupling capacitance present in the stimulus circuit. (Note: the average stimulus current is determined as the sum of the average stimulus currents for all channels (groups). For a channel, the average stimulus current is determined as the stimulus rate times the sum of all phase one cathodic current amplitudes times the channel first phase period [pulse width] plus the sum of all active second phase anodic current amplitudes times the channel second phase (recharge) period).

Net dc charge transfer is prevented during stimulation through the use of coupling capacitors C1, C2, C3, ... C16 (see FIG. 4A or 4C) between the electrodes E1, E2, E3, ... E16 and the IPG output. Voltage build-up on the output coupling capacitors is prevented by applying a biphasic stimulus waveform with a 500 Kohm trickle recharge through the case electrode between application of the stimulus pulses.

As described in more detail below, to prevent patient discomfort due to rapidly increasing or decreasing amplitudes of stimulus current, a slow start/end feature is employed wherein changes in amplitude are limitable to occur slowly and smoothly over a transition period. The transition period is programmable from 1 to 10 seconds in 1 second increments. To ensure smoothness, individual amplitude step changes during the transition period are maintained at less than 5% of the programmed amplitude, or 0.1 mA, whichever is greater.

For each channel, the first phase period (pulse width) is programmable from 10 to 1000 microseconds (μs) in 10 μs steps. The inter-phase period between the First (Pulse Width) and Second (Recharge) phases is 100 μs. The Second (Recharge) phase period is programmable from 10 to 1500 μs in 10 μs increments. The Second (Recharge) phase type is programmable as either Passive or Active. The pulse rate is programmable in either a Normal or a High rate range. In the Normal Rate range, which covers 2 to 150 pulses per second (pps) in 1 pps steps, all channels are available. In the High Rate range, which covers 150 pps to 350 pps in 10 pps steps, 400 pps to 500 pps in 50 pps steps, and 600 pps to 1200 pps in 100 pps steps, only one channel may be available.

To prevent more than one channel from producing a stimulus current at the same time, i.e., to prevent current pulses from different channels that overlap, an overlap arbitration circuit may be employed (that is, the arbitration feature may be programmed ON or OFF for each channel) that determines which channel has priority. The sum of the next current for all channels with overlap arbitration (jitter) programmed OFF plus the maximum channel current of channels with overlap arbitration programmed ON should be programmed to be less than the maximum IPG current capability.

Figure 3B:
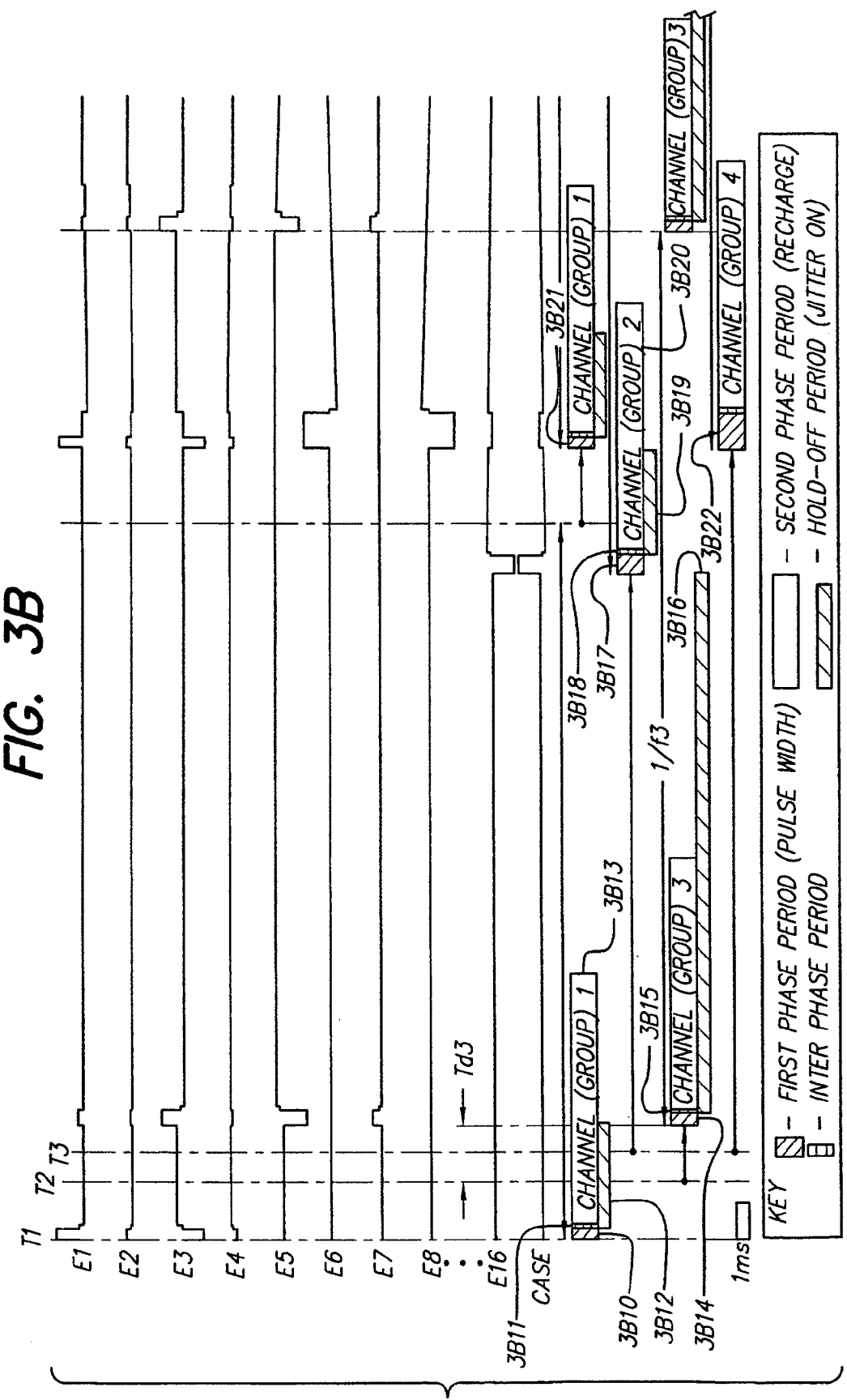
FIG. 3B is a timing waveform diagram that illustrates operation of multiple channels so as to prevent overlap between channels and/or to temporarily shut down a channel during passive recharge phases.

The arbitration circuit (shown in FIG. 4G as element 768), in a preferred embodiment, functions in accordance with the following principles. Once a non-overlapping channel begins a pulse, the start of pulses from any other non-overlapping channel is delayed until the ongoing pulse phase one is completed and a Hold-Off has been completed. The Hold-Off period is timed from the end of the first phase of the pulse. If the start of two or more non-overlapping channels are delayed by an ongoing pulse and Hold-Off, the pending channels are started in the order they would have occurred without arbitration. If two non-overlapping channels are scheduled to start simultaneously, the lower number channel takes priority and starts first (i.e., channel 1 before channel 2, channel 2 before channel 3, and channel 3 before channel 4). The Hold-Off period is programmable from 1 to 64 milliseconds in 1 millisecond increments. Current from any stimulus pulse (First phase) or active recharge (active second phase) is prevented from passing through any electrode undergoing passive recharge. the delivery of an active first phase or active second phase on any electrode takes precedence over all ongoing passive recharge phases. Electrodes undergoing passive recharge have their passive recharge phases temporarily interrupted during the active phase(s). If the electrode is not part of the active phase, it remains in a high impedance state (i.e., turned OFF) until the active phase is completed. The interpulse interval (1/Rate) is programmed such that it is greater than the sum of the first phase period plus the inter-phase period plus the second phase period for each channel. When passive recharge is programmed, the total second phase period available to complete recharge (not including interruptions for active phases) is at least 7 milliseconds for every pulse delivered The above arbitration circuit operating principles are illustrated, at least in part, in the timing waveform diagram of FIG. 3B. FIG. 3B shows the current stimulus waveforms associated with electrodes E1-E8, E16 and the case. As seen in FIG. 3B, and recognizing that a channel comprises those electrodes that provide a stimulus current of the same pulse width at the same time, Channel 1 comprises the group of electrodes E1, E2, E3, and E4; Channel 2 comprises the group of electrodes E16 and the case electrode; Channel 3 comprises the group of electrodes E3, E5 and E7; and Channel 4 comprises the group of electrodes E6 and E8. For purposes of FIG. 3B, Channels 1, 2 and 3 have arbitration (a hold-off period) programmed ON, while Channel 4 does not.

Still with reference to FIG. 3B, the normal sequence of Channel firings without arbitration, would be as follows: Channel 1 firing at time T1, Channel 3 firing at time T2, and Channels 2 and 4 both firing at time T3. However, with arbitration ON, the respective channel firings are ordered as follows: The First phase period for Channel 1, 3B10, comprises the time when electrode E1 and E2 function as anodes, and electrodes E3 and E4 function as cathodes, with most of the current being provided through electrodes E1 (anode) and E3 (cathode). Immediately after the First phase period 3B10, two events begin: (1) an inter-phase period 3B11, and (2) a hold-off period 3B12. The inter-phase period 3B11 (at least for the time scale represented in FIG. 3B) appears as a very narrow sliver of time. As soon as the inter-phase period 3B11 concludes, the Channel 1 Second Phase Period 3B13 begins, which Channel 1 Second Phase period is a fixed recharge period, e.g., a fixed period of 7 milliseconds (ms). The Hold-Off period 3B12 is a programmable delay, ranging from 1 to 64 ms. The Channel 1 Hold-Off period 3B12 shown in FIG. 3B is about 3 ms. During the Hold-Off Period 3B12, no other channel is permitted to generate a stimulus pulse. Thus, at time T2, when Channel 3 would normally fire, it is prevented from doing so. Rather, it must wait a time period Td3 until the Channel 1 Hold-Off Period 3B12 concludes. Similarly, at time T3, when Channels 2 and 4 would normally fire, they are prevented from doing so because the Channel Hold-Off period 3B12 has not yet concluded, and even if it had, they would have to wait for Channel 3 to fire first.

Still with reference to FIG. 3B, at the conclusion of the Channel 1 Hold-Off period 3B12, Channel 3 fires, which means a First Phase period 3B14 for Channel 3 begins. At this time, which is still during the Channel 1 Second Phase Period 3B13, the passive recharge which is taking place in electrodes E1, E2 and E3 is interrupted temporarily (e.g., for the duration of the active first phase period 3B14).

At the conclusion of the Channel 3 First Phase period 3B14, a Channel 3 Inter-Phase period 3B15 begins, as does a Channel 3 Hold-Off period 3B16. At the conclusion of the Inter-Phase period 3B15, the Channel 3 Second Phase begins, which is fixed at about 7 ms. The Channel 3 Hold-Off period 3B16 is programmed to be about 15 ms. Neither Channel 2 nor Channel 4 is allowed to fire during the Channel 3 hold-off period. As soon as the Channel 3 hold-off period 3B16 concludes, both Channel 2 and Channel 4 are past due for firing. Channel 2 fires first because it has a lower channel number than does Channel 4. Thus, at the conclusion of the Channel 3 hold-off period 3B16, a Channel 2 First Phase period 3B17 begins, followed by the commencement of both a Channel 2 inter-phase period 3B18 and a Channel 2 Hold-Off period 3B19. A Channel 2 Second Phase period 3B20 begins at the conclusion of the Channel 2 inter-phase period 3B18.

At the conclusion of the Channel 2 hold-off period 3B19, as seen in FIG. 3B, two events occur: (1) Channel 1 fires, which means a channel 1 First Phase period 3B21 begins; and (2) Channel 4 fires, which means a Channel 4 First Phase period 3B22 begins. Recall that Channel 4 does not have its arbitration feature programmed ON, hence, it fires just as soon as it can after the preceding Hold-Off period 3B19 terminates, which just happens to be at the same time that Channel 1 fires. Note that no electrodes are shared between Channels 1 and 4, and thus simultaneous firing is permitted if the timing is such that simultaneous firing is called for. During the firing of channels 1 and 4, Channel 2 is still experiencing a Second Phase passive recharge 3B20. Hence, this passive recharge is temporarily interrupted for electrodes E16 and the common (case) electrode during the active phase of Channels 1 and 4.

Continuing with FIG. 3B, the next channel to fire is Channel 3, which channel fires at its programmed rate, f3, as determined from its last firing (i.e., at a time interval 1/f3 from its prior firing)

Figure 3C:
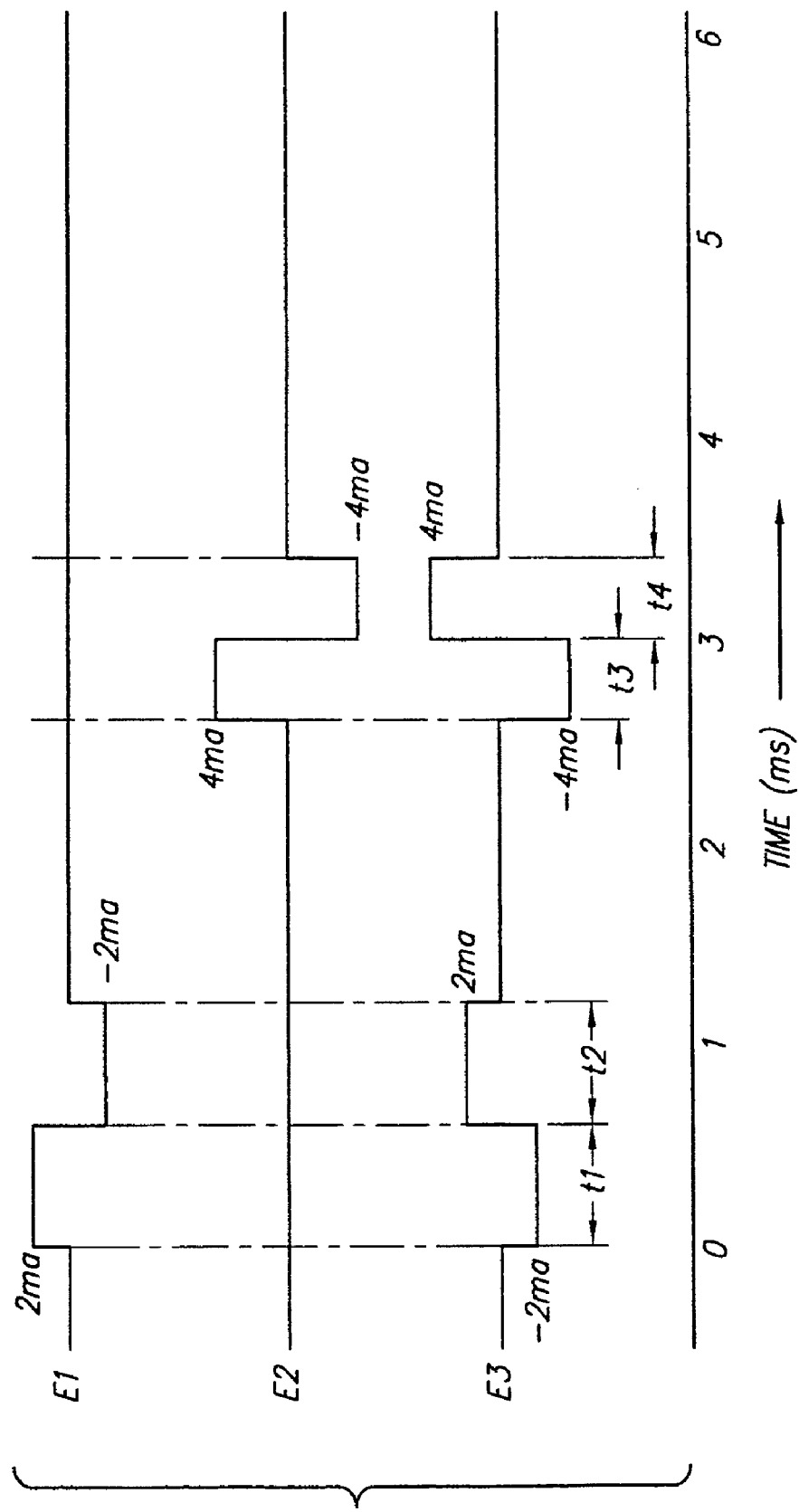
FIG. 3C is a timing diagram that illustrates the use of an active recharge phase to allow waveforms, e.g., symmetrical biphasic waveforms, which allow higher rates of stimulation.

It should be noted that the second phase period for each channel or group need not be a passive recharge period. Rather, as shown in FIG. 3C, the second phase can also be an active phase, i.e., a phase when one or more current sources are turned ON. In a preferred embodiment, the second phase period and amplitude shall be programmed to create a symmetrical biphasic waveform when a channel is programmed to active recharge. For each electrode on channels programmed to an active Second Phase (Recharge) type, the recharge amplitude shall be programmed to the opposite polarity and amplitude as the first phase. Using active recharge in this manner allows faster recharge while avoiding the charge imbalance that could otherwise occur Thus, as seen in FIG. 3C, beginning at 0 ms, electrode E1 is programmed to produce a first phase current of +2 ma (anode) at the same time that electrode E3 is programmed to produce first phase current of −2 ma (cathode). The first phase (pulse width) is programmed to last about 0.6 ms. At the conclusion of the first phase, an active second phase begins. During this active second phase, which is also programmed to last about 0.6 ms, the amplitude of electrode E1 is programmed to −2 mA, while the amplitude of electrode E3 is programmed to +2 mA, thereby creating a symmetrical biphasic current pulse and a balanced charge condition. (It should also be noted that a balanced charge condition could also be obtained without having a symmetrical biphasic pulse, if desired, by simply assuring that the total charge during the first phase of the biphasic pulse, i.e., amplitude× duration, is equal to the total charge during the second phase.)

As further seen in FIG. 3C, beginning at about 2.6 ms from the 0 reference point, electrode E2 is programmed to produce a first phase current of +4 ma (anode) at the same time that electrode E3 is programmed to produce first phase current of −4 ma (cathode). The first phase (pulse width) is programmed to last about 0.4 ms. At the conclusion of the first phase, an active second phase begins. During this active second phase, which is also programmed to last about 0.4 ms, the amplitude of electrode E2 is programmed to −4 mA, while the amplitude of electrode E3 is programmed to +4 mA, thereby creating a symmetrical biphasic current pulse and a balanced charge condition.

Figure 4A:
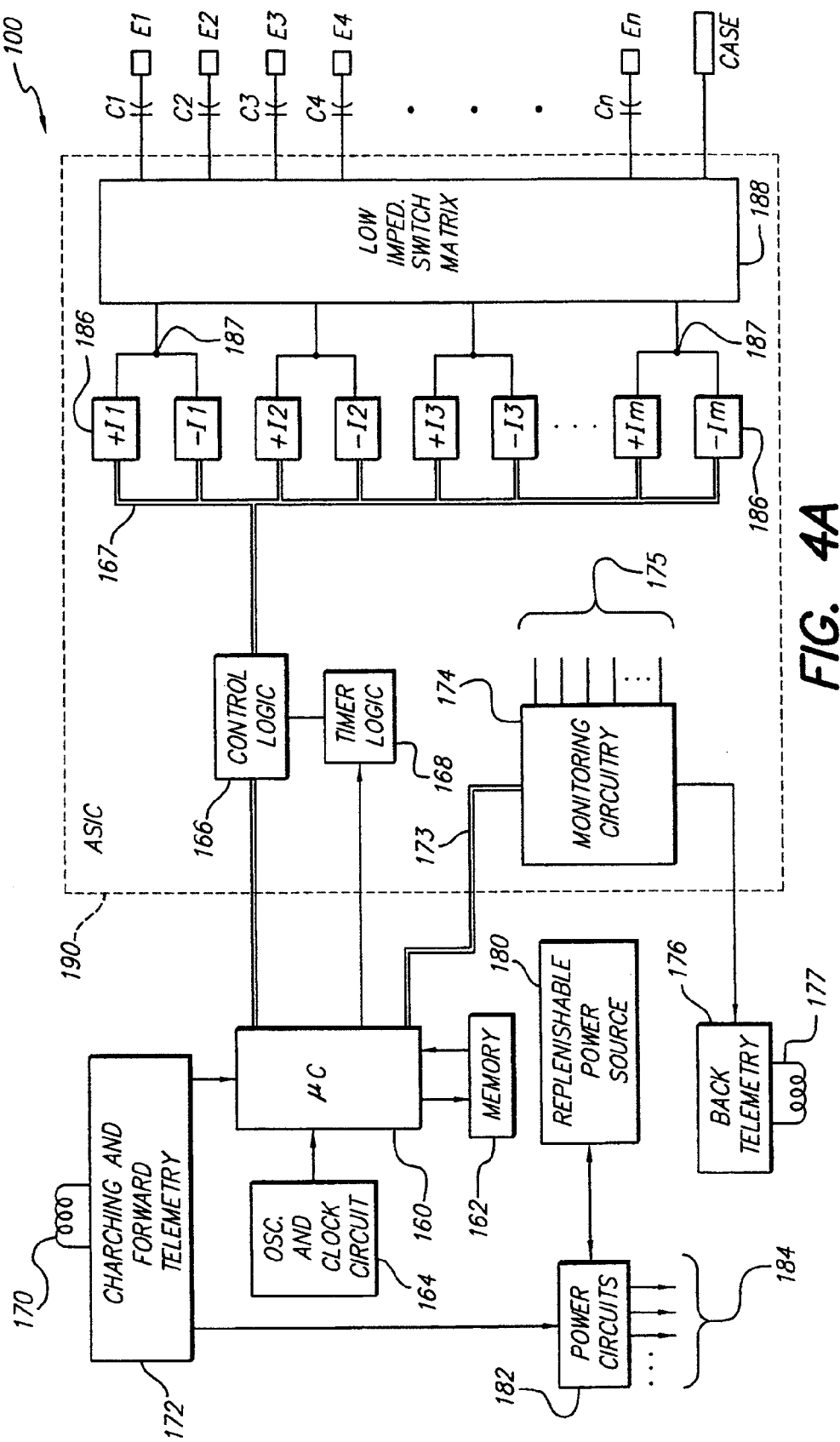
FIG. 4A is a functional block diagram that illustrates the main components of an implantable pulse generator (IPG) in accordance with a first IPG embodiment of the invention.

Turning next to FIG. 4A, a block diagram is shown that illustrates the main components of one embodiment of an implantable pulse generator, or IPG 100, that may be used with the invention. As seen in FIG. 4A, the IPG includes a microcontroller (μC) 160 connected to memory circuitry 162. The μC 160 typically comprises a microprocessor and associated logic circuitry, which in combination with control logic circuits 166, timer logic 168, and an oscillator and clock circuit 164, generate the necessary control and status signals which allow the μC to control the operation of the IPG in accordance with a selected operating program and stimulation parameters. The operating program and stimulation parameters are typically programmably stored within the memory 162 by transmitting an appropriate modulated carrier signal through a receiving coil 170 and charging and forward telemetry circuitry 172 from an external programming unit, e.g., a handheld programmer (HHP) 202 and/or a clinician programmer (CP) 204, assisted as required through the use of a directional device 206 (see FIG. 1). (The handheld programmer is thus considered to be in "telecommunicative" contact with the IPG; and the clinician programmer is likewise considered to be in telecommunicative contact with the handheld programmer, and through the handheld programmer, with the IPG.) The charging and forward telemetry circuitry 172 demodulates the carrier signal it receives through the coil 170 to recover the programming data, e.g., the operating program and/or the stimulation parameters, which programming data is then stored within the memory 162, or within other memory elements (not shown) distributed throughout the IPG 100.

Still with reference to FIG. 4A, the microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes E1 . . . En, and the like. Informational data sensed through the monitoring circuit 174 may be sent to a remote location external the IPG (e.g., a non-implanted location) through back telemetry circuitry 176, including a transmission coil 177.

The operating power for the IPG 100 is derived from a replenishable power source 180, e.g., a rechargeable battery and/or a supercapacitor. Such power source 180 provides an unregulated voltage to power circuits 182. The power circuits 182, in turn, generate the various voltages 184, some of which are regulated and some of which are not, as needed by the various circuits located within the IPG. The power circuits 182 further selectively direct energy contained within the carrier signal, obtained through the charging and forward telemetry circuit 172, to the replenishable power source 180 during a charging mode of operation. In this way, the power source 180 may be recharged when needed. A particular feature of the present invention is the manner in which such recharging occurs, on an as-needed basis.

In a preferred embodiment, the power source 180 of the IPG 100 comprises a rechargeable battery, and more particularly a rechargeable Lithium Ion battery. Recharging occurs inductively from an external charging station (shown in FIG. 8) to an implant depth of approximately 2-3 cm. Because the SCS IPG 100 could accept or receive a charge from an unauthorized source, internal battery protection circuitry is employed, for safety reasons, to protect the battery (e.g., to prevent the battery from being overcharged and/or to accept a charge only from an authorized charging device). The battery is chargeable to 80% of its capacity within about an hour, and is chargeable to its full capacity within about two hours. Moreover, at an 80% charge, a single battery discharge is able to support stimulation at typical parameter settings on one channel (electrode group) for approximately three weeks; and on 4 channels for approximately one week, after 10 years of cycling. Thus, it is seen that the IPG 100 truly offers a long life.

Additionally, the IPG 100 is able to monitor and telemeter the status of its replenishable power source 180 (e.g., rechargeable battery) each time a communication link is established with the external patient programmer 202. Such monitoring not only identifies how much charge is left, but also charge capacity. Typically, a telecommunicative link is established, and hence battery monitoring may occur, each time a programming event occurs, i.e., each time the patient or medical personnel change a stimulus parameter, or initiate a charging operation.

Still referring to FIG. 4A, the power circuits 182 advantageously include protection circuitry that protects the replenishable power source 180 from overcharging. Also, safeguarding features are incorporated that assure that the power source is always operated in a safe mode upon approaching a charge depletion. Potentially endangering failure modes are avoided and prevented through appropriate logic control that is hard-wired into the device, or otherwise set in the device in such a way that the patient cannot override them.

Still with reference to FIG. 4A, it is seen that a plurality m of independent current source pairs, 186+l1, 186−l1, 186+l2, 186−l2, 186+l3, 186−l3, . . . 186+lm, 186−lm are coupled to the control logic 166 via control bus 167. One current source of each pair of current sources functions as a positive (+) current source, while the other current source of each pair functions as a negative (−) current source. The output of the positive current source and the negative current source of each pair of current sources 186 is connected to a common node 187. This common node 187, in turn, is connected through a low impedance switching matrix 188 to any of n electrode nodes E1, E2, E3, . . . En, through respective coupling capacitors C1, C2, C3, . . . Cn. (Note: a second embodiment of the IPG, see FIGS. 4B and 4C, discussed below, does not use a low impedance switching matrix 188. Rather, there is an independent bi-directional current source for each of the sixteen electrodes.) Through appropriate control of the switching matrix 188, when used (FIG. 4A), or through operation of the independent bi-directional current sources, when used (FIGS. 4B and 4C), any of the m current source nodes 187 may be connected to any of the electrode nodes E1, E2, E3, . . . En. Thus, for example, it is possible to program the current source 186+l1 to produce a pulse of +4 mA (at a specified rate and for a specified duration), and to synchronously program the current source 186−l2 to similarly produce a pulse of −4 mA (at the same rate and pulse width), and then connect the 186+l1 node 187 to electrode node E3 and the 186−l2 node to electrode node E1 at relative time t=0 ms (and at a recurring rate thereafter) in order to realize the operation of channel 1 depicted, e.g., in the timing diagram of FIG. 3A. In a similar manner, the operation of channels 2, 3 and 4 shown in FIG. 3A may likewise be realized.

As described, it is thus seen that any of the n electrodes may be assigned to up to k possible groups (where k is an integer corresponding to the number of channels, and in a preferred embodiment is equal to 4). Moreover, any of the n electrodes can operate, or be included in, any of the k channels. The channel identifies which electrodes are selected to synchronously source or sink current in order to create an electric field. Amplitudes and polarities of electrodes on a channel may vary, e.g., as controlled by the patient hand held programmer 202. External programming software in the clinician programmer 204 is typically used to assign a pulse rate and pulse width for the electrodes of a given channel.

Hence, it is seen that each of the n programmable electrode contacts can be programmed to have a positive (sourcing current), negative (sinking current), or off (no current) polarity in any of the k channels.

Moreover, it is seen that each of the n electrode contacts can operate in a bipolar mode or multipolar mode, e.g., where two or more electrode contacts are grouped to source/sink current at the same time. Alternatively, each of the n electrode contacts can operate in a monopolar mode where, e.g., the electrode contacts associated with a channel are configured as cathodes (negative), and the case electrode, on the IPG case, is configured as an anode (positive).

Further, the amplitude of the current pulse being sourced or sunk from a given electrode contact may be programmed to one of several discrete levels. In one embodiment, the currents can be individually set from ±0 to ±10 mA, in steps of 0.1 mA, within the output voltage/current requirements of the device. Additionally, in one embodiment, at least one channel of electrodes is capable of an output of at least ±20 mA (distributed among the electrodes included in the channel group). The current output capacity of individual electrodes are limited when operating with more than one other electrode of the same polarity in a given channel in order to assure that the maximum current values are maintained. Additionally, in order to prevent "jolts", current amplitude changes are always gradually changed, e.g., in a ramping fashion, from one value to another within the range of values available between the settings. Such ramping feature is also used when initially powering on the IPG, thereby preventing full magnitude stimulus pulses from being delivered to the patient during a ramping-up time period. The ramping-up time period may vary, depending upon the channel and programmed amplitude, between about 1 and 10 seconds. This pulse ramping feature is explained more fully below in conjunction with FIG. 10.

Also, in one embodiment, the pulse width of the current pulses is adjustable in convenient increments. For example, the pulse width range is preferably at least 0 to 1 ms in increments of 10 µs. Generally, it is preferred that the pulse width be equal for all electrodes in the same channel.

Similarly, in one embodiment, the pulse rate is adjustable within acceptable limits. For example, the pulse rate preferably spans at least two ranges: (1) a normal rate; and (2) a high rate. The normal rate range covers 0-150 pps per channel in approximately 1 pps increments. The high rate range covers 100-1200 pps with appropriate restrictions on pulse width, and need only be available on one or two channels. When used, the high rate range limits operation of the additional channels at the normal rates when stimulation and/or power conflicts are determined to be present.

Because the IPG 100 is typically only capable of delivering current pulses up to ±20 mA in amplitude at any instant in time, the SCS system also regulates the channel rates to prevent overlap (i.e., to prevent two or more pulses from different channels from occurring at the same time). Such channel rate regulation is transparent to the patient.

The stimulation pulses generated by the IPG 100 must also be charged balanced. This means that the amount of positive charge associated with a given stimulus pulse must be offset with an equal and opposite negative charge. Charge balance may be achieved through a coupling capacitor, which provides a passive capacitor discharge that achieves the desired charge balanced condition. Such passive capacitor discharge is evident in the waveforms depicted in FIG. 3A as the slowly decaying waveform following the short trailing edge of each pulse. Alternatively, active biphasic or multiphasic pulses with positive and negative phases that are balanced may be used to achieve the needed charge balanced condition.

In some embodiments of the invention, a real-time clock is also incorporated within the timing circuits of the IPG 100. Such real-time clock advantageously allows a run schedule to be programmed. That is, the patient can schedule auto-run times for IPG operation at certain times of the day. When an auto-run time begins, all channels are enabled and provide a previously-programmed pattern of stimulus currents, i.e., current pulses having a programmed width, rate, and amplitude are generated and delivered through each channel. The auto-run time continues for a set time period, e.g., several hours, or for only a few minutes. When a programming change is made by the patient or other medical personnel, the auto-run time, when enabled at the programmed time of day, invokes the most recent programming changes made to each channel.

An important feature included within the IPG 100 is its ability to measure electrode impedance, and to transfer the impedance thus measured back to a remote programmer, or other processor, through the back telemetry circuits 176. Also, the microcontroller 160, in combination with the other logic circuits, may also be programmed to use the electrode impedance measurements to adjust compliance voltages and to thereby better maintain low battery consumption. In one embodiment of the IPG 100, electrode impedance is measured for each electrode contact by sourcing or sinking a 1 mA current pulse from the electrode contact to the case electrode, measuring the voltage at the electrode contact, and computing the resulting impedance. (Impedance is equal to voltage/current.) For a spinal cord implantation, the electrode impedance will typically range between about 400 ohms and 1000 ohms. The impedance measuring feature is described in more detail below in conjunction with the description of FIGS. 11A and 11B.

The type of current sources depicted in FIG. 4A may be realized by those of skill in the art using the teachings of International Patent Application Serial Number PCT/US99/14190, filed Jun. 23, 1999, entitled "Programmable Current Output Stimulus Stage for Implantable Device", published as International Publication No. WO-00/00251, on Jan. 6, 2000, and claiming priority to U.S. Patent Application Ser. No. 60/090,833, filed Jun. 26, 1998, which international publication is incorporated herein by reference.

Advantageously, by using current sources of the type disclosed in the referenced international patent application, or equivalent, the IPG 100 is able to individually control the n electrode contacts associated with the n electrode nodes E1, E2, E3, . . . En. Controlling the current sources and switching matrix 188 using the microcontroller 160, in combination with the control logic 166 and timer logic 168, thereby allows each electrode contact to be paired or grouped with other electrode contacts, including the monopolar case electrode, in order to control the polarity, amplitude, rate, pulse width and channel through which the current stimulus pulses are provided.

As shown in FIG. 4A, much of circuitry included within the embodiment of the IPG 100 illustrated in FIG. 4A may be realized on a single application specific integrated circuit (ASIC) 190. This allows the overall size of the IPG 100 to be quite small, and readily housed within a suitable hermetically-sealed case. The IPG 100 includes n feedthroughs to allow electrical contact to be individually made from inside of the hermetically-sealed case with the n electrodes that form part of the lead system outside of the case. The IPG case is preferably made from titanium and is shaped in a rounded case, as illustrated, e.g., in FIG. 2B. The rounded IPG case has a maximum circular diameter D of about 50 mm, and preferably only about 45 mm. The implant case has smooth curved transitions that minimize or eliminate edges or sharp corners. The maximum thickness W of the case is about 10 mm, and preferably only about 8 mm.

Figure 4B:
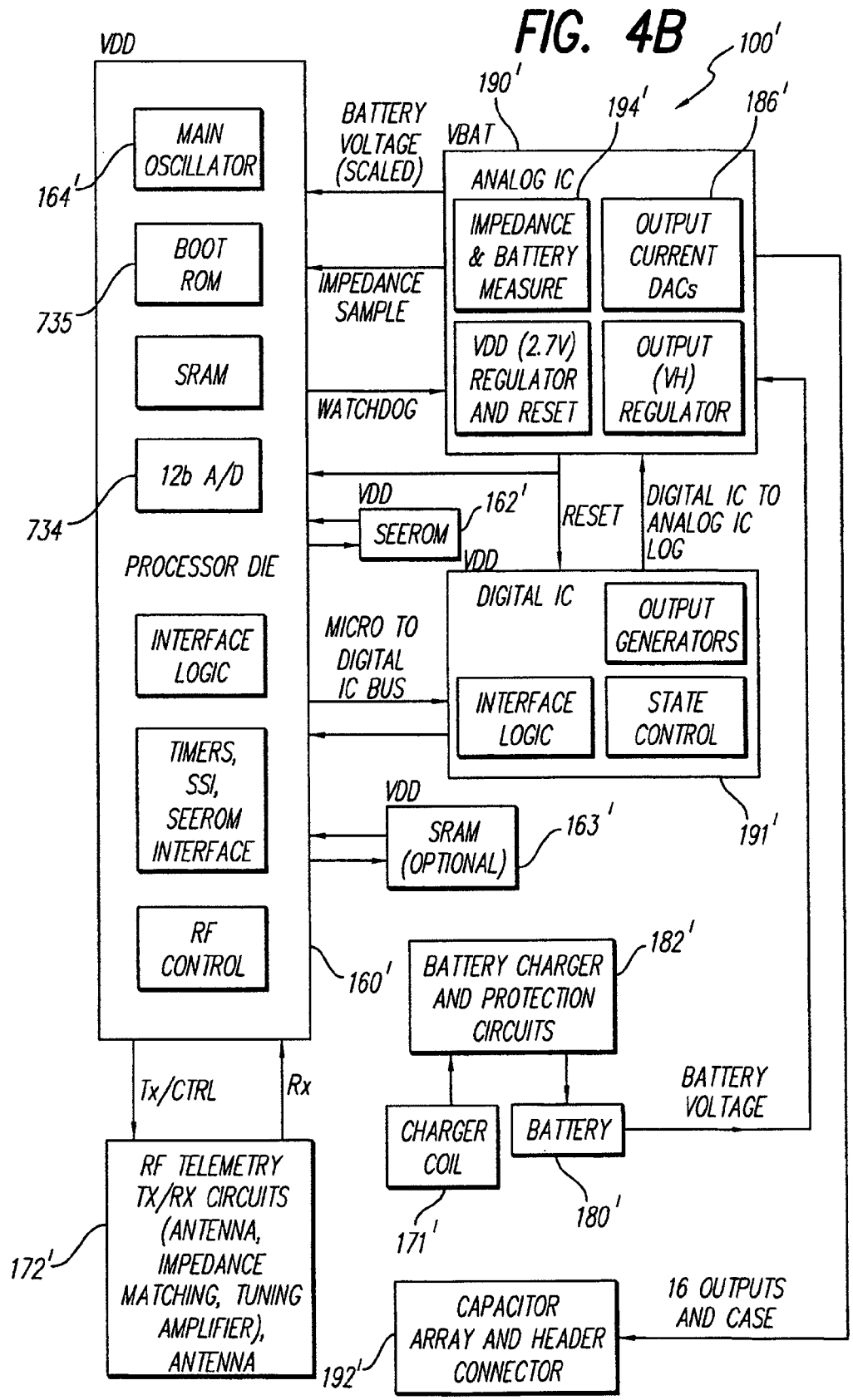
FIG. 4B shows an IPG hybrid block diagram that illustrates the architecture of an IPG made in accordance with a second IPG embodiment of the invention.

Turning next to FIG. 4B, a hybrid block diagram of an alternative embodiment of an IPG 100' that may be used with the invention is illustrated. The IPG 100' includes both analog and digital dies, or integrated circuits (IC's), housed in a single hermetically-sealed rounded case having a diameter of about 45 mm and a maximum thickness of about 10 mm. Many of the circuits contained within the IPG 100' are identical or similar to the circuits contained within the IPG 100, shown in FIG. 4A. The IPG 100' includes a processor die, or chip, 160', an RF telemetry circuit 172' (typically realized with discrete components), a charger coil 171', a lithium ion battery 180', a battery charger and protection circuits 182', memory circuits 162' (SEEPROM) and 163' (SRAM), a digital IC 191', an analog IC 190', and a capacitor array and header connector 192'.

The capacitor array and header connector 192' includes 16 output decoupling capacitors, as well as respective feedthrough connectors for connecting one side of each decoupling capacitor through the hermetically-sealed case to a connector to which the electrode array 110, or lead extension 120, may be detachably connected.

The processor 160' is realized with an application specific integrated circuit (ASIC) that comprises the main device for full bi-directional communication and programming. The processor 160' utilizes a 8086 core (the 8086 is a commercially-available microprocessor available from, e.g., Intel), or a low power equivalent thereof, 16 kilobytes of SRAM memory, two synchronous serial interface circuits, a serial EEPROM interface, and a ROM boot loader 735. The ROM boot loader 735 is described in more detail below in conjunction with FIG. 7F. The processor die 160' further includes an efficient clock oscillator circuit 164' and a mixer and modulator/demodulator circuit implementing the QFAST RF telemetry method supporting bi-directional telemetry at 8 Kbits/second. QFAST stands for "Quadrature Fast Acquisition Spread Spectrum Technique", and represents a known and viable approach for modulating and demodulating data. The QFAST RF telemetry method is further disclosed in U.S. Pat. No. 5,559,828, incorporated herein by reference. An analog-to-digital converter (A/D) circuit 734 is also resident on the processor 160' to allow monitoring of various system level analog signals, impedances, regulator status and battery voltage. In the preferred embodiment, the A/D converter circuit 734 comprises a twelve-bit A/D converter. The processor 160' further includes the necessary communication links to other individual ASIC's utilized within the IPG 100'.

The processor 160', like all similar processors, operates in accordance with a program that is stored within its memory circuits. In this instance, such program control is properly referred to as "firmware" (as opposed to software) because the program is digitally stored in a read only memory, or a programmable read only memory, and is not easily altered or changed (even though control parameters used with such program are readily changed).

The analog IC (AIC) 190' comprises an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function. The main area of the analog 190' is devoted to the current stimulus generators 186'. These generators 186' may be realized using the circuitry described in the previously-referenced PCT application, Serial No. PCT/US99/14190, or similar circuitry. These generators 186' are designed to deliver up to 20 mA aggregate and up to 12.7 mA on a single channel in 0.1 mA steps, which resolution requires that a seven (7) bit digital-to-analog (DAC) circuit be employed at the output current DAC 186'. Regulators for the IPG 100' supply the processor and the digital sequencer with a voltage of 2.7 V±10%. Digital interface circuits residing on the AIC 190' are similarly supplied with a voltage of 2.7 V±10%. A regulator programmable from 5V to 18V supplies the operating voltage for the output current DACs 186'.

Figures 1, 4C:
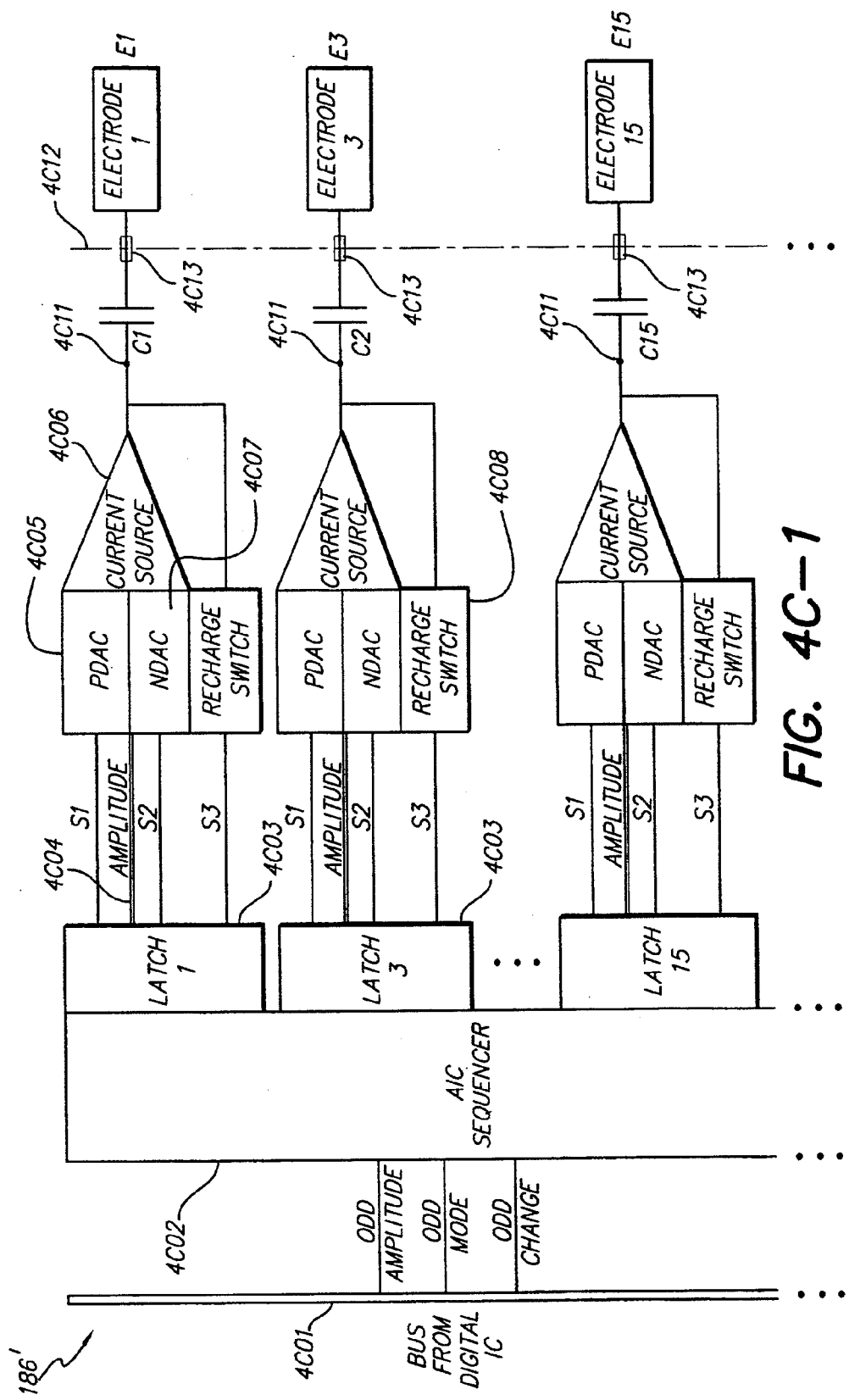
FIG. 4C is a block diagram of the analog integrated circuit (AIC) used, inter alia, to provide the output of the stimulus generators within the IPG hybrid architecture shown in FIG. 4B.
Figures 2, 4C:
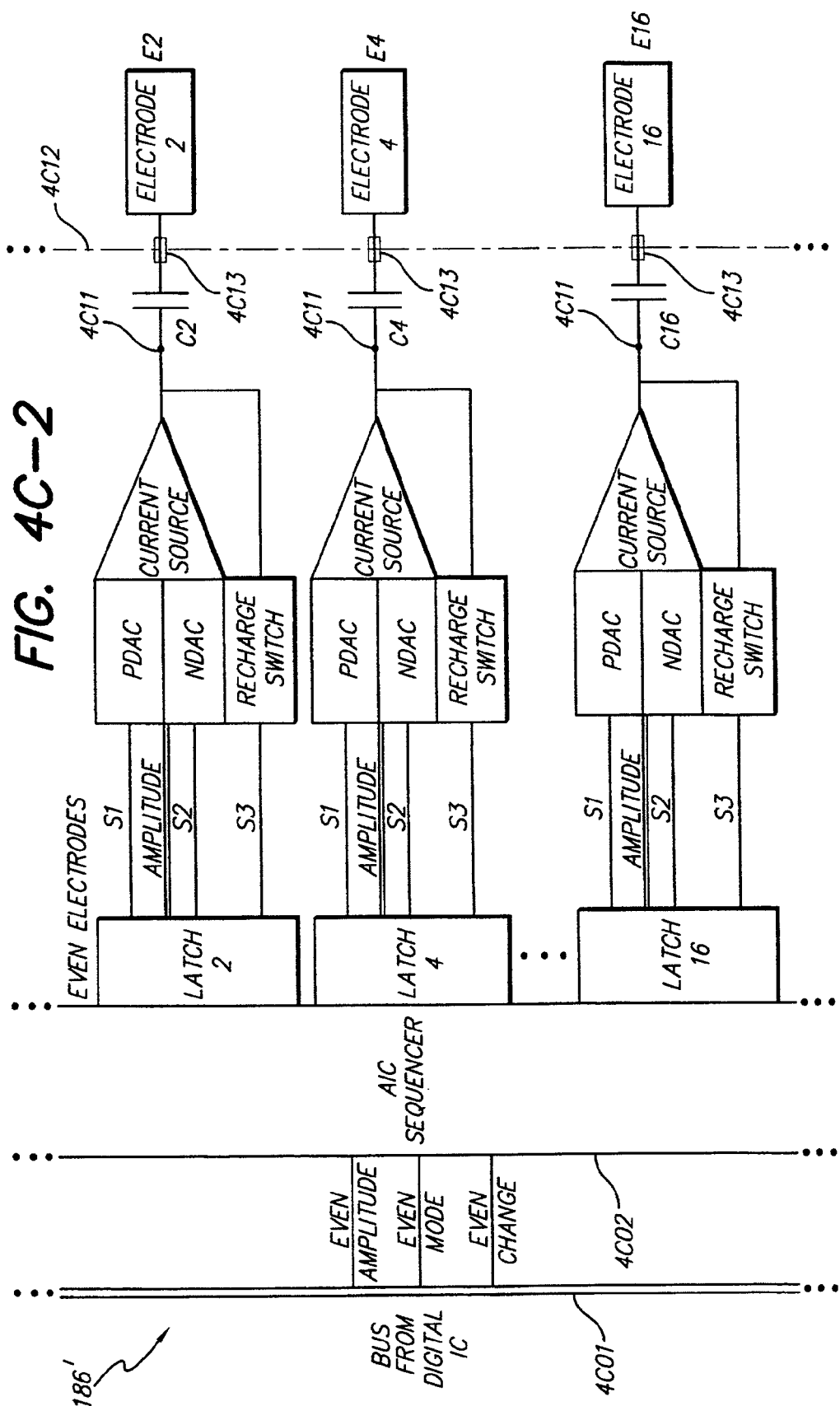
Figures 3, 4C:
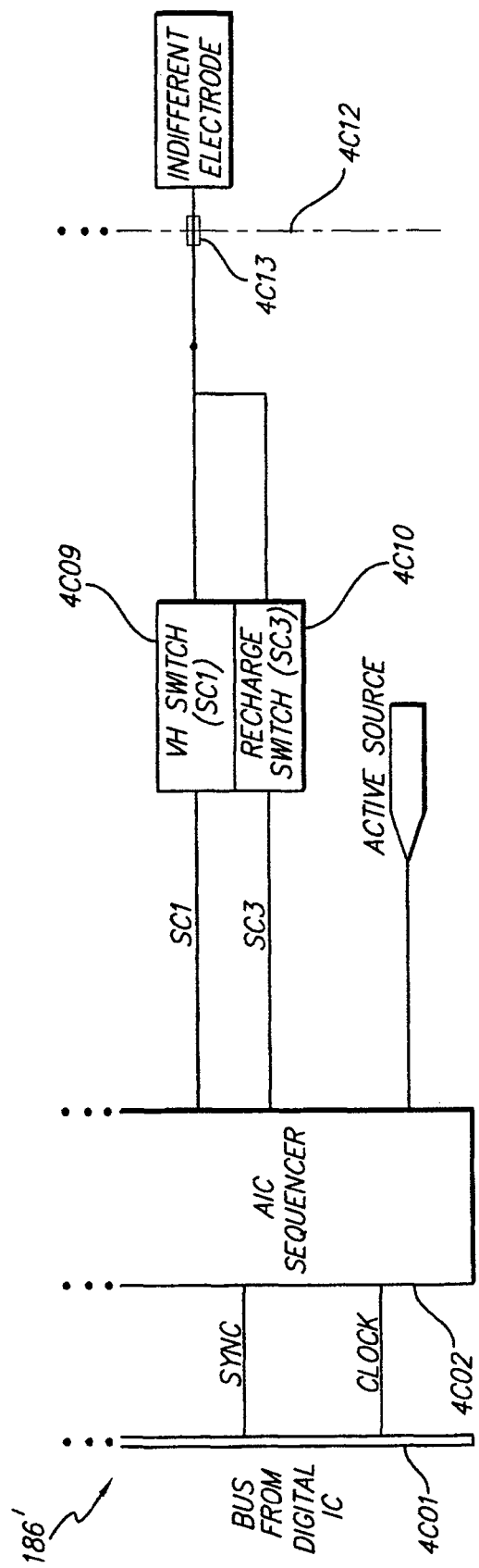

A block diagram of the output stimulus generators 186' included within the AIC 190' is shown in FIG. 4C. As seen in FIG. 4C, a data bus 4C01 from the digital IC 191' couples data received from the digital IC to AIC sequencer circuits 4C02. Such data includes odd and even amplitude data, odd and even mode data, and odd and even change data, where "odd" and "even" refer to the electrode number (with electrodes E1, E3, E5, etc. being "odd" electrodes; and electrodes E2, E4, E6, etc., comprising "even" electrodes). A multiplicity of latch circuits 4C03 are connected to the AIC sequencer 4C02, one latch circuit for each electrode. Hence, where there are sixteen electrodes, E1, E2, . . . E16, there are sixteen identical latch circuits 4C03. Each latch circuit includes an amplitude bus 4C04 on which the amplitude data is placed, an S1 line for designating a positive amplitude, an S2 line for designating a negative amplitude, and an S3 line for designating a recharge state. A PDAC circuit 4C05 is enabled by a signal on the S1 line when a current having the amplitude specified on the amplitude bus 4C04 is to be sourced from a current source 4C06 through a coupling capacitor Cn, where n is an integer from 1 to 16. Similarly, an NDAC circuit 4C07 is enabled by a signal on the S2 line when a current having the amplitude specified on the amplitude bus 4C04 is to be sunk into the current source 4C06 through the coupling capacitor Cn. A recharge switch 4C08 is enabled by the signal on the S3 line when it is desired to remove the charge from the coupling capacitor Cn. Another switch 4C09 allows an indifferent electrode 4C11, e.g., the case of the IPG, to be turned on upon receipt of an SC1 signal. Similarly, a recharge switch 4C10 allows the indifferent electrode 4C11 to be selectively connected to ground, or another voltage source, upon receipt of an SC2 signal.

From FIG. 4C, it is seen that the analog IC 186' includes a multiplicity of output current sources 4C06, e.g., sixteen bi-directional output current sources, each configured to operate as a DAC current source. Each DAC output current source 4C06 may source or sink current, i.e., each DAC output current source is bi-directional. Each DAC output current source is connected to an electrode node 4C11. Each electrode node 4C11, in turn, is connected to a coupling capacitor Cn. The coupling capacitors Cn and electrode nodes, as well as the remaining circuitry on the analog IC 186', are all housed within the hermetically sealed case of the IPG 100.

The dashed-dotted line 4C12 represents the boundary between the sealed portion of the IPG case and the unsealed portion. A feedthrough pin 4C13, which is included as part of the header connector 192' (FIG. 4B), allows electrical connection to be made between each of the coupling capacitors Cn and the respective electrodes E1, E2, E3, . . . , or E16, to which the DAC output current source is associated.

Returning again to FIG. 4B, the digital IC (DigIC) 191' functions as the primary interface between the processor 160' and the AIC output circuits 186'. The main function of the DigIC 191' is to provide stimulus information to the output current generator register banks. The DigIC 191' thus controls and changes the stimulus levels and sequences when prompted by the processor 160'. In a preferred embodiment, the DigIC 191' comprises a digital application specific integrated circuit (digital ASIC). A block diagram of the DigIC 191' is shown in FIG. 4G.

Figures 1, 4D:
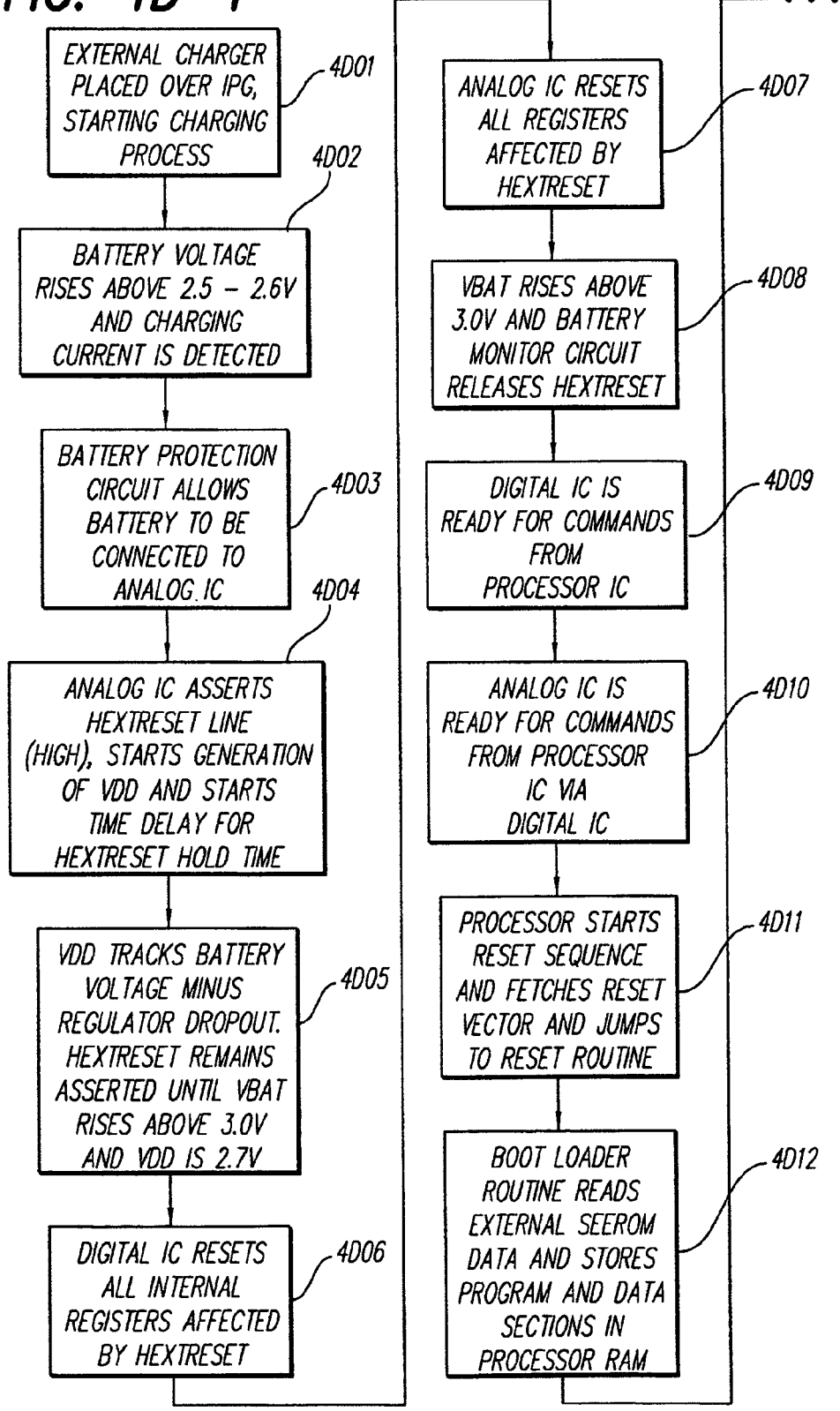
FIG. 4D is a flow chart illustrating a representative IPG power-up reset sequence.
Figures 2, 4D:
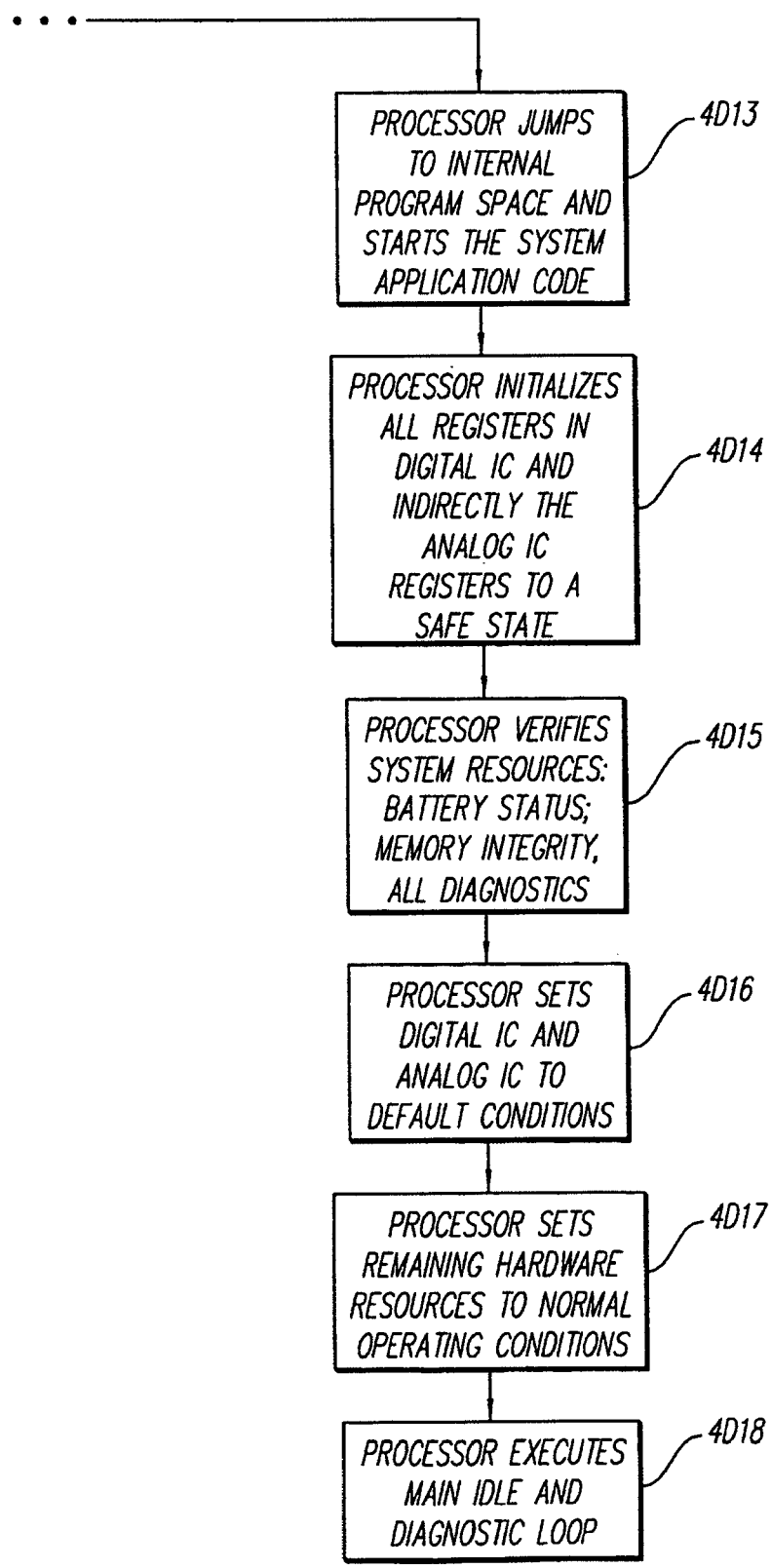
Figures 1, 4E:
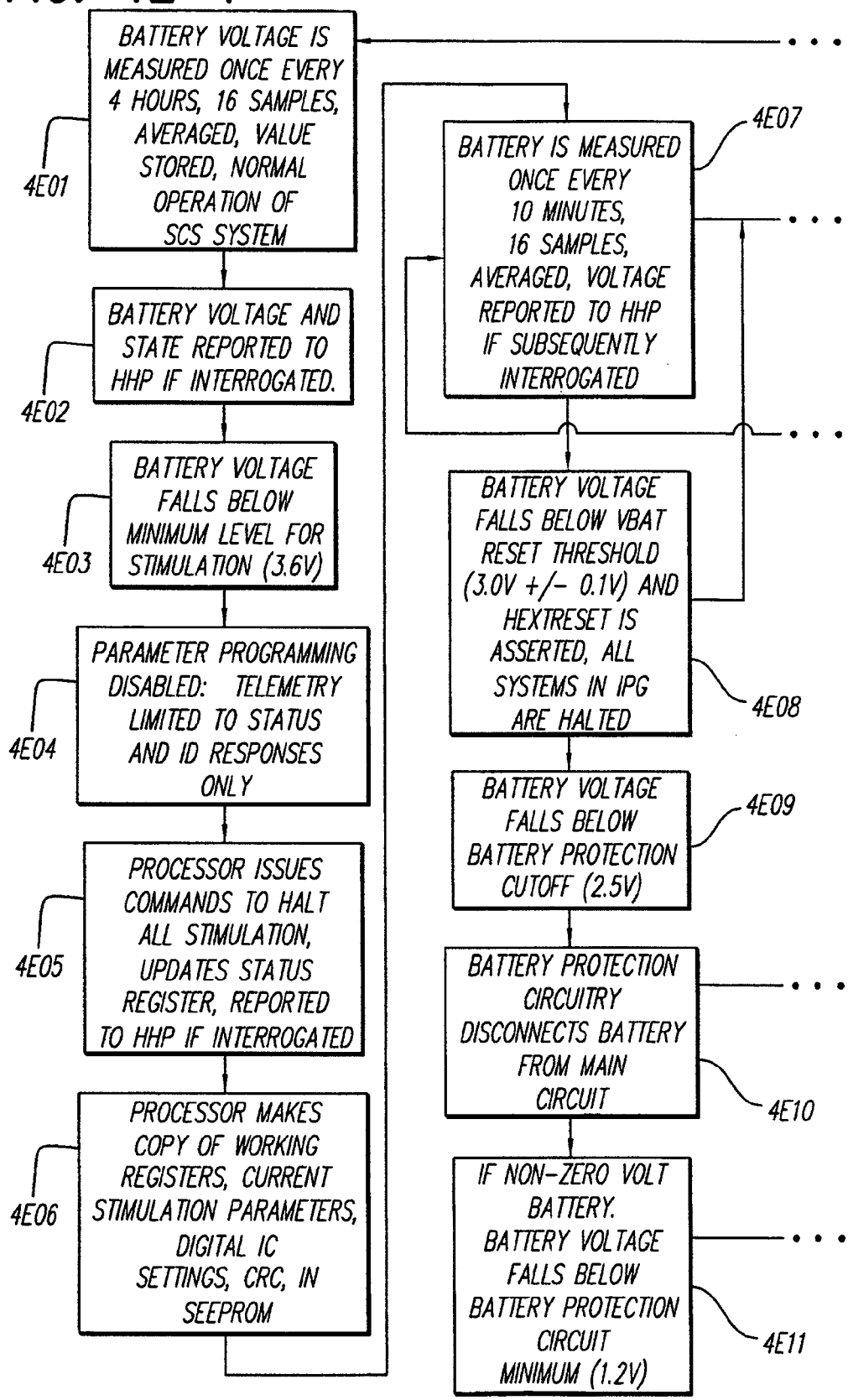
FIG. 4E is a flow chart illustrating a representative low battery shutdown and recovery sequence.
Figures 2, 4E:
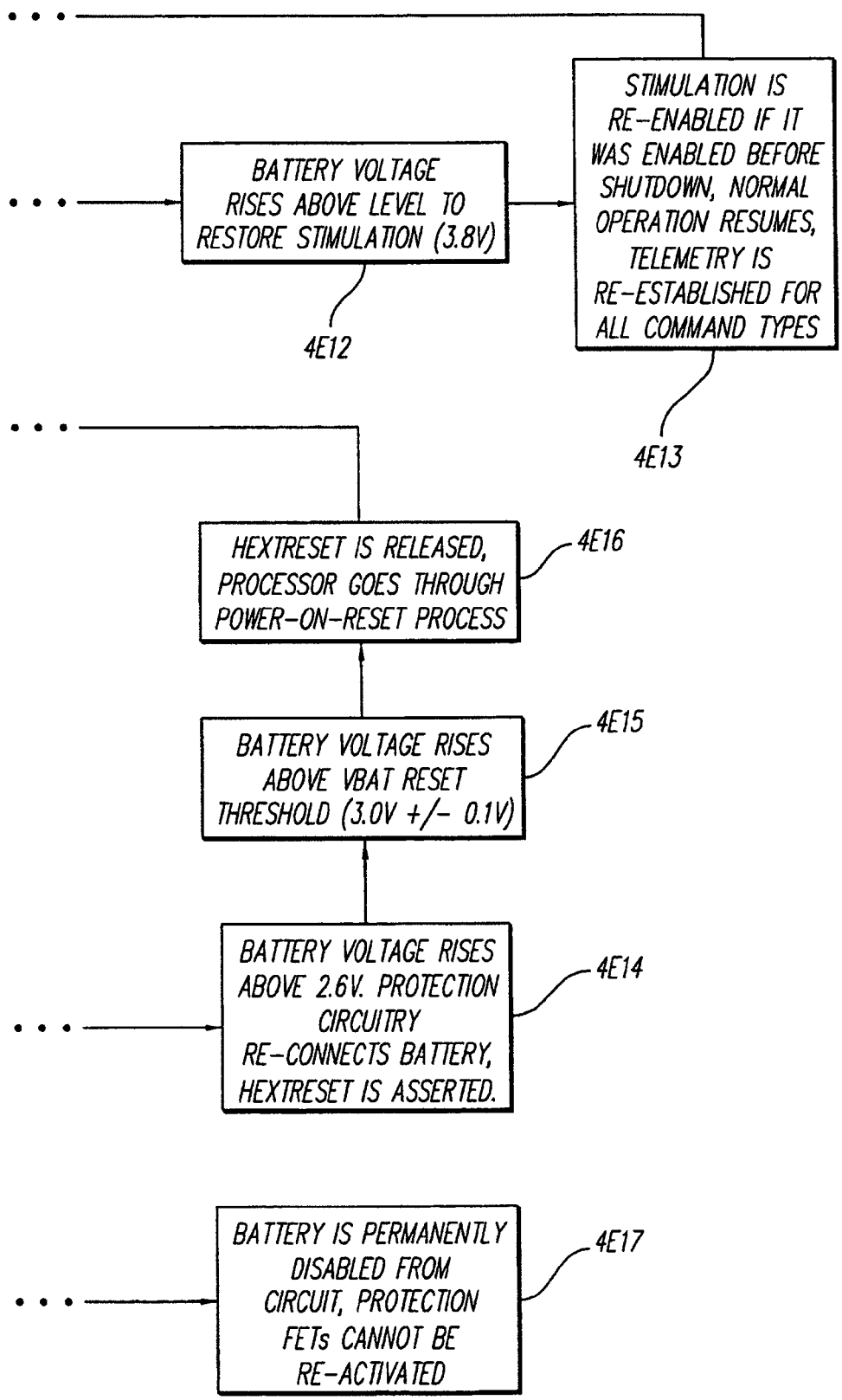
Figure 4F:
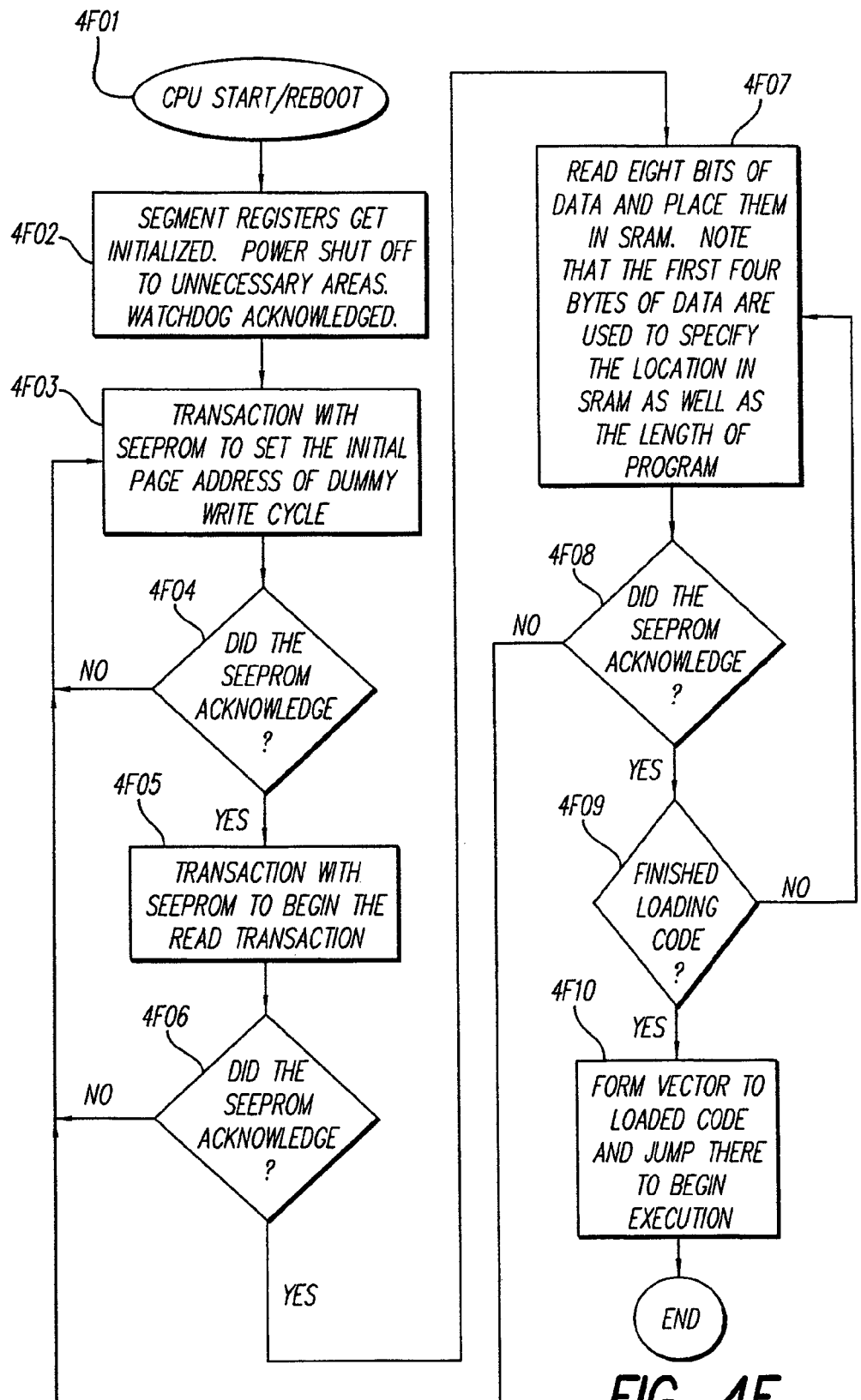
FIG. 4F is a flow chart that illustrates the boot sequence used within the processor chip of the IPG shown in FIG. 4B.
Figure 4G:
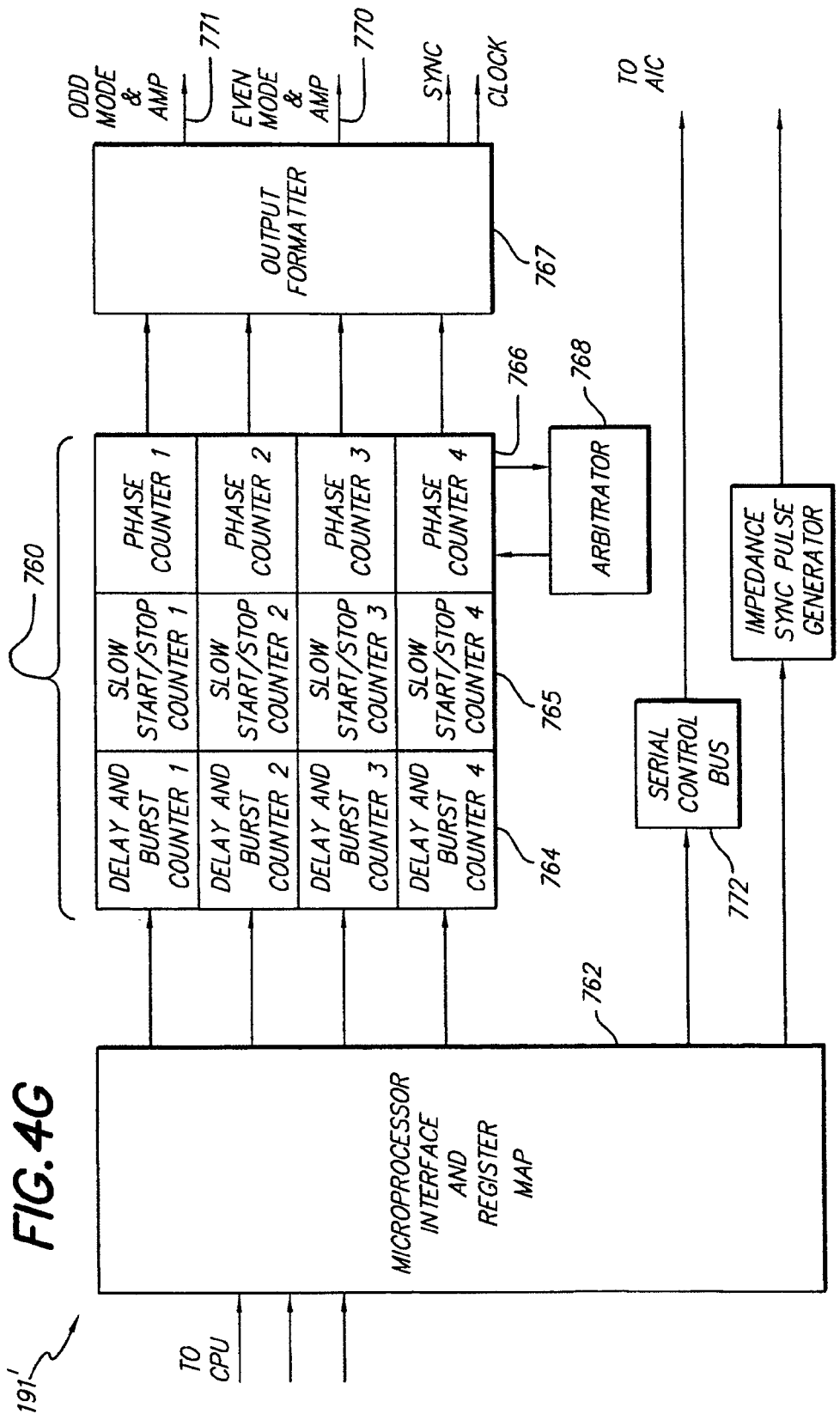
FIG. 4G is a block diagram of the digital application specific integrated circuit (Digital ASIC) used within the IPG hybrid architecture shown in FIG. 4B.

As seen in FIG. 4G, the digital ASIC 191' receives signals from the processor IC (CPU) 160' through an interface and register map circuit 762. The interface and register map circuit 762 implements a standard 8086 memory map interface between the processor IC 160' and the digital ASIC 191'. All read and write transactions are done in 16 bit words. Included as part of the digital ASIC 191' is a matrix of counters 760 that function as a digital pulse generator. This matrix of counters 760 include four delay and burst counters 764, four slow start/stop counters 765, and four phase counters 766. There is thus one counter of each type for each channel. In combination, the counters 760 define the parameters (timing and amplitude) associated with the stimulation pulses that are generated by the output current DACs 186' included within the analog ASIC chip 190' (see FIGS. 4B and 4C). Any combination of timing generators can drive any electrode through the analog ASIC chip 190'. An arbitrator circuit 768 monitors the various pulses being defined by the counters 760 in order to control overlap between pulses.

An output formatter circuit 767, which may also be referred to as a double buffer circuit, receives the pulse-defining data from the counters 760 and converts the output signals into two high-speed data buses 770 and 771. A first bus 771 contains the amplitude, mode and change data for the odd-numbered electrodes, e.g., electrodes E1, E3, E5, . . . E15. A second bus 770 contains the amplitude, mode and change data for the even-numbered electrodes, e.g., electrodes E2, E4, E6, E16. (Note, these two buses 770 and 771 are shown in FIG. 4B as a single bus 4C01.) The data carried on the buses 770 and 771 is applied to appropriate electrode latch circuits that define the control signals S1, S2 and S3 referenced in the block diagram of the analog ASIC 190' shown in FIG. 4B. Sync and clock signals, as well as a reset signal, are also sent from the digital ASIC 191' to the analog ASIC 190'.

A serial control circuit 772 also included as part of the digital ASIC 191' provides serial communications with the analog ASIC 190', and in the process provides additional timing and control information. Like all serial data transmissions, data bits are transmitted serially, one bit at a time, as enabled on a bit by bit basis. The data transmission rate is 1 million bits per second. Sample pulses, for use by the sample and hold circuitry 194' within the analog ASIC 190' are also sent to the analog ASIC via the serial control circuit 772. For example, a sample pulse may begin coincident with the start of a first phase on any of the four timing generators (counters) 766. The selection of the trigger source and time delay for the sample pulse may be based on the setting off of internal control registers. At the completion of the sampling pulse, an interrupt signal is generated for use by the processor IC 160'.

Returning again to FIG. 4B, the RF circuitry 172' includes antennas and preamplifiers that receive signals from the HHP 202 and provide an interface at adequate levels for the demodulation/modulation of the communication frames used in the processor 160'. Any suitable carrier frequency may be used for such communications. In a preferred embodiment, the frequency of the RF carrier signal used for such communications is 262.144 KHz, or approximately 262 KHz. A transmitter section receives digital transmit signals from the quadrature components, TxI and TxQ, of the data as generated on the 262 KHz carrier. The TxI and TxQ signals are coupled directly into the antenna during transmit. Additionally, the transmit section couples the antenna to the receiver during a receive mode. The transmitter section is responsible for antenna tuning and coupling while minimizing the processor noise to the RF signal.

A receiver portion of the RF circuitry 172' receives an incoming RF signal through a coupling circuit, amplifies the signal, and delivers it to a mixer located inside of the processor 160'.

The RF circuitry 172' also includes an antenna. The antenna, in a preferred embodiment, comprises a ferrite rod located in an epoxy header of the IPG case. The antenna makes electrical connection to the IPG circuitry via two feedthrough pins included within the header connector 192' (the other pins providing electrical connection to the individual electrodes located in the electrode array 110).

Still with reference to FIG. 4B, the Battery Charger and Protection Circuits 182' provide battery charging and protection functions for the Lithium Ion battery 180'. A charger coil 171' inductively (i.e., electromagnetically) receives rf energy from the external charging station. The battery 180' preferably has a 720 mWHr capacity. The preferred battery 180' has a life of 500 cycles over 10 years with no more than 80% loss in capacity. The battery charger circuits perform three main functions: (1) during normal operation, they continually monitor the battery voltage and provide charge status information to the patient at the onset of a communication link, (2) they ensure that the battery is not over-discharged, and (3) they monitor the battery voltage during a charging cycle to ensure that the battery does not experience overcharging. These functions are explained in more detail below in conjunction with FIGS. 9A, 9B and 9C.

The IPG 100' has three main modes that can initiate either a reset sequence or a hibernation state. The first mode is a hard power up reset that occurs at initial turn on. The second mode is a state where a fully functional IPG experiences battery depletion that may result in erroneous communication between the modules, thereby necessitating that the system power down in order to protect the patient. The third mode is a re-awake mode triggered from the depletion or hibernation state, which re-awake mode requires that the system perform self check and validation states.

A representative power-up reset sequence for the IPG 100' is illustrated in the flow diagram of FIG. 4D. As seen in FIG. 4D, and also with reference to the IPG elements shown in FIG. 4B, the process starts when an external charger is placed over the IPG (block 4D01). As the battery voltage rises above 2.5 or 2.6 volts, a charging current is detected (block 4D02). At this point, i.e., upon detection of the charging current, the battery protection circuit allows the battery to be connected to the analog IC 190' (block 4D03). Upon receipt of the battery voltage at the analog IC, the analog IC asserts the HEXTRESET line (high), starts generation of the supply voltage VDD, and starts a time delay for the HEXTRESET hold time (block 4D04). The voltage VDD tracks the battery voltage minus the regulator dropout. The HEXTRESET remains asserted until VBAT rises above 3.0 V and VDD is 2.7 V (block 4D05).

Next, the digital IC 191' resets all internal registers affected by the HEXTRESET signal (block 4D06). Then, the analog IC 190' similarly resets all registers affected by the HEXTRESET signal (block 4D07). When the battery voltage rises above 3.0 volts, the battery monitor circuit releases the HEXTRESET signal, allowing it to go low (block 4D08). At this point, the digital IC 191' is ready for commands from the processor IC 160' (block 4D09). Also, the analog IC 190' is ready for commands from the processor IC 160' via the digital IC 191' (block 4D10). The processor 160' next starts the reset sequence by fetching a RESET vector and jumping to the RESET routine (block 4D11). The boot loader routine then reads the data from the external SEEPROM memory 162' and stores the program and data section in the processor RAM (block 4D12). The processor, in response to such RAM-stored data, jumps to the internal program space and starts the system application code (block 4D13). The processor next initializes all the registers in the digital IC 191' and indirectly in the analog IC 190' to a safe state (block 4D14). The processor then verifies the system resources, including the battery status, the memory integrity, and all diagnostics (block 4D15). After such verification, the processor then sets the digital IC 191' and the analog IC 190' to default conditions (block 4D16). Next, the processor sets the remaining hardware resources to normal operating conditions (block 4D17). Finally, the processor executes the commands in the main idle and diagnostic loops (block 4D18).

The battery voltage of the IPG is monitored and, when it drops below a prescribed level, the IPG is taken through a slow shut down to a shutdown state via a series of intermediate steps as shown in FIG. 4E. Advantageously, in one embodiment, the IPG is capable of properly recharging a lithium-ion battery cell that has been completely discharged to zero volts. As indicated in FIG. 4E, the battery voltage is measured at a prescribed time interval, e.g., once every 4 hours, sixteen samples are taken, averaged, the value stored, so as to provide an indication of the normal operation of the system (block 4E01). The battery voltage and state are reported to the HHP 202 if the IPG is interrogated (block 4E02). Should the battery voltage fall below a minimum level, e.g., 3.6 V (block 4E03), then all parameter programming is disabled, and telemetry is limited to status and ID responses only (block 4E04). The IPG processor issues commands to halt all stimulation, updates the status register, and reports to the HHP when the IPG is interrogated (block 4E05). The IPG processor then makes a copy of the working registers, current stimulation parameters, digital IC settings, and CRC (error correction codes) in an appropriate memory location, e.g., in a SEEPROM memory (block 4E06). The battery voltage is then measured once every 10 minutes by taking sixteen samples, which are averaged, and the voltage is reported to the HHP if the IPG is interrogated (block 4E07). If the battery voltage falls below a first prescribed level, designated as VBAT (3.0±0.1 V), and if HEXTRESET is asserted, then all systems in the IPG are halted (block 4E08). Should the battery voltage fall below a second prescribed level, designated as the battery protection cutoff (2.5 V) (block 4E09), then the battery protection circuitry disconnects the battery from the main circuit (block 4E10). Note that the battery is not disconnected from the battery protection circuit, just from the main circuit. Although there may be a temporary battery voltage increase when the battery is first disconnected from the main IPG circuitry, the battery voltage will eventually continue to decrease at a slower rate. (Note: battery voltage decrease continues due to the small current needed to power the battery protection circuitry and battery self discharge.) When the battery voltage rises above 2.6 V, the protection circuitry reconnects the battery, and HEXTRESET is asserted (block 4E14). When the battery voltage rises above the VBAT threshold (3.0±0.1 V) (block 4E15), then HEXTRESET is released, and the process goes through the power-on-reset process (block 4E16). After the Power-On-Reset process, the battery voltage continues to be monitored every 10 minutes (block 4E07). When the battery voltage rises above the level to restore stimulation (3.8 V) (block 4E12), the stimulation is re-enabled, normal operation resumes, and telemetry is re-established for all command types (block 4E13). If the battery 180' comprises a non zero volt battery, and if the battery voltage falls below a third prescribed level, designated as the battery protection circuit minimum value (1.2 V) (block 4E11), then the battery is permanently disabled from the circuit, and the protection FET switches cannot be re-activated (block 4E17).

As indicated above, the processor IC 160' includes a ROM boot loader 735 (see FIG. 4B). A 1 Kbyte section of the Boot ROM 735 is organized as 512 words, located at FFC00 (HEX), consistent with the Intel specification for reset vectors used with an 8086 microprocessor. When a reset occurs, the processor begins execution at memory location FFFF0 (HEX). The instruction at this location causes a jump to the starting address within the boot space for the boot code. The boot code contains a program that loads further code from the serial boot SEEPROM 162' located off-chip. The processor Boot ROM flow chart is shown in FIG. 4F.

FIG. 4F shows that the following steps are performed during a ROM boot load: the CPU starts or is rebooted (block 4F01); the segment registers are reinitialized and power is shut off to unnecessary areas, and the watchdog circuit operation is acknowledged (block 4F02); a transaction begins with the offchip SEEPROM 162' to set the initial page address of a dummy write cycle (block 4F03); a determination is made as to whether the SEEPROM acknowledged (block 4F04); if acknowledgment occurred, then a transaction begins with the SEEPROM to begin a read transaction (block 4F05); a determination is made as to whether the SEEPROM acknowledged (block 4F06); if acknowledgment occurred, then a transaction begins with the SEEPROM wherein eight bits of data are read and placed in the offchip SRAM 163' (block 4F07). The first four bytes of data are used to specify the location in SRAM as well as the length of the program; a determination is made as to whether the SEEPROM acknowledged (block 4F08); a determination is made as to whether the code being read from the SEEPROM is finished (block 4F09) and if not, the code continues to be read 8 bits at a time (block 4F07); and then when all of the code has been loaded, a vector is formed that indicates where the code is loaded, and the processor jumps there to begin execution of the code (block 4F10).

As described above, it is thus seen that the implant portion 10 of the SCS system of the present invention (see FIG. 1) includes an implantable pulse generator (IPG) 100 as described in FIGS. 4A-4F. Such IPG includes stimulating electronics (comprising programmable current sources and associated control logic), a power source, and a telemetry system. Advantageously, the power source may be recharged over and over again, as needed, and may thus provide a long life, as well as a high current output capacity.

It is further seen that an important feature of the present invention is its ability to map current fields through selective control of the current sources which are attached to each electrode node. In one preferred embodiment, the invention achieves its desired function of being able to independently map a desired current to each electrode node through the use of a processor 160', one or more ASIC's 190' or 191', sixteen independent bi-directional output current DACs (FIG. 4C, elements 4C05-4C07), and timers and control registers, configured to operate in a state machine architecture. The ASIC has a standard bus interface to the microcontroller allowing simple, direct and efficient access to all of its control and stimulation parameter registers. Triggering and timing control circuitry allow the simultaneous activation of any of the channels. In one embodiment (FIG. 4A), a low impedance switching matrix advantageously allows the mapping of each current generator's two outputs to be assigned to any of the pulse generator electrode nodes (or leadwires, which are attached to the electrode nodes) or to the case. In a preferred embodiment (FIGS. 4B and 4C), there is no need for a low impedance switching matrix. Rather, independent bi-directional current sources for each of the sixteen electrodes (independently operable output current DACs) allow the output currents to be mapped to any of the output electrode nodes or to the case. In this manner, one or more current generators may be attached to any one or more electrode nodes (leadwires) and thus electrodes, and conversely, any electrode node (leadwire) may be attached to one or more current generator outputs, grounded, or left open. The significance of the biphasic, or (in some instances) multiphasic, nature of the stimulation pulses is that currents may be actively driven in either the anodic or cathodic direction to the output electrode nodes of the current generators. This feature, along with the matrix switching of output leads, or independently operable output current DACs, depending upon the embodiment used, allows the creation of "virtual" electrodes and stimulation current field control, not possible with other known designs. This feature thus provides an important advance in the ability to direct the stimulation pulses to pools of target neurons in the spinal cord.

In use, the IPG 100 is typically placed in a surgically-made pocket either in the abdomen, or just at the top of the buttocks, and detachably connected to the lead system (comprising lead extension 120 and electrode array 110). While the lead system is intended to be permanent, the IPG may be replaced should its power source fail, or for other reasons. Thus, a suitable connector, e.g., the snap-on tool-less connector disclosed in U.S. patent application Ser. No. 09/239,926, filed Jan. 28, 1999, now U.S. Pat. No. 6,198,969, or other suitable connectors, may advantageously be used to make the connection between the lead system and the IPG 100.

Once the IPG 100 has been implanted, and the implant system 10 is in place, the system is programmed to provide a desired stimulation pattern at desired times of the day. The stimulation parameters that can be programmed include the number of channels (defined by the selection of electrodes with synchronized stimulation), the stimulation rate and the stimulation pulse width. The current output from each electrode is defined by polarity and amplitude. Additionally, as indicated above, a run schedule may be downloaded and stored in the memory of the IPG 100, which when used enables the IPG only at programmed times of the day.

The back telemetry features of the IPG 100 allow the status of the IPG to be checked. For example, when the external hand-held programmer 202 (and/or the clinician programmer 204) initiates a programming session with the implant system 10 (FIG. 1), the capacity of the battery is telemetered so that the external programmer can calculate the estimated time to recharge. Additionally, electrode impedance measurements are telemetered at the beginning of each programming session, or as requested. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

Figure 5:
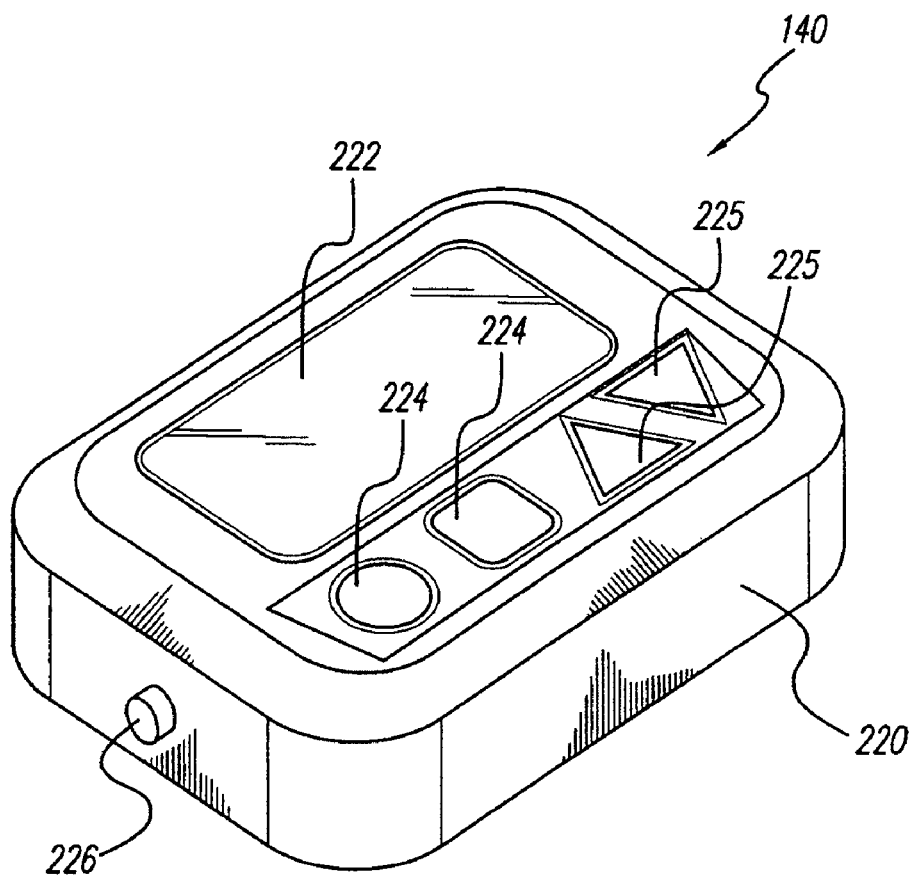
FIG. 5 illustrates a type of external trial stimulator (ETS) that may be used as a component of the invention.

Turning next to FIG. 5, one type of external trial stimulator (ETS) 140 that may be used as a component of the invention is illustrated. As explained previously in connection with FIG. 1 and FIG. 2B, the ETS 140 connects to the electrode array 110 through a percutaneous extension 132 and an external cable 134. Because of this percutaneous, or "through-the-skin" connection, the trial stimulator 140 is also referred to as a "percutaneous stimulator" 140. The main purpose of the ETS 140 is to provide a 2-7 day stimulation trial with the surgically placed electrode array 110 before implanting the IPG 100.

As seen in FIG. 5, the ETS 140 is housed within a hand-held case 220. Displayed on the case 220 are a set of intuitive control buttons 224, 225 that control the operation of the device. Advantageously, these control buttons are the same as, or very similar to, the types of buttons found on the patient hand held programmer, or HHP (explained below). A cable contact port 226 having a multiplicity of contacts, e.g., 16 contacts, is provided on one side of the device into which the external cable 134 and/or percutaneous extension 132 may be detachably connected. Typically, during implant of the electrode array, when the ETS 140 is under control of a surgeon, the ETS 140 is connected to the electrode array 110 through the external cable 134 (see FIG. 1) and the percutaneous extension 132. Then, after implant, during a trial period when the stimulator 140 is under control of the patient, the trial stimulator 140 is connected to the electrode array 110 directly through the percutaneous extension 132. In other words, once the patient leaves the operating room (OR), there is generally no need for the external cable 134.

Figure 2B:
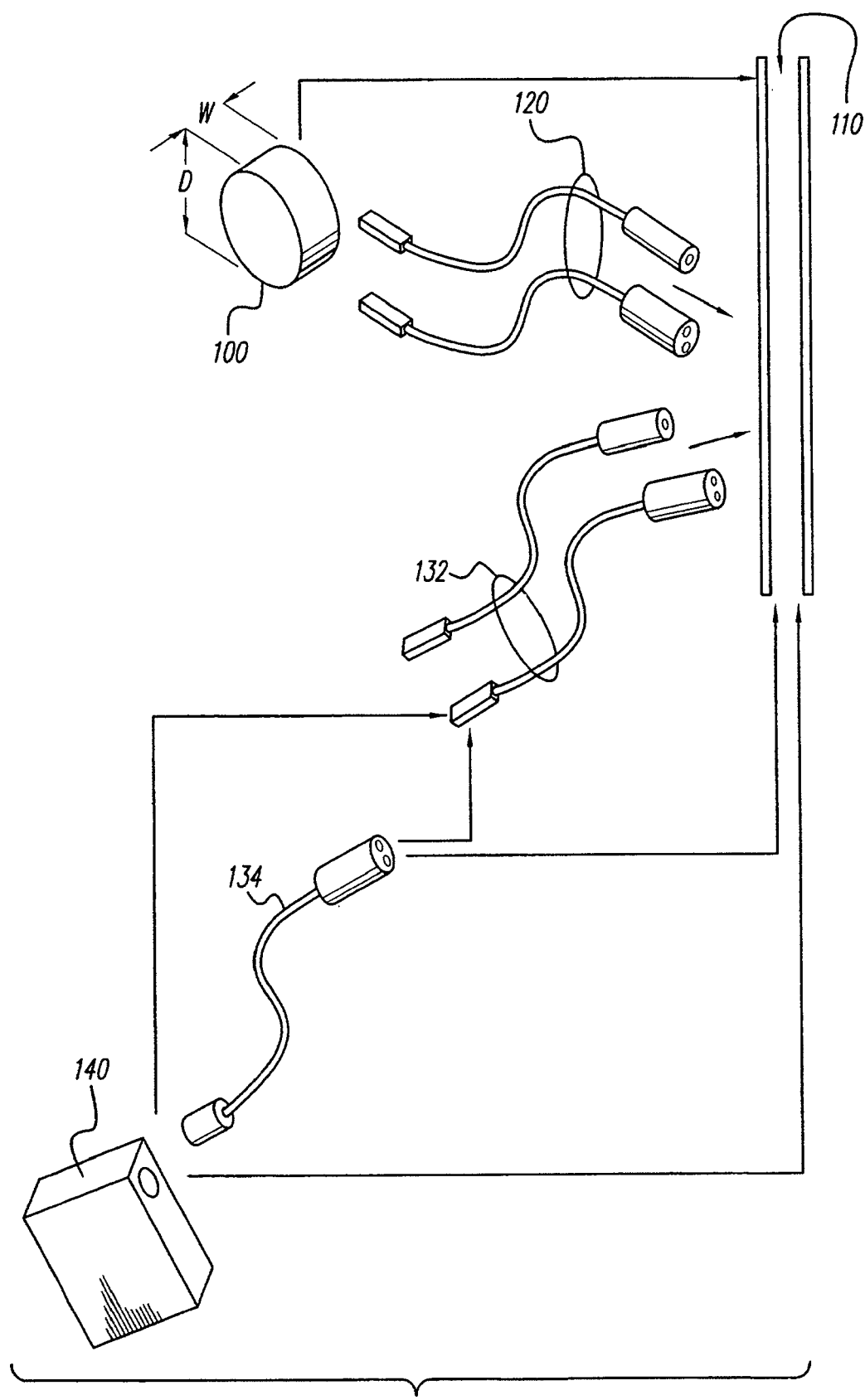
FIG. 2B shows the various components of the invention that interface with the implantable electrode arrays of FIG. 2A, or other arrays.

As seen in FIGS. 1 and 2B, the percutaneous extension 132 is a temporary lead extension that is used to connect the electrode array 110 to the external trial stimulator 140 and/or external cable 134 during the trial period. This lead is positioned by the surgeon using suitable tunneling tools 152 to create a tunnel between the array 110 and the percutaneous exit site. Once the tunnel is made, the percutaneous extension is pulled through for connecting to the array. The exiting end of the percutaneous extension may then be connected to either the trial stimulator port 226 or the external cable 134.

The percutaneous extension 132 is typically 30 cm in length and no greater than 3 mm in diameter (when it connects with a single-8 electrode array, e.g., an in-line electrode having 8 electrode contacts, or an electrode of the type shown in FIG. 2A(G)), or no greater than 4 mm in diameter (when it connects with a dual-8 electrode array, e.g., an electrode of the type shown in FIG. 2A(E)).

The external connectors used on the external cable 134 and the percutaneous extension 132 are easy to connect and disconnect into their mating connectors or plugs. More than one external cable 132 may be provided, as needed, e.g., of differing lengths, in order to allow the trial stimulator to be moved around the operating table. Such cables, of course, must be sterilized for use within the OR.

The external trial stimulator (ETS) 140 has circuitry that allows it to perform the same stimulation functions as does the IPG 100. Further, the circuitry within the external trial stimulator 140 allows it to receive and store programs that control its operation through a suitable telecommunicative link 205 (FIG. 1) established with the clinician programmer 204. Thus, with such link 205 established, the clinician programmer 204 may be used to program the external trial stimulator 140 in much the same way that the clinician programmer is used to program the IPG 100, once the IPG 100 is implanted. Advantageously, the link 205 is bi-directional, thereby allowing programming data sent to the stimulator 140 from the clinician programmer 204 to be verified by sending the data, as stored in the stimulator 140, back to the programmer 204 from the ETS 140. In one embodiment, the link 205 comprises an infra-red (IR) link; in another embodiment, the link 205 comprises a cable link. The link 205 is preferably functional over a distance of at least 7 feet, thereby allowing the trial stimulator to be easily used in an operating room (OR) environment.

The external trial stimulator 140 further includes limited programming functions that allow some modification of some of the programmable values using the control buttons 224 and 225. A flat display screen 222 on which programming or other information may be displayed is also provided. Typically, the screen 222 is used to show programmable values as they are selected and/or modified. A hidden physician access screen may also be displayed on the stimulator screen 222 when enabled. This allows the physician to verify programming and patient data, as well as to check the status of the operating condition of the stimulator.

Advantageously, the external trial stimulator 140 is compact in size, and can be easily held in one hand. To make it even easier to carry, especially by the patient, a belt clip is placed on its back side, thereby allowing it to be worn on a patient belt, much like a pager or cell-phone. The device case includes an accessible battery compartment wherein replaceable (and/or rechargeable) batteries may be carried having sufficient capacity to provide operating power to both its internal pulse generator circuitry and programming electronics for at least one week.

The external trial stimulator 140, or ETS, is first used in the operating room (OR) to test the electrodes of the electrode array 110 during placement of the electrode array. During such OR use, it is critical for the surgeon to quickly access and adjust amplitude, pulse width, rate, channel and electrode selection without having to switch back and forth between screens or scroll through each parameter. Immediate access to the pulse amplitude and the electrode to which the pulse is applied are most important. The communication link 205 established between the stimulator 140 and programmer 204 greatly facilitate such quick access.

Once the electrodes have been tested with the external trial stimulator 140 in the OR environment immediately after implant, and the surgeon is satisfied that the trial stimulator has been programmed in an acceptable manner and is functioning properly, the ETS 140 is then used by the patient during a trial period, e.g., of from 2-7 days. During this time, the patient may perform limited programming of the stimulator 240, e.g., to set the channel, amplitude, rate and on/off programming functions.

Next, the clinician programming system will be described. This system includes, as seen in FIG. 1, a clinician programmer 204 coupled to a directional device 206. The clinician programmer 204 typically interfaces with the patient hand-held programmer 202 in communicating with the implanted pulse generator (IPG) 100. As described above, the clinician programmer 204 may also be selectively coupled to the external trial stimulator 140.

The clinician's programming system is used to optimize the programming of the implant for the patient. In a preferred implementation, such system comprises software, referred to as Clinician's Programmer Software (referred to as "ClinPro" software) with operates on a 32 bit Windows operating system. The function of the ClinPro software is to program the IPG. Programming the IPG involves setting the pulse width, amplitude, and rate through which electrical stimuli are to be applied to the patient through the selected combinations or groups of electrodes on the electrode array 110 (FIG. 1). As such, any software or other programming means could be used to achieve this programming purpose. The description of the ClinPro software that follows is provided solely to provide an overview of the preferred software used for this IPG programming purpose. Further details associated with programming the IPG may be found in U.S. Pat. No. 6,052,624; U.S. patent application Ser. No. 09/550,217, filed Apr. 17, 2000, (now U.S. Pat. No. 6,393,325); and U.S. Patent Application No. 60/172,167, filed Dec. 17, 1999; which patent and applications are incorporated herein by reference. The details associated with the ClinPro software are not presented herein because such details are not viewed as a critical part of the invention.

The ClinPro software is used on a conventional personal computer, PC, e.g., a laptop or notebook computer, programmed with a 32-bit Windows operating system, such as Windows98 or Windows2000. The ClinPro software in combination with the hardware on which it is used is referred to as the "ClinPro system."

Figure 6A:
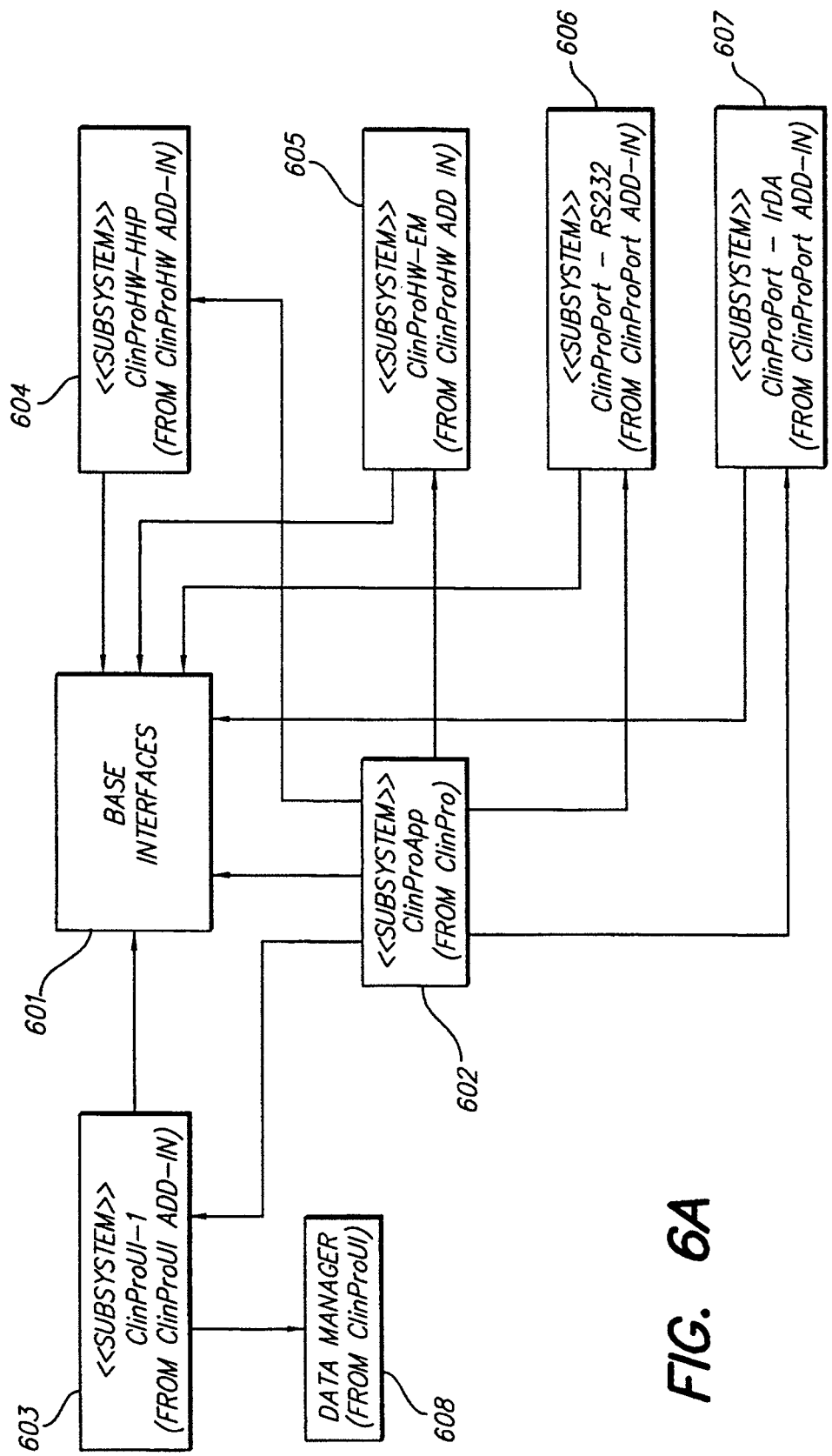
FIG. 6A is a block diagram of the software architecture utilized in the clinician's programmer.

A block diagram of the ClinPro system is shown in FIG. 6A. As seen in FIG. 6A, The ClinPro system consists of several subsystems (add-ins) that interact with each other. The add-ins are separate and independent of each other. The only way the different add-ins communicate with each other is through well defined base interfaces 601. An interface is a protocol that defines properties and methods that can be performed on a component. For one add-in to interact with another add-in, the first add-in must use the interface provided by the second add-in, and vice-versa. Advantageously, this provides the ability to develop new add-ins without affecting the existing add-ins. The add-ins register themselves in the operating system registry when installed.

As shown in FIG. 6A, the ClinPro system contains only one subsystem of the ClinProApp type 602, and one or more of other types of subsystems like the User Interface subsystem 603, the Hardware subsystems 604 and 605, and the Port subsystems 606 and 607. Each subsystem type has a certain basic functionality that it provides to the ClinPro system.

The user interface subsystems 603 provide access to the user interface (UI), e.g., data-entry forms through which the user provides information to the program, and also encapsulate the data access functionality. The UI subsystem provides an interface that provides access to the patient information maintained in a data manager 608. Other subsystems, including the ClinProApp 602, must use the user interface 603 to access the patient information contained in the data manager 608.

The hardware subsystems 604 and/or 605 provide command generation and interpretation for the specific hardware they encapsulate. The hardware subsystems use the port subsystems 606 and/or 607 to communicate with the physical hardware. The hardware subsystems expose functionality specific to the hardware (e.g., Set Amplitude, Set Pulse Width, etc.) through the base interface 601 to the rest of the system. This interface is used by the corresponding UI subsystems 603 to change the hardware settings.

The port subsystems 606 and/or 607 provide access to the physical ports on the system, e.g., an RS-232 port or an infrared port. They expose functionality to enumerate available ports, open, read, write and close a specific port. The port subsystems are typically used by the hardware subsystems. Other special subsystems (e.g., a terminal emulator subsystem) may use the port subsystem for diagnostic purposes.

The advantage of using the type of architecture shown in FIG. 1 is that it provides the system the ability to develop new functionality as a new subsystem and then integrating it into the existing system without modifying the existing subsystems. For example, after the initial software is shipped and installed at a site, a second user interface add-in can be developed independently and shipped to the site and installed without any modification to the existing subsystems. The same holds true for hardware subsystems as well. The existing user interface subsystem will communicate with the new hardware subsystem or as long as the new hardware subsystem implements the previous hardware subsystem's interface.

The ClinPro application 602, FIG. 6A, manages the creation and usage of the different add-in objects. Each add-in implements an interface that provides the add-in name, type, etc. The application uses this interface to get information from an add-in. The application also provides its own interface to the add-ins for getting the active hardware, active port, etc. For example, when the UI interface 603 add-in wants to send information to the hardware, it first gets the active hardware from the application and then calls the corresponding method exposed by the interface of the hardware add-in.

The user interface add-ins 603 implement the user interface for taking patient threshold measurements, generating reports and implementing other functionality. The UI also implements a user interface to provide access to the patient information, program information, measurement information, etc. from the database 608 and the Add-in interface. The UI add-ins reference the application interface to get active hardware, and the hardware interface to set the different parameters.

The hardware add-ins implement the functionality provided by the hardware. This includes setting amplitude, pulse width, rate, etc. The hardware add-ins implement the add-in interface and a hardware interface to expose methods to set the amplitude, pulse width, rate, etc. The hardware add-ins reference the application interface to get available ports to poll for hardware, set the active port, etc. They also reference the port add-in interface to transmit and receive data from the physical hardware.

The port add-ins implement the functionality to access the I/O ports in the system. This includes opening and closing a port, reading and writing to a port, etc. The port add-ins implement the add-in interface and a port interface which exposes methods to change port settings, open a port, close a port, write to a port, read from a port, etc.

Figure 7E:
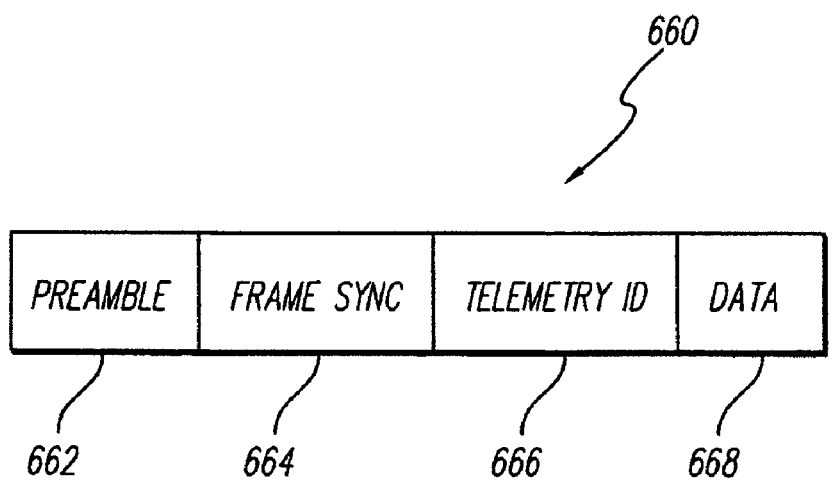
FIG. 7E depicts a preferred data format for data communications sent from the hand held programmer (HHP) to the IPG.

The clinician programmer 204, including the ClinPro system, is configured to talk to the IPG 100 via the hand-held programmer 202. In a preferred implementation, the ClinPro application is installed on a notebook or laptop computer running the Windows98 operating system. The computer is connected to the HHP 202 through an IrDA compatible infra-red serial port using an infra-red cable extension. The HHP 202 is then connected to the IPG using radio frequency (RF) communications. While any suitable communications protocol could be used for such RF communications, a preferred communications format is shown in FIG. 7E, described below.

Thus, the ClinPro system, with its various add-in subsystems or modules, maintains a patient data base, and is able to program all features of the implant in a simple and intuitive manner. Additionally, the system allows threshold measurements to be made, operational electrodes to be identified, and is able to interface directly with the patient.

A key feature of the ClinPro system is to include a joystick accessory, or equivalent directional device 206 (FIG. 1). Such device, coupled with appropriate add-in subsystem software, allows the patient to interface with the clinician programmer 204, external trial stimulator 140, or other processor (e.g., a hand-held computer, such as a PalmPilot® computer, or equivalent) so as to allow the patient, or other medical personnel assisting the patient, to configure electrodes and adjust various stimulation parameters. This directional programming is described in more detail in U.S. Pat. No. 6,052,624, entitled "Directional Programming for Implantable Electrode Arrays", incorporated herein by reference. As described in the '624 patent, such directional programming may advantageously be performed both in the OR environment and in the doctor's office. The clinician or nurse simply operates the joystick feature, or equivalent directional programming feature, during surgery in conjunction with the trial stimulator so as to configure and select the electrodes that provide stimulation. The patient may then use the joystick feature to finalize the device programming during a post implant adjustment session. Thus, whether communicating with the external trial stimulator 140 or with the IPG 100 through the HHP 202, the directional programming device 206 is able to be effectively used to configure which electrodes provide stimuli to the patient.

In the preferred embodiment, the Clinician's programming system is thus designed to operate as windows compatible software. It is user friendly and may provide (in some versions) automated patient fitting and virtual electrode directional programming. It is capable of maintaining a patient data base and graphic reports. It also provides, through calculations based on measurements made, an automatic estimate of the implant battery capacity.

In operation, as seen in FIG. 1, the clinician programming system communicates to the patient programmer 202 over a telecommunicative or other communication link 203, which then telemeters the data to the IPG 100. Likewise, the clinician's programmer is able to communicate to the external trial stimulator 140 over the telecommunicative link 205. The communication links 203 and 205 are reliable links capable of operating in the busy OR environment. Data speeds to and from the IPG 100, through the patient programmer 202 intermediary link, are fast enough to not noticeably delay programming. A communication link status between devices is always depicted on a screen, or other display device, associated with the programmer 204.

As soon as the clinician programmer is initially connected to the implant system, hardware recognition occurs. That is, the system identifies the stimulator, the patient programmer, and electrode availability (through electrode impedance measurements).

For safety, the patient programmer 202 is coded to work only with a specific implant system. Should the patient lose his or her programmer 202, then the physician, using the clinician programmer, is able to code a new programmer for use with the patient's implant system. The clinician's programmer, in contrast, is able to communicate to any implant through any programmer 202 by using an overriding universal code. This allows the patient code to be extracted from the IPG 100 and used to re-code a new programmer 202.

When an IPG 100 is in contact with a clinician programmer 204, the device settings and hardware information (model, serial number, number of electrode by impedance, and the like) are first uploaded to the SCS add-on programming software in the clinician programmer 204. All devices in the link with the IPG, e.g., the hand held device 202, and/or the trial stimulator 140, and clinician programmer 204, and the clinician programmer 204, are synchronized so that each device receives accurate and current data. Programming changes made to the stimulator(s) are confirmed through back telemetry or other means before the SCS add-on software reflects the change. Advantageously, the physician is able to program the stimulator through either the patient programmer 202 or the clinician programmer 204 while linked together through the link 203, with all programming changes being mirrored in both devices.

Various programming features of the ClinPro software make the programming system extremely user friendly. In the preferred embodiment, these programming features include at least the features described below.

A patient information window is accessible through the programming system that allows either a new patient or an existing patient file to be created or opened. Such patient file is presented as a blank or existing window, including a series of tiered sub-windows, including: "patient information," "appointment," and "case history". Selecting a new patient places the "patient information" window at the top tier for data entry. Selecting from patient files places "appointment" window at the top tier. The patient name is automatically written on all patient file windows. When the system detects an implant serial number that matches a patient file, that patient file is automatically opened and displayed as a starting point.

The "patient information" window includes entry fields for last name, first name, birth date, and a patient identification number. A drop down menu provides a list of patient diagnosis that can be entered, i.e., nerve injury, Sciatica, Arachnoiditis, and the like. Also included is a listing of the patient's hardware, which is entered automatically based on the hardware that is detected when the devices are linked.

The "appointment" window displays the patient's name and hardware, and further includes entry fields with drop-down selections for diagnosis, reason for visit (e.g., trial, implant, replacement, programming, and the like), and a notes field.

The "case history" window presents a figure of the human body, or portions of the human body, on which are illustrated the pain sites that have been treated in the past, and a chronology of the patient appointment dates. Selecting a patient appointment date causes the stimulation programs, illustrations and notes that were applied on that date to be displayed. These case history files may not be altered through normal means, but are rather intended to be saved as permanent archived files.

Various patient-specific reports may be generated by the system. These reports when generated may be printed, faxed, saved to a file, or sent via email to a designed location. The reports include, as a header, the logo or other identification of the clinic were created, the patient's name, birth date and implant type. The body of the reports may include: (1) patient information, i.e., the information captured in the patient information windows; (2) the patient visit history, i.e., a list of dates the patient visited the clinic with reasons for the visit, the type of hardware used by the patient, and the implant serial number; (3) the program report, i.e., the details of those programs used by the patient to provide stimulation, the electrode configuration, and the like; (4) the measurement history, i.e., a graphical and/or tabular representation of the measurements (bipolar and/or monopolar threshold and maximum levels) for each electrode. Typically this is done in one or a series of graphs or tables with the electrode being displayed on the x-axis, and the measurement unit on the y=axis; and (5) a stimulation evaluation, i.e., a paresthesia/pain illustrative representation.

The ClinPro programming software further provides a programming window that facilitates programming the stimulator. The programming window, in one embodiment, includes at least three tiered sub-windows, which may be titled, e.g., "measurements", "programming", and "advanced". The programming window is advantageously accessible from both a main menu and a patient information window.

Figure 6B:
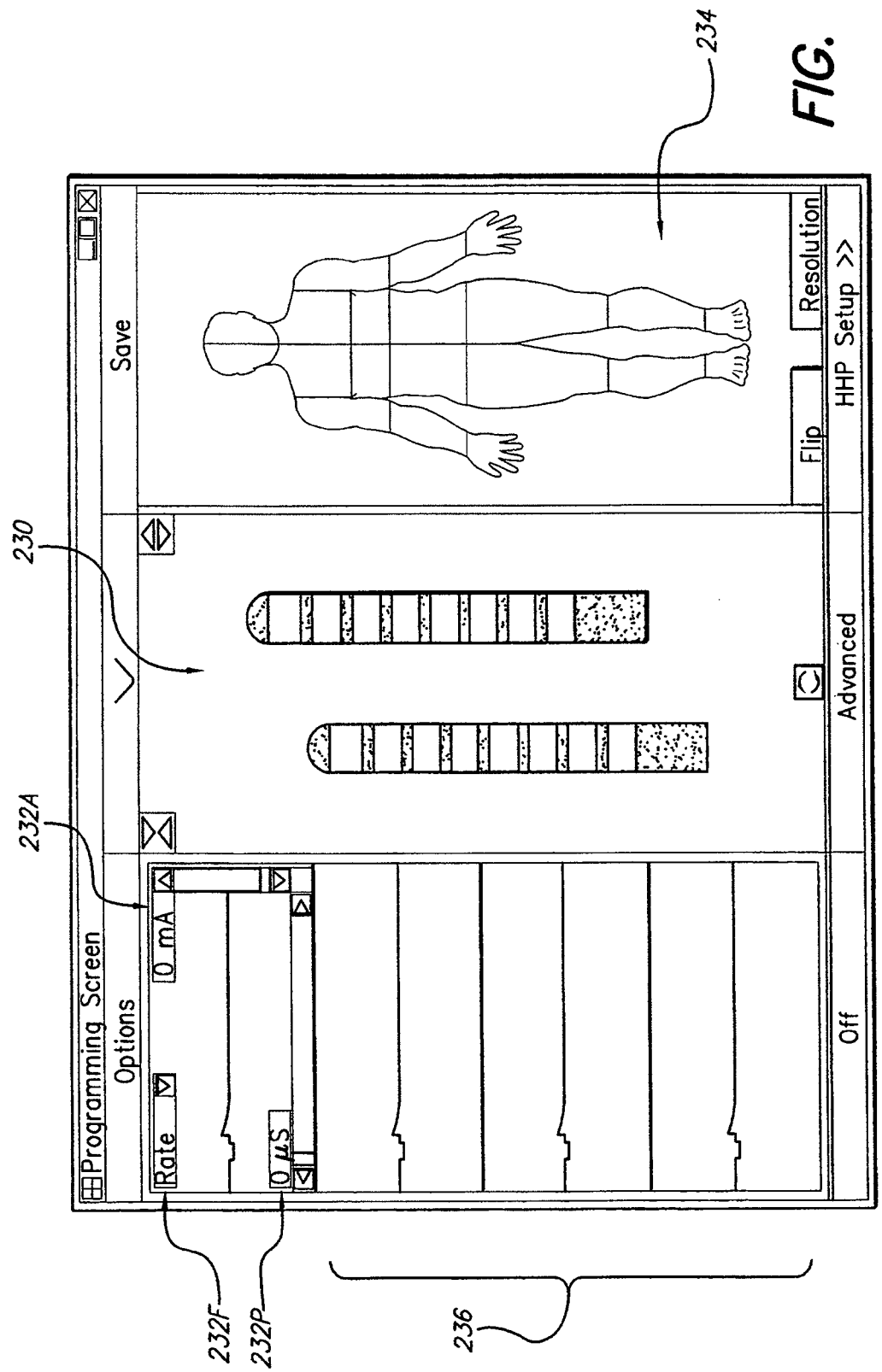
FIG. 6B depicts a representative programming screen that may be used as part of the programming system features of the invention.

The measurement window, which may also be referred to as a "threshold" window, is used to set maximum and minimum thresholds, and to map pain and paresthesia with implanted electrodes to anatomical sites. A representative measurement window is illustrated in FIG. 6B. (In practice, there may be more than one window, each featuring a different measurement or setting.) As seen in FIG. 6B, included in the display of the measurement window is a representation 230 of the type and orientation of the electrode array(s) that has been selected. Such selection is made from a group of possible electrode choices. Monopolar and bipolar sensitivity (max and min) thresholds may then be determined for each electrode for the displayed electrode array configuration, with the aid of amplitude, rate (frequency), and pulse width settings 232A, 232F and 232P, respectively. In one embodiment, maximum and minimum thresholds map to amplitude levels designated by numbers from 1 to 10 for each electrode (with respect to monopolar or bipolar or multipolar configurations), as described in U.S. Patent Application Ser. No. 60/172,167, filed Dec. 17, 1999, incorporated herein by reference. Pain and/or paresthesia mapping is available to identify electrode effects through the threshold testing process. To aid in this process, a human FIG. 234 is displayed and divided into sections for selection.

In use, a pain or paresthesia is activated by toggling a color box, i.e., red or blue, that is superimposed over the affected body area. One color, e.g., red, represents pain; while the other color, e.g, blue, represents paresthesia. As the mouse pointer passes over different body segments, such segments change color to the active color and can be locked to the active color by clicking the mouse. The paresthesia color is always transparent (top layered) so that pain segments can be seen. Multiple body segments can be selected individually, or as a group at intersections. By clicking on a segment a segment, the active color is toggled off and on without affecting the alternate color. The object is to match or map the paresthesia segments with the pain segments. Such pain/paresthesia mapping feature may be used with expert algorithms to automate the programming process. Alternatively, the patient and clinician/physician may simply work together and use a trial-and-error procedure in order to best fit the paresthesia segments with the pain segments.

Programming window screen(s) is/are accessible from at least a patient information window and a main menu. The programming screen is used to program electrode configurations and the desired output parameters for each of the available channels. Representative current stimulus waveforms for selected electrodes are displayed in area 236 of the screen shown in FIG. 6B. Once selected, continual clicking of the selected electrode group toggles stimulation between active ON and PAUSED, with a settable slow start/end. The slow start/end feature is explained in more detail below. Selection of another electrode channel does not change any of the settings of a previous channel.

Before electrodes are displayed on the screen for programming, the array type and orientation must be selected. The number of implanted and available electrodes is typically automatically determined by impedance measurements during hardware interrogation. Pointing to the electrode box 230 provides an electrode array selection, based on the number of detected electrodes, with preset visual forms. Once the array configuration is selected, it is displayed on the screen with point and click selectable electrodes. For example, one click specifies a cathode; two clicks specifies an anode; and a third click specifies a neutral (floating or non-connected) electrode. Cathode, anode and neutral selections are indicated by a color change. By clicking an electrode to a cathode or anode state, the electrode is assigned to the active channel. If desired, a representation of current fields created by electrodes of a channel may also be displayed within this representation.

The amplitude, pulse width and rate are adjustable by mouse or arrow keys for the selected channel, using e.g., the "channel settings" area 232A, 232F and 232P of the programming screen. Amplitude, on this main programming screen, is programmable by channel, and applied as a distribution between maximum and sense thresholds for a group of assigned electrodes. The amplitude for the group may be selected as a level from 1-10, where a "1" represents the sense threshold for each electrode in the group, and a "10" represents the maximum threshold. The pulse width and rate are also selectable for the group, and applied to the group-assigned electrodes. Although the programming software permits a physician to program electrodes by group, each electrode is individually controlled by the implant, and telemetered data is electrode specific. When a group is programmed to stimulation rates over 150 pps, the number of additional groups may be limited (due to battery capacity). A toggle lock/unlock button for each parameter allows the programming physician to set which parameters are available within the hand-held patient programmer (discussed below in conjunction with FIGS. 7A-7E).

In one embodiment, the settings for up to four electrode groups are referred to as a "program." Selectable default parameter settings may thus comprise a program. A store/apply button records all the settings with a program number. Up to twenty programs can be named, stored and selected form a drop-down program list. Thus, programs may be sequentially or selectively tried by the patient so that the patient may compare how one "program" feels compared to another.

Changes in programming are duly considered relative to the estimated effect they will have on a projected battery discharge cycle. Should a programming change fall below a two day recharge and/or less than a three year expected life, or other set times, a pop-up window appears with suitable warnings and possible recommendations. As needed, an emergency off button turns all stimulation OFF, with direct keyboard and mouse click access.

It is thus seen that the programming window(s) allows the output parameters for each channel to be programmed with additional capability and specificity. For example, biphasic verses passive balance pulses, active multipolar driving of cathodes and anodes (field focusing), and amplitude selection for individual electrodes.

Unique programming algorithms may also be employed which provide, e.g., automated and directional programming features. Automated programming may be used, e.g., to use known thresholds and pain/paresthesia mapping to recommend configurations and parameters based on preset rules and database information. Automated programming maps paresthesia sites over pain sites. Directional programming features may be as disclosed in U.S. Pat. No. 6,052,624, previously referenced. Such directional programming uses a joystick, or other means, to configure electrodes within certain limitations for selection, polarity, and amplitude distribution in response to a directional input and in an intuitive and physiologic manner.

Advantageously, as previously indicated, the programming software used within the clinician programmer 204 (FIG. 1), whether the referenced ClinPro software or other suitable software, may run under conventional operating systems commonly used within personal computers (PCs). The preferred clinician programmer is a Pentium-based PC, operating at 100 MHz or more, with at least 32 Mbytes of RAM. Examples of an operating system for use in such a system include Windows98, Windows2000 or Windows NT 4.0/5.0. Such programming software also supports multiple languages, e.g., English, French. German, Spanish, Japanese, etc.

Figure 7A:
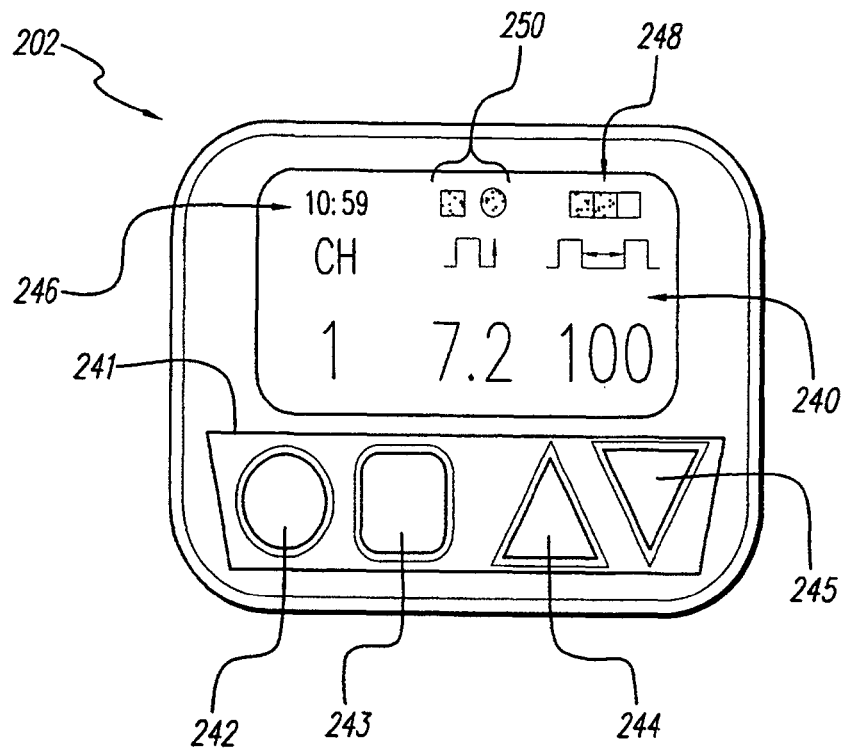
FIG. 7A shows a representative screen on a handheld programmer (HHP) that may be used as a user interface between the HHP and the IPG implanted in a patient/user.
Figure 7B:
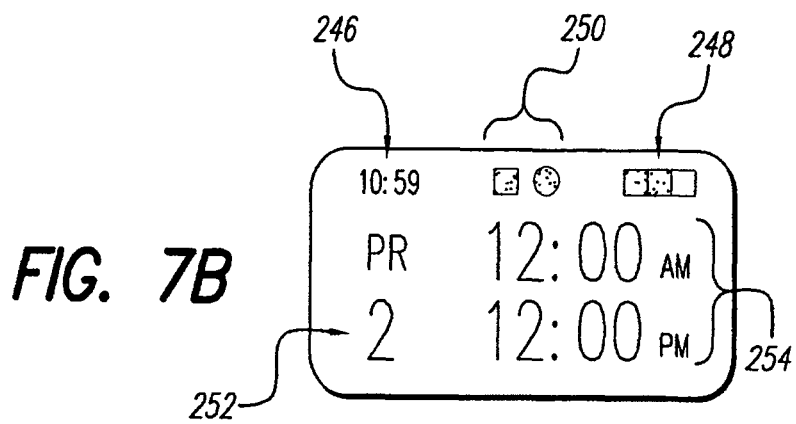
FIGS. 7B and 7C illustrate other types of representative selection screens that may be used as part of the user interface with the handheld programmer of FIG. 7A.
Figure 7C:
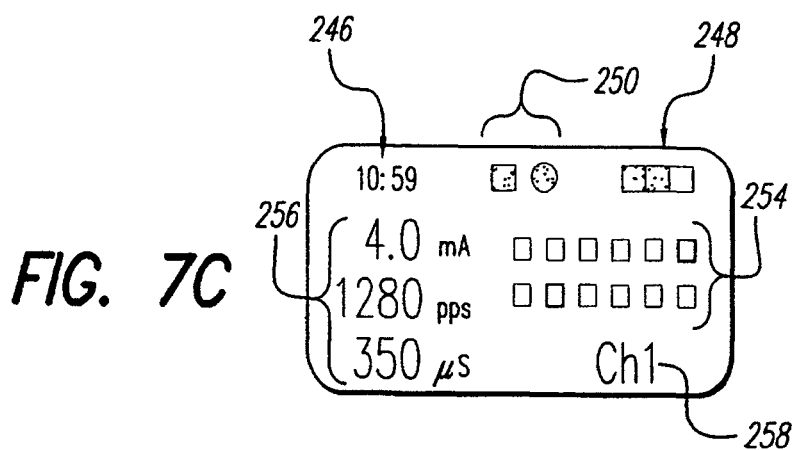

Turning next to FIGS. 7A, 7B and 7C, a brief description of the patient handheld programmer (HHP) 202 will be presented. As described previously, the patient HHP 202 comprises an RF handheld battery-operated device that communicates with the IPG 100, the external trial stimulator 140, or the clinician programmer 204. Advantageously, the electrical circuitry and user interface of the patient handheld programmer 202 provide limited parameter control that is simple, intuitive and safe. The programmer 202 is compact in size, includes a lighted flat panel display screen 240, and allows a plurality of separate programs to be stored therein. The screen 240 may display programming information for the patient; or may display a "physician access screen" which is normally hidden to the patient. It operates using replaceable and/or rechargeable batteries, and preferably has an operating range of about one-to-two feet or more with the IPG 100, and of at least 7 feet from the clinician's programmer 204. All programming systems (those used within the handheld programmer 202 and within the clinician's programmer 204) are always appropriately synchronized (or otherwise coordinated with each other) so that any changes from one are reflected in the other.

A representation of one embodiment of the HHP 202 is shown in FIG. 7A. As seen in FIG. 7A, the HHP includes a lighted display screen 240 and a button pad 241 that includes a series of buttons 242, 243, 244 and 245. (The number of buttons shown in FIG. 7A is exemplary only; any number of buttons may be employed, and in fact in a second preferred embodiment five buttons are employed.) The buttons provided within the button pad 241 allow the IPG to be tuned ON or OFF, provide for the adjustment or setting of up to three parameters at any given time, and provide for the selection between channels or screens. Some functions or screens may be accessible by pressing particular buttons in combination or for extended periods of time. In a preferred embodiment, the screen 240 is realized using a dot matrix type graphics display with 55 rows and 128 columns.

The button pad 241, in a preferred embodiment, comprises a membrane switch with metal domes positioned over a flex circuit, which bonds to the top housing of the HHP. A keypad connector connects directly a printed circuit board (PCB) of the HHP, and the bonding to the housing seals the connector opening.

In a preferred embodiment, the patient handheld programmer 202 is turned ON by pressing any button, and is automatically turned OFF after a designated duration of disuse, e.g., 1 minute. One of the buttons, e.g., the IPG button 242, functions as an ON-OFF button for immediate access to turn the IPG on and off. When the IPG is turned ON, all channels are turned on to their last settings. If slow start/end is enabled, the stimulation intensity is ramped up gradually when the IPG (or ETS) is first turned ON with the HHP. When the IPG is turned OFF, all channels are turned off. If slow start/end is enabled, the stimulation intensity may be ramped down gradually rather than abruptly turned off. Another of the buttons, e.g., the SEL button 243, functions as a "select" button that allows the handheld programmer to switch between screen displays and/or parameters. Up/down buttons 244 and 245 provide immediate access to any of three parameters, e.g., amplitude, pulse width, and rate.

Also included on the screens shown on the display 240 of the handheld programmer 202 are status icons or other informational displays. A battery recharge countdown number 246 shows the estimated time left before the battery of the IPG needs to be recharged. A battery status icon 248 further shows or displays the estimated implant battery capacity. This icon flashes (or otherwise changes in some fashion) in order to alert the users when a low battery condition is sensed. Every time the patient programmer is activated to program or turn on the IPG, the actual battery status of the implanted pulse generator (IPG) is interrogated and retrieved by telemetry to reconcile actual verses estimated battery capacity. Other status icons 250 are provided that display the status of the patient-programmer-to-implant link and the patient-programmer-to-clinician-programmer link.

As a safety feature, the physician may lock out or set selectable parameter ranges via the fitting station to prevent the patient from accessing undesirable settings (i.e., a lockout range). Typically, locked parameters are dropped from the screen display.

The main screen displayed by default upon activation of the handheld programmer 202 shows amplitude and rate by channel, as illustrated in FIG. 7A. As shown in FIG. 7A, the display is for channel 1, the amplitude is 7.2 ma, and the rate is 100 pps. Thus, it is seen that the channel number (or abbreviated channel name as set by the clinician programmer) is displayed on the screen with the parameters. Amplitude is the preferred default selection (i.e., it is the parameter that is displayed when the unit is first turned ON).

Whenever a displayed parameter is changed, the settings of the IPG 100 are changed via telemetry to reflect the change. However, in order to assure that the IPG has received the telemetry signal and made the corresponding change without a discrepancy between the IPG and the value displayed, a back telemetry response must be received from the IPG before the screen value changes. Only the parameters that have not been locked out from the clinician's programming station are adjustable. Further, only those channels that have electrodes programmed for stimulation are selectable.

In addition to the channel screens (FIG. 7A), another screen that may be displayed is a feature screen. A representation of a representative feature screen is shown in FIG. 7B. The feature screen may be selected, e.g., by pressing and holding the SEL button 243 for a predetermined time, e.g., two seconds. The feature screen displays the selected program, e.g., by displaying its number, as shown at location 252 in FIG. 7B. In addition to the program number (or other identification of the program), the screen also displays schedule options, e.g., as shown at location 254. These schedule options allow the patient to preset ON and OFF times of the IPG (e.g., turn ON at 6:00 AM and run until 10:00 PM, at which time the IPG automatically turns OFF). Also displayed are the status icons and other informational displays 246, 248 and 250. For example, up to four programs may be stored in the memory of the handheld programmer 202. Programs comprise preset stimulation parameters for the four possible channels, as explained previously. Programs may be named and downloaded from the clinician programmer. Upon selection of a program (1-4), the stimulation parameters in the IPG are gradually adjusted (to prevent jumps or sudden leaps) to a predetermined set of values. The patient may change the parameters from the main screen at any time, but selection of a pre-defined "program" always causes the IPG to revert to the settings defined for that program. If the patient adjusts parameters so that they do not match a stored program, no program name of number is displayed until the patient scrolls to select one.

The patient may also record or overwrite a program from the patient handheld programmer, i.e., without using the clinician programmer 204. In one embodiment, this is done by setting the parameters to their desired value for the new program, and then pressing the up/down buttons 244 and 245 simultaneously (which records the new settings as a new program). The first time the up/down buttons 244 and 245 are pressed simultaneously to record a program (i.e., to record the current settings as a program), the program is assigned as program number 1. The second time the up/down buttons are pressed, the existing settings are stored as program number two, and so on. Thus, the first four programs should be recorded sequentially until all four are written. The parameter values associated with each of the new programs are stored in non-volatile memory within the handheld programmer 202. Thus, in the event the IPG loses data, it may be easily reset to a desired program by turning ON the handheld programmer and selecting the desired program.

Additionally included within the handheld programmer 202 is a hidden physician screen. One representation of such a hidden screen, shown in FIG. 7C, is made available so that medical personnel may use the handheld programmer 202 to set channels and electrodes. Access to the hidden physician screen is made available through a specified coded button combination, e.g., pressing the IPG button 242 and the up/down buttons 244 and 245 simultaneously, followed by pressing a set sequence of the other buttons, e.g., pressing the SEL button 243 once, followed by the pressing the down button 245 twice. Once the hidden physician screen has been activated, not only does the physician's screen appear, but also a telemetered interrogation of the IPG is initiated in order to determine (e.g., through electrode impedance detection) which electrodes are available. The electrodes, which are visibly displayed on the physician's screen at location 254, may be tested. The parameter settings for a selected channel are displayed on the physician's screen at location 256, and the channel number is likewise displayed at location 258. While the physician's screen is activated, the up/down buttons 244 and 245 are used to select individual electrodes for programming, identified on the screen by a highlighting (contrast) change. The associated channel may also be selected. For a highlighted (selected) electrode, the parameters may be adjusted. If the amplitude is set to zero, the electrode is turned OFF. By increasing the amplitude, the electrode is given a cathode polarity, illustrated by a "–" over the highlighted electrode. From zero, if the amplitude is decreased, no numeric value is displayed, but a "+" sign is shown both in the amplitude value location 256 and over the highlighted electrode, indicating a passive anode. Electrode amplitudes should be set at the sense threshold for use in patient screens as channel level 1.

It is thus seen that the patient handheld programmer 202 is small enough to hold comfortably in one hand. It has a flat panel display that shows programmable values as they are selected and/or modified. As desired, it may be inserted into a cover-case which protects the buttons from being inadvertently pressed. It further includes an accessible battery compartment which allows its batteries to be replaced, as needed. The buttons or other controls used on the handheld programmer are easy to manipulate, and provide immediate access (without scrolling and selecting) to ON/OFF, amplitude, pulse width and rate settings. A visual display provided as an integral part of the handheld programmer clearly labels each parameter with the associated control button, and displays large characters for easy viewing. The handheld programmer reliably programs the IPG from a distance of at least 2 feet, and actively displays the status of the communication link with the IPG. Further, when used as a relay device between the clinician's programmer 204 and the IPG 100, the handheld programmer 202 provides a data rate and loop speed that is sufficiently fast so that the patient can make programming selection changes and quickly feel the result. As a safety feature, any given handheld programmer 202 is able to communicate only with one IPG 100 when operated by the patient, whereas a physician may (when the hidden physician screen is activated) use the handheld programmer 202 to communicate universally with any IPG.

Figures 1, 7D:
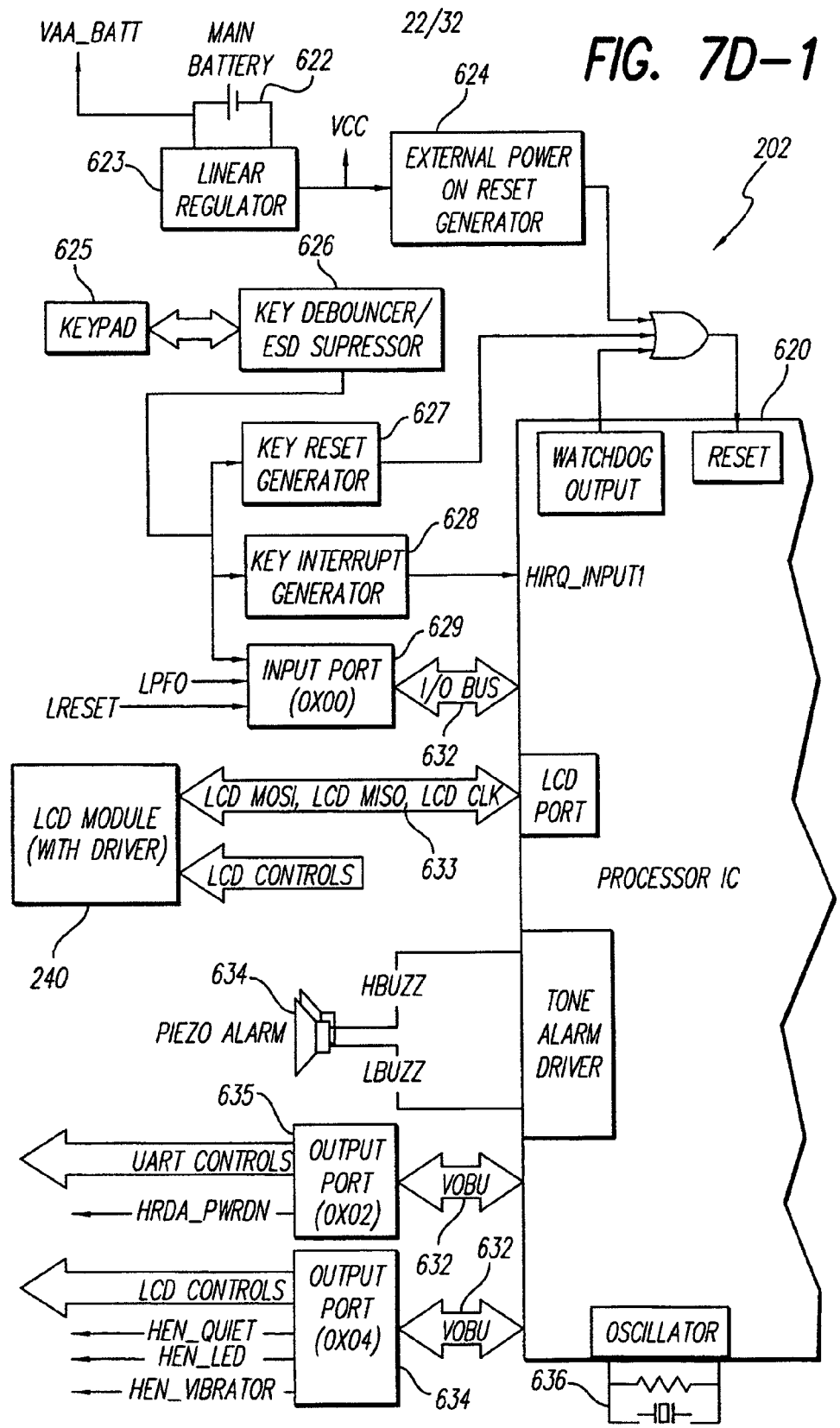
FIG. 7D is a block diagram of a preferred embodiment of the handheld programmer.
Figures 2, 7D:
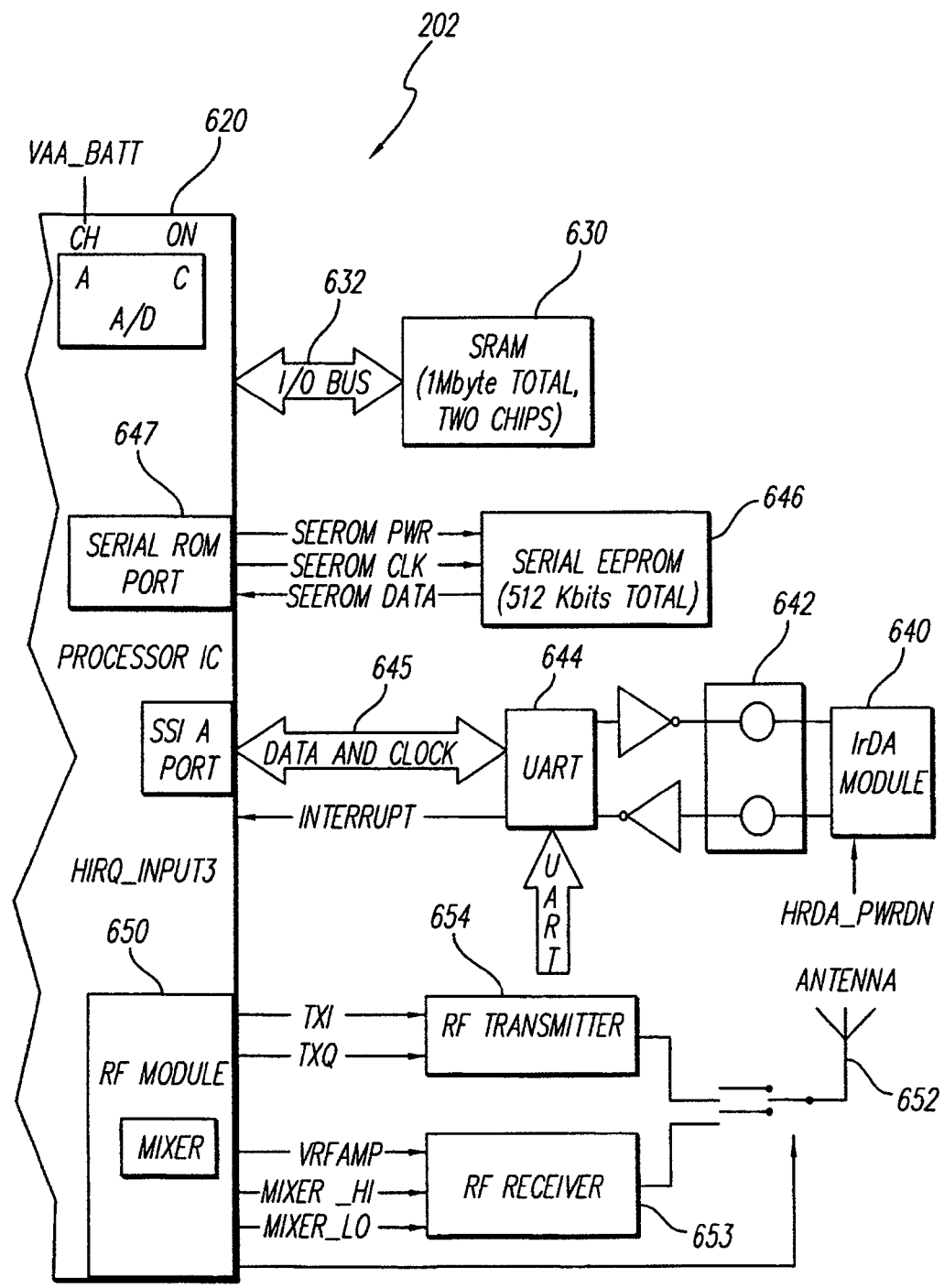

From a circuit point of view, the HHP 202 includes the elements shown in FIG. 7D. Such elements include a microprocessor 620, or processor IC. A main battery 622, e.g., a single AA-sized battery cell providing 3.6 volts dc, provides operating power for the HHP. The voltage from the battery 622 is regulated by a line regulator circuit 623, which line regulator reduces the operating voltage to about 3.3 to 3.0 volts dc. External Power-On Reset circuitry 624 controls the manner in which the HHP is turned ON. A keypad 625, coupled with key debouncer/ESD suppresser circuitry 626, key reset circuitry 627, key interrupt generator circuitry 628, and input port circuitry 629, combine to provide one of the primary ways for manually sending control data to the HHP processor IC 620. The input port circuitry 629, as well as SRAM memory circuitry 630, connect with the processor IC 620 via an I/O bus 632. The LCD screen 240, including appropriate driver circuitry, interfaces directly with the processor IC 620 over a dedicated LCD bus 633. Control commands for the LCD display 240 are sent via the I/O bus 632 through an output port 634 Infrared communications with the HHP 202 occur through an IrDA module 640 connected through a wired serial communications port 642 and a UART circuit 644. The UART circuit 644 is connected to the processor IC 620 via a data and clock bus 645. Control for the UART circuit 644 is obtained via the I/O bus 632 through another output port 635. Another memory circuit 646, e.g., a serial EEPROM circuit, is connected to the processor IC 620 via a serial ROM port 647.

As further seen in FIG. 7D, a crystal 636 is connected to the processor IC and is connected so as to provide the basic oscillator/clock signal used by the processor as it carries out its various functions. In the preferred embodiment, the crystal 636 oscillates at a frequency of about 1.049 MHz. Also, a piezo alarm 634 is connected to the processor IC in order to allow audible alarm tones to be generated.

Additionally, as seen in FIG. 7D, the processor IC 620 includes an RF module 650 that connects to an antenna 652 via an RF Receiver circuit 653 and an RF transmitter circuit 654. It is through this RF module 650 and related circuitry that the HHP 202 sends and receives RF command signals.

RF communication between the HHP 202 and the IPG 100 (FIG. 1) is achieved data words 660 having a signal format as shown in FIG. 7E. A preamble 662 comprises a bit stream that represents either a string of 10's (normal preamble) or a series of 110's (attention preamble). In each case, the least significant bit (LSB) is transmitted first. The attention preamble is a variable length 110110. Timing synchronization is not maintained by either the IPG or the HHP. Hence, the normal method of opening a communication link between the HHP 202 and the IPG 100 is for the HHP to send more than one second of attention preamble bits, followed by a frame sync byte 664, a telemetry ID byte 666, and then the data packet 668. The preamble bits are used to obtain bit synchronization between the transmitter and the receiver. At least eight bits of preamble must be received to ensure bit synchronization.

The frame sync byte 664 follows the preamble bits 662. The frame sync byte, in the preferred embodiment, is "10110000", and is used to obtain byte synchronization between the transmitter and the receiver.

The telemetry ID 666 follows the frame sync byte 664. The telemetry ID comprises a 3 byte value that is used to ensure that only the intended receiver receives the message being sent. A telemetry ID that is all 1s, e.g., "11111111 . . . " indicates a broadcast message that is received by all receivers.

The data packet 668 follows the telemetry ID 666. The data packet 668 comprises an integer number of bytes, and may be formatted in any suitable manner. Command data typically includes amplitude, polarity and pulse width data for each electrode available on the array. Such pulse-defining data may be stored in memory for a plurality of different stimulation programs, in which case the command data may simply comprise a selection of one of the stored programs. Command data may also comprise interrogation data to check the status of various IPG components, such as the battery; or instructions to perform an impedance measurement, as described more fully below.

To ensure the integrity of transmitted data, a code such as a checksum or Cyclical Redundancy Code (CRC) is appended to the data. This code is generated from the data itself. If the generated code does not match the received code, a data error is detected. Some codes contain information that allows the received data to be corrected, thereby avoiding retransmission of the data.

Figure 8:
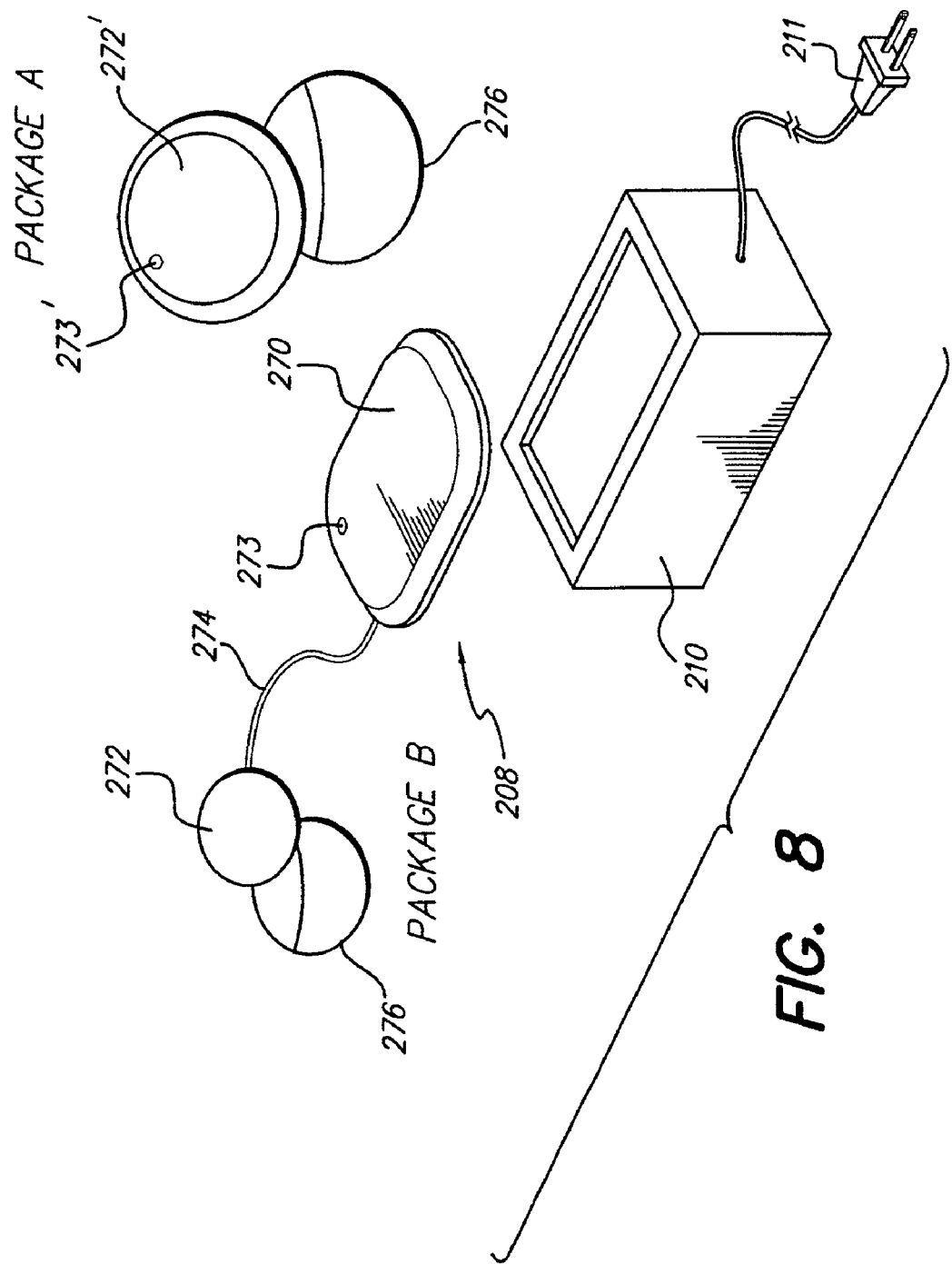
FIG. 8 illustrates two variations of external components of a representative portable charging station (CHR) that may be used with the invention.

Turning next to FIG. 8, the external components of a representative portable charging station (CHR) that may be used with the invention are illustrated. The portable charging station provides a recharging system that is used to transcutaneously recharge the battery of the IPG 100 as needed, via inductive coupling. That is, energy from an external power source is coupled to the battery, or other replenishable power source, within the IPG 100 via electromagnetic coupling. Once power is induced in the charging coil in the IPG, charge control circuitry within the IPG provides the proper charging protocol to charge the Lithium Ion battery. The charger is designed to charge the IPG battery to 80% capacity in two hours, and to 100% in three hours, at implant depths of up to 2.5 cm. When charging is complete, an audible tone is generated by the charger to alert the user to remove the charger. An alignment indicator also provides audible feedback to the user for location the IPG.

As seen in FIG. 8, the charging station includes a two part system comprising a portable charger 208 and a charging base station 210. The charging port 210 is connected to an AC plug 211, and may thus be easily plugged into any standard 110 VAC or 220 VAC outlet. The portable charger 208 includes recharging circuitry housed within a housing 270 that may be detachably inserted into the charging port 210 in order to be recharged. Thus, both the IPG and the portable charger 208 are rechargeable. The housing 270 may be returned to the charging port 210 between uses.

In one embodiment, shown as "Package B" in FIG. 8, a charging head 272 is connected to the recharging circuitry 270 by way of a suitable flexible cable 274. When the IPG battery needs to be recharged, a disposable adhesive pouch 276 or Velcro® strip may be placed on the patient's skin, over the location where the IPG is implanted. The charging head 272 is then simply slid into the pouch, or fastened to the strip, so that it is within 2-3 cm of the IPG. In order for efficient transfer of energy to the IPG, it is important that the head 272 (or more particularly, the coil within the head 272) be properly aligned with the IPG. Thus, in a preferred embodiment, an indicator light 273 placed on the housing 270 provides a visual indication when proper alignment has been achieved. Once aligned, the recharging function is activated. Backtelemetry with the IPG allows the charging process to be monitored. Typically, charging continues until the implant battery has been charged to at least 80% of capacity.

An alternative embodiment of the portable charger 208, shown as "Package A" in FIG. 8, includes the recharging circuitry and battery and charging head housed within a single round package 272'. Such package is less than three inches in diameter and is comfortable to hold against the skin. The adhesive pouch 276 need not necessarily comprise a pouch, but may utilize any suitable means for holding the head (coil) of the charger 208 in proper alignment with the IPG, such as Velcro® strips or patches.

Alternatively, once proper alignment with the IPG has been achieved, as indicated by the visual indicator 273' included on the round package 272', or the indicator 273 included on the package 270, or as otherwise included in the charging station, the charger 208 may simply be taped in place on the patient's skin using removable medical tape.

Figure 9A:
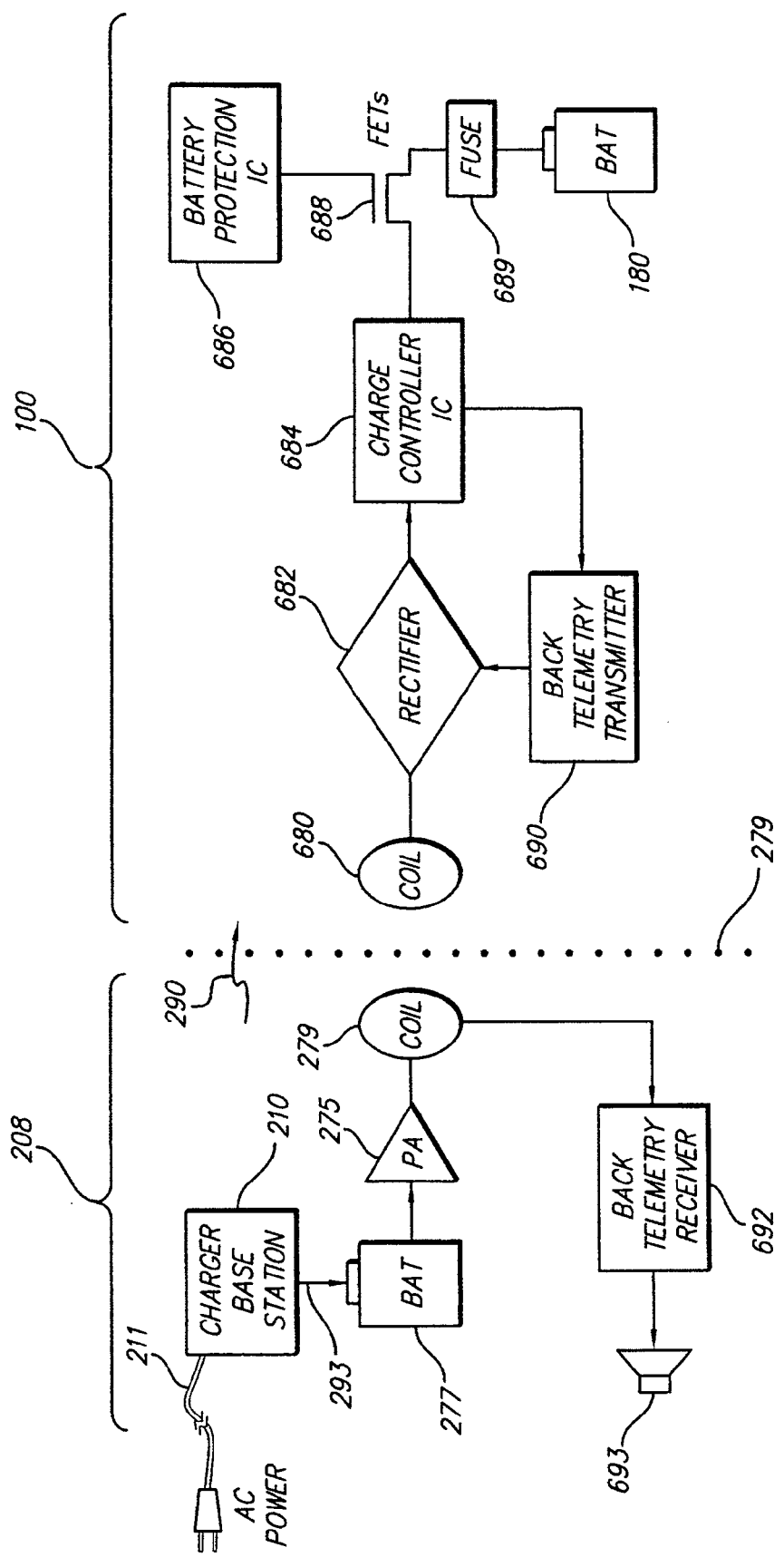
FIG. 9A shows a block diagram of the battery charging system used with the invention.

FIG. 9A illustrates a block diagram of the recharging elements of the invention. As shown in FIG. 9A (and as also evident in FIGS. 4A and 4B), the IPG 100 is implanted under the patient's skin 279. The IPG includes a replenishable power source 180, such as a rechargeable battery. It is this replenishable power source that must be replenished or recharged on a regular basis, or as needed, so that the IPG 100 can carry out its intended function. To that end, the recharging system of the present invention uses the portable external charger 208 to couple energy, represented in FIG. 9A by the wavy arrow 290, into the IPG's power source 180. The portable external charger 208, in turn, obtains the energy 290 that it couples into the power source 180 from its own battery 277.

The battery 277 in the charger 208, in the preferred embodiment, comprises a rechargeable battery, preferably a Lithium Ion battery. (Alternatively, the battery 277 may comprise a replaceable battery.) When a recharge is needed, energy 293 is coupled to the battery 277 via the charging base station 210 in conventional manner. The charging base station 210, in turn, receives the energy it couples to the battery 277 from an AC power line 211. A power amplifier 275, included within the portable charger 208, enables the transfer of energy from the battery 277 to the implant power source 180. Such circuitry 275 essentially comprises DC-to-AC conversion circuitry that converts dc power from the battery 277 to an ac signal that may be inductively coupled through a coil 279 located in the external charging head 272 (or within the round case 272', see FIG. 8) with another coil 680 included within the IPG 100, as is known in the art. Upon receipt of such ac signal within the IPG 100, it is rectified by rectifier circuitry 682 and converted back to a dc signal which is used to replenish the power source 180 of the implant through a charge controller IC 684. A battery protection IC 686 controls a FET switch 688 to make sure the battery 180 is charged at the proper rate, and is not overcharged. A fuse 689 also protects the battery 180 from being charged with too much current. The fuse 689 also protects from an excessive discharge in the event of an external short circuit.

Thus, from FIG. 9A, it is seen that the battery charging system consists of external charger circuitry 208, used on an as-needed basis, and implantable circuitry contained within the IPG 100. In the charger 208, the rechargeable Li-ion battery 277 (recharged through the base station 210) provides a voltage source for the power amplifier 275 to drive the primary coil 279 at a resonant frequency. The secondary coil 680, in the IPG 100, is tuned to the same resonant frequency, and the induced AC voltage is converted to a DC voltage by rectifier circuit 682. In a preferred embodiment, the rectifier circuit 682 comprises a bridge rectifier circuit. The charge controller IC 684 converts the induced power into the proper charge current and voltage for the battery. The battery protection IC 686, with its FET switch 688, is in series with the charge controller 684, and keeps the battery within safe operating limits. Should an overvoltage, undervoltage, or short-circuit condition be detected, the battery 180 is disconnected from the fault. The fuse 689 in series with the battery 180 provides additional overcurrent protection. Charge completion detection is achieved by a back-telemetry transmitter 690, which transmitter modulates the secondary load by changing the full-wave rectifier into a half-wave rectifier/voltage clamp. This modulation is, in turn, sensed in the charger 208 as a change in the coil voltage due to the change in the reflected impedance. When detected, an audible alarm is generated through a back telemetry receiver 692 and speaker 693. Reflected impedance due to secondary loading is also used to indicate charger/IPG alignment, as explained in more detail below in conjunction with the description of FIG. 9B.

In a preferred embodiment, and still with reference to FIG. 9A, the charge coil 680 comprises a 36 turn, single layer, 30 AWG copper air-core coil, and has a typical inductance of 45 µH and a DC resistance of about 1.15 ohms. The coil 680 is tuned for resonance at 80 KHz with a parallel capacitor. The rectifier 682 comprises a full-wave (bridge) rectifier consisting of four Schottky diodes. The charge controller IC 684 comprises an off-the-shelf, linear regulation battery charger IC available from Linear Technology as part number LTC1731-4.1. Such charger is configured to regulate the battery voltage to 4.1 VDC. When the induced DC voltage is greater than 4.1 VDC (plus a 54 mV dropout voltage), the charge controller 684 outputs a fixed constant current of up to 80 mA, followed by a constant voltage of 4.1±0.05 V. If insufficient power is received for charging at the maximum rate of 80 mA, the charge controller 684 reduces the charge current so that charging can continue. Should the battery voltage fall below 2.5 V, the battery is trickled charged at 10 mA. The charge controller 684 is capable of recharging a battery that has been completely discharged to zero volts. When the charge current drops to 10% of the full-scale charge current, or 8 mA, during the constant voltage phase, an output flag is set to signal that charging has completed. This flag is used to gate the oscillator output for modulating the rectifier configuration (full-wave to half-wave), which change in rectifier configuration is sensed by the external charging circuit to indicate charge completion The battery protection IC 686, in the preferred embodiment, comprises an off-the-shelf IC available from Motorola as part number MC33349N-3R1. This IC monitors the voltage and current of the implant battery 180 to ensure safe operation. Should the battery voltage rise above a safe maximum voltage, then the battery protection IC 686 opens the charge-enabling FET switch 688 to prevent further charging. Should the battery voltage drop below a safe minimum voltage, or should the charging current exceed a safe maximum charging current, the battery protection IC 686 prevents further discharge of the battery by turning off the charge-enabling FET switch 688. In addition, as an additional safeguard, the fuse 689 disconnects the battery 180 if the battery charging current exceeds 500 mA for at least one second.

Figure 9B:
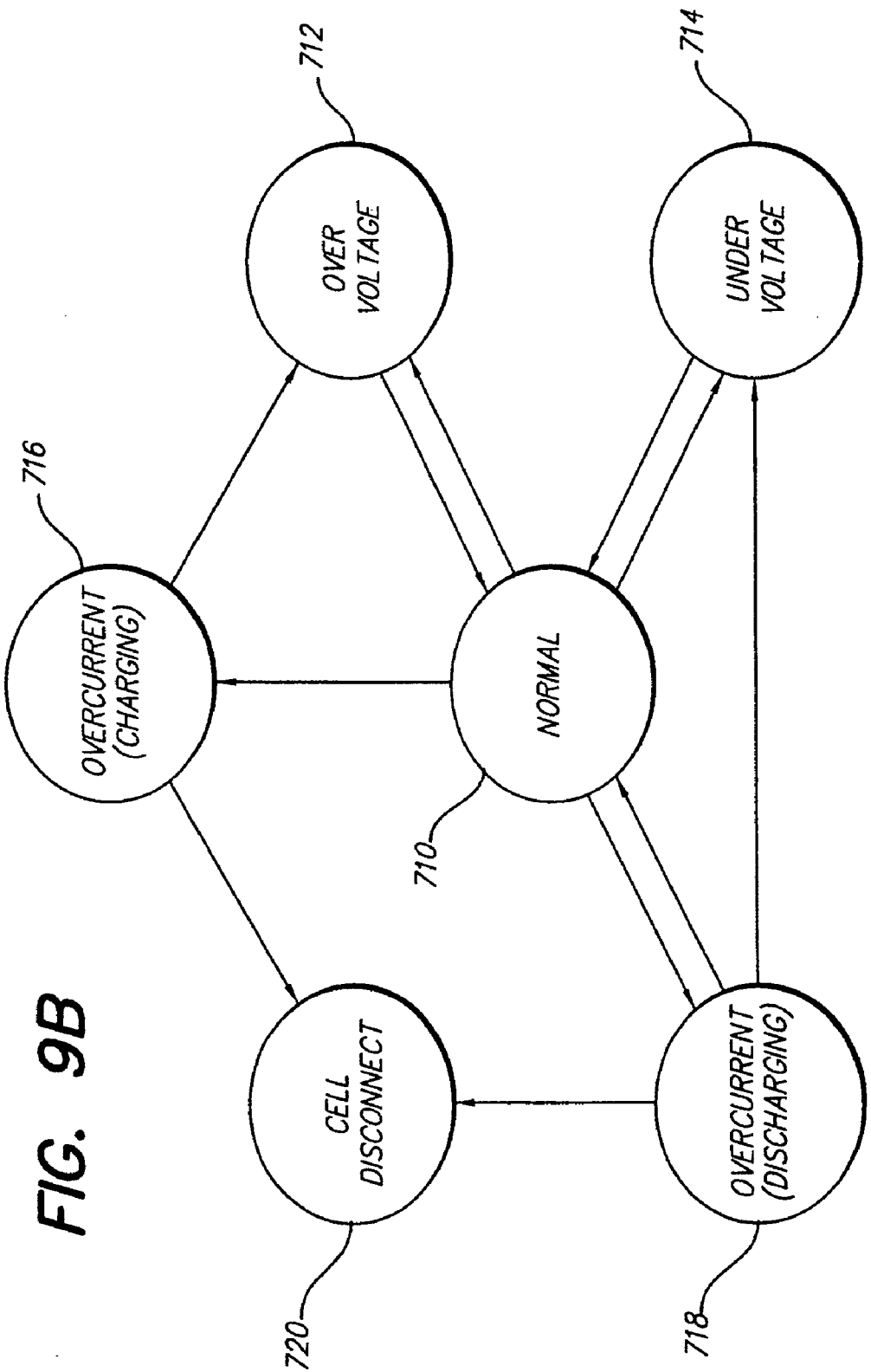
FIG. 9B is a state diagram illustrating the various states that may be assumed by the implant battery charging circuitry during operation of the charging system.

A state diagram that shows the various charging states that may occur relative to the implant battery 180 is shown in FIG. 9B. As seen in FIG. 9B, and assuming a preferred Li-ion battery is used, a normal state 710 reflects that the battery voltage and charging current are within appropriate limits. An over voltage state 712 exists when the battery voltage is greater than 4.25 V and continues until the battery voltage is less than 4.05 V. An undervoltage state 714 exists when the battery voltage is less than 2.5 volts. The undervoltage state 714 continues until the battery voltage is greater than 2.5 volts while charging at a prescribed trickle charge current, e.g., 10 mA. An overcurrent (charging) state 716 exists whenever the charging current exceeds 80 mA. If, while in the overcurrent (charging) state 716, the battery voltage is greater than 4.25 volts, then the over voltage state 712 is entered. If, while in the overcurrent (charging) state 716, the charging current exceeds 500 mA for more than one minute, the fuse 689 opens, and a cell disconnect state 720 is permanently entered. An overcurrent (discharging) state 718 is entered whenever the battery charging current is greater than 100 mA, and continues until the battery charging current is less than 100 mA. If, while in the overcurrent (discharging) state 718, the battery voltage drops below 2.5 volts, then the under voltage state 714 is entered. Also, should the battery current exceed 500 mA for more than one minute while in the overcurrent (discharging) state 718, the fuse 689 opens, and the cell disconnect state 720 is permanently entered.

Figure 9C:
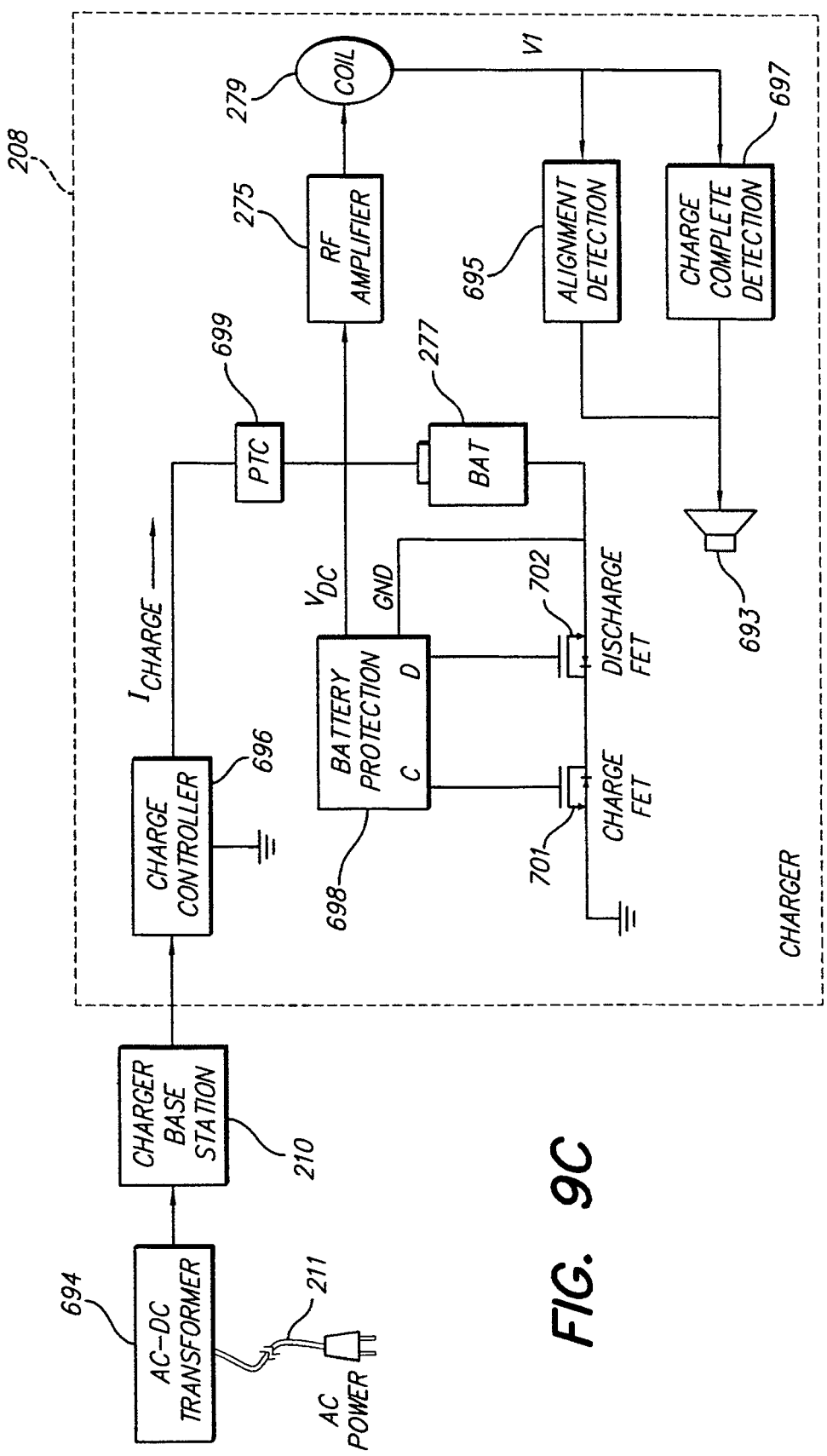
FIG. 9C shows a block diagram of the battery charger/protection circuitry utilized within the external charging station of the invention.

Turning next to FIG. 9C, a block diagram of the circuitry within the external charging station 208 is shown. The charging station comprises a portable, non-invasive transcutaneous energy transmission system designed to fully charge the implant battery in under three hours (80% charge in two hours). Energy for charging the IPG battery 180 initially comes from the main supply line 211, and is converted to 5 VDC by an AC-DC transformer 694, which 5 VDC proves the proper supply voltage for the charger base station 210. When the charger 208 is placed on the charger base station 210, the Li-ion battery 277 in the charger is fully charged in approximately four hours. Once the battery 277 is fully charged, it has enough energy to fully recharge the implant battery 180 (FIG. 9A). If the charger 208 is not used and left on the charger base station 210, the battery 277 will self-discharge at a rate of about 10% per month.

Once the voltage of the battery 277 falls below a first prescribed limit, e.g., 4.1 VDC, during a standby mode, charging of the battery is automatically reinitiated. In addition, should the external charger battery 277 be discharged below a second prescribed limit, e.g., 2.5 VDC, the battery 277 is trickled charged until the voltage is above the second prescribed limit, at which point normal charging resumes.

A battery protection circuit 698 monitors if an over voltage, under voltage, or overcurrent condition occurs, and disconnects the battery, e.g., through opening at least one of the FET switches 701 and/or 702, or from the fault until normal operating conditions exist. Another switch 699, e.g., a thermal fuse, will disconnect the battery should the charging or discharging current exceed a prescribed maximum current for more than a prescribed time, e.g., 1.5 A for more than 10 seconds.

The battery 277 provides a power source for the RF amplifier 275. The RF amplifier, in a preferred embodiment, comprises a class E amplifier configured to drive a large alternating current through the coil 279.

Still with reference to FIG. 9C, an alignment detection circuit 695 detects the presence of the IPG 100 through changes in the reflected impedance on the coil 279. Reflected impedance is a minimum when proper alignment has been obtained. This means that the steady-state voltage V1 sensed at the coil 279 is also at a minimum because maximum coupling occurs. When maximum coupling is detected, e.g., when V1 is at a minimum, an audible or visual alarm may sound. In a preferred embodiment, a first audible tone is generated whenever alignment is not achieved. Thus, as a charging operation begins, the first audible tone sounds, and the user seeks to position the charger 208 (or at least to position the coil 279) at a location that causes the first audible tone to cease. Similarly, a charge complete detection circuit 697 alerts the user through generation of a second audible tone (preferably an ON-OFF beeping sound) when the IPG battery 180 is fully charged. A fully charged condition is also sensed by monitoring the reflected impedance through the coil 279. As indicated above, a fully charged condition is signaled from the IPG by switching the rectifier circuit 682 within the IPG from a full-wave rectifier circuit to a half-wave rectifier circuit. When such rectifier switching occurs, the voltage V1 suddenly increases (e.g., a transient or pulsed component appears in the voltage V1) because the amount of reflected energy suddenly increases. This sudden increase in V1 is detected by the charge complete detection circuit 697, and once detected causes the second audible tone, or tone sequence, to be broadcast via the speaker 693 in order to signal the user that the implant battery 180 is fully charged.

Thus, it is seen that a feature of the SCS system described herein is its use of a rechargeable internal battery and the control system used to monitor its state of charge and control the charging process. The system monitors the amount of energy used by the SCS system and hence the state of charge of the battery. Through bidirectional telemetry (forward and back telemetry) with the hand held programmer 202 and/or the clinician programmer 204, the SCS system is able to inform the patient or clinician of the status of the system, including the state of charge, and further make requests to initiate an external charge process when needed. The acceptance of energy from the external charger is entirely under the control of the SCS implanted system. Advantageously, both physical and software control exist to ensure reliable and safe use of the recharging system.

Figure 10:
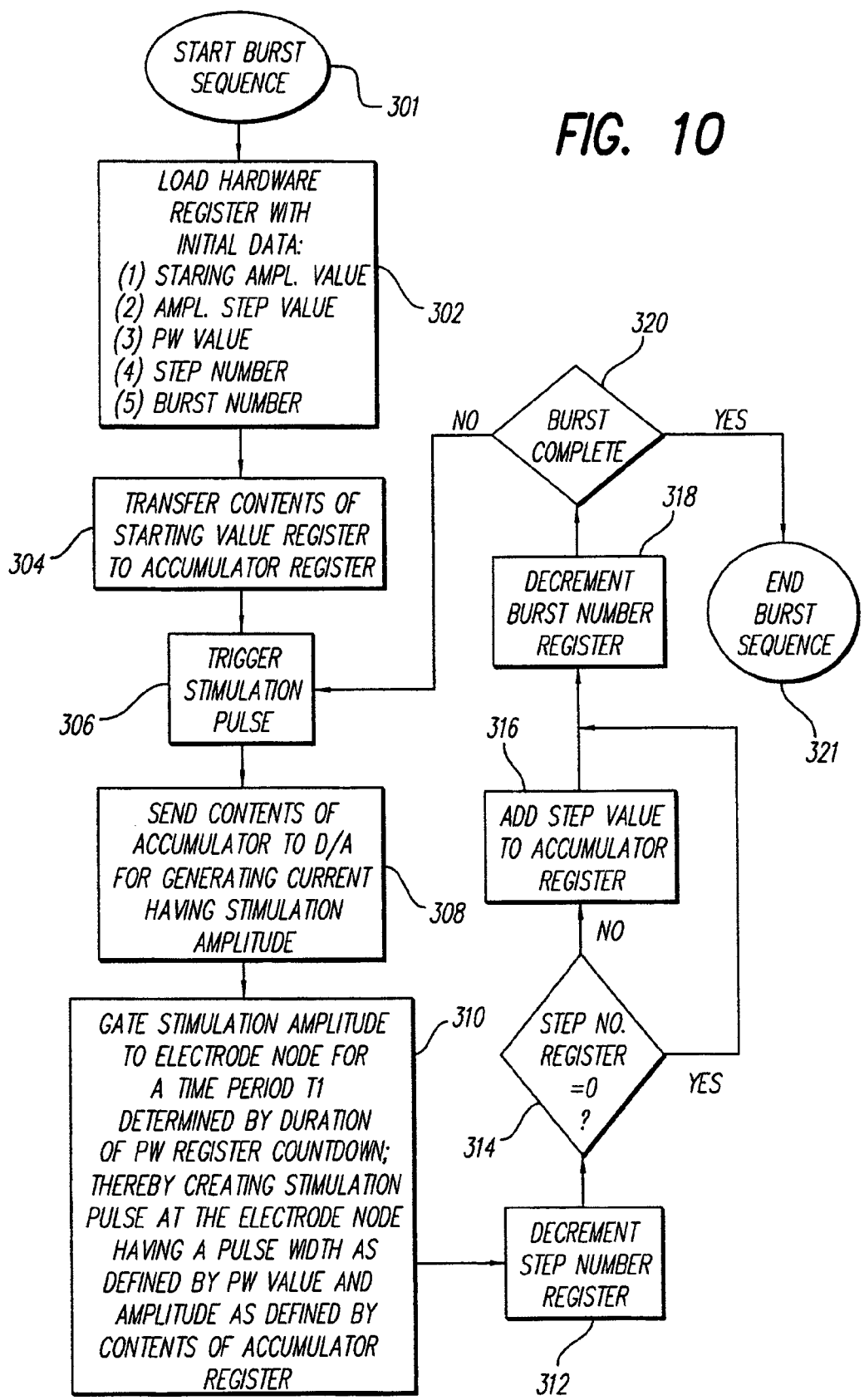
FIG. 10 is a flow diagram illustrating a preferred pulse ramping control technique that may be used with the invention.

Turning next to FIG. 10, a simplified flow chart is shown that illustrates one pulse ramping control technique that may be used with the invention to provide a slow turn-on of the stimulation burst. Such technique is employed because sometimes electrical stimulation may be perceived by the user as having an unpleasant sensation, particularly when a train of stimulations pulses is first started. To overcome this unpleasant sensation, stimulation parameters have traditionally been modulated at the beginning of the pulse train, e.g., by increasing the width of the delivered pulses until the final desired pulse width is achieved. Unfortunately, pulse width (duration) modulation has the undesirable characteristic of applying narrow pulses at the beginning of the stimulation burst; yet such narrow pulses have been found in clinical research to be unpleasant in their own right. The present invention thus avoids ramp modulation of pulse width at the beginning of a stimulation burst, and replaces such modulation with pulse amplitude modulation, maintaining the pulse width as wide as possible, e.g., as wide as the final pulse duration.

The automatic pulse ramping control system that may be used with the present invention modulates pulse amplitude rather than pulse duration and does so with hardware dedicated to that function. Advantageously, there is no need for a controller to monitor and perform the modulation task. At the start of a stimulation burst, a group of dedicated hardware registers hold the amplitude start value, the step size values, and the number of steps to add to the starting amplitude before the stimulation reaches its assigned plateau. The registers are loaded by the controller, with the actual start of the stimulation burst being triggered in conventional manner. The hardware circuitry loads the starting value into an accumulator, and then adds the contents of the step value register to the contents held in the accumulator. The result of this addition is then transferred to a digital-to-analog converter (DAC) circuit which is responsible for actually generating the stimulation pulse (see FIG. 4A or 4C). Another counter keeps track of the programmed pulse duration. Yet another counter may be used to track the number of pulses that have been generated. The duration counter, i.e., the counter responsible for setting the pulse width or pulse duration, gates the D/A converter value to the electrode. The step counter, which is loaded prior to or at the trigger point of the stimulation burst with the number of pulses to be included in the ramp-up sequence, is decremented each time a pulse is generated. For each pulse count thus decremented, the amplitude held in the accumulator register is increased by the step value. When the step counter finally reaches zero, the step value is no longer added to the accumulator, and the accumulator value thereafter remains static, and is used every time the cathodic active phase is required, until the burst stops. When a new burst is triggered again, the amplitude ramp-up process repeats to provide a slow turn-on of the stimulation pulses. The same process is reversed at the end of a burst to avoid unpleasant sensations associated with sudden cessation of stimulation.

One process that may be used to modulate the stimulation pulse amplitude in accordance with the preceding paragraph is illustrated in the flow diagram of FIG. 10. As seen in FIG. 10, when a burst sequence is commenced (block 301), a set of hardware registers is loaded with appropriate initial data (block 302). These hardware registers and the initial data loaded therein include a starting amplitude register, an amplitude step value register, a pulse width value register, a step number register, and a burst number register. The starting amplitude register is loaded with data that defines the starting amplitude of the first pulse in a burst sequence. The amplitude step value register defines how much the amplitude of the stimulation pulse increases as the burst sequence of pulses is ramped up to its final value. The pulse width (PW) register defines a duration of time T1 which sets the programmed pulse width of the current phase of the stimulation pulse. The step number register defines the number of pulses that are included in the ramp-up portion of the stimulation burst. The burst number defines the number of pulses to be included in the stimulation burst. (As one option, when set to a maximum value, the stimulation burst continues indefinitely until the stimulation function is manually turned off.)

Once the initial data is loaded into the hardware registers, the contents of the starting value register are transferred or sent to an accumulator register (block 304). Then, the microcontroller (or other control element), triggers a stimulation pulse (block 306). Such triggering causes the contents of the accumulator register to be sent to the D/A converter(s) responsible for setting the amplitude of the stimulation pulse (block 308). At the same time, the stimulation amplitude defined by the D/A converter(s) is gated to the designated electrode node(s) for the time period T1 set by a countdown (at a known clock rate) of the PW register (block 310). The result is a stimulation pulse having a pulse width as defined by the pulse width register and an amplitude as defined by the contents of the accumulator register. Next, the step number register is decremented (block 312). Then, a check is made to determine is the step number register has decremented to zero (block 314). If NO, then the value of the step value register is added to the accumulator register (block 316) and the process continues (blocks 306, 308, 310, 312, 314) for the next stimulation pulse in the burst sequence. Such next stimulation pulse will have an increased amplitude due to the adding of the step value to the value held in the accumulator register. If the step number register is zero (YES branch of off block 314), then no change is made to the value stored in the accumulator register (block 316 is bypassed) and the amplitude of the stimulation pulses generated thereafter have a constant amplitude as determined by the now static value held in the accumulator register.

After each stimulation pulse is generated, a check is also made to determine the contents of the burst number register (block 318). If the burst is complete (YES branch of block 320), then the burst sequence stops (block 321). Otherwise, the process continues for each pulse in the burst sequence. Note that the burst number register may, in some embodiments, be set to a certain time of day (e.g., 10:00 PM), and the checking of the burst number register (at block 320) may comprise comparing the current time of day (obtained from a suitable real-time clock included as part of the stimulator) with the contents of the burst number register. Alternatively, the burst number register may be loaded with a set number of pulses, e.g., 1000, that are to be included in a burst sequence. After the set number of pulses has been generated, the burst sequence automatically ceases, and no further stimulation pulses or burst sequences are provided until the microcontroller, or other control element indicates that a new burst sequence is to start.

In the manner described above, it is thus seen that the SCS system of the present invention advantageously provides a gradual ramp up, or slow turn-on, of the stimulation pulse amplitude, when first initiated at the commencement of each burst sequence, so as to avoid any unpleasant sensations that might otherwise be perceived by the user, as well as a slow turn-off, or gradual ramp down, at the conclusion of a burst sequence so as to avoid unpleasant sensations associated with sudden cessation of stimulation.

Another important feature of the present invention is the ability of the SCS system to measure the electrode impedance. This is important because implanted electrical stimulation systems depend upon the stability of the devices to be able to convey electrical pulses of known energy to the target tissue to be excited. The target tissue represents a known electrical load into which the electrical energy associated with the stimulation pulse is to be delivered. If the impedance is too high, that suggests the connector and or lead which connects with the electrode may be open or broken. If the impedance is too low, that suggest there may be a short circuit somewhere in the connector/lead system. In either event (too high or too low impedance), the device may be unable to perform its intended function. Hence, the impedance of a connector/lead/electrode interface to the tissue is a general measure of the fitness of the system to perform its required function. The inability of a device to measure such impedance, which unfortunately is the case with many stimulator devices on the market today, means that when changes in the electrode/lead/connector properties occur (as they likely will over time), such changes may go unnoticed until serious deficiencies in the performance of the system are noted. In contrast, the ability to regularly, easily and reliably measure impedance in a consistent manner is critical to the optimal function of such an implanted system.

In order to measure electrode impedance, the present invention has circuitry 194' resident on the analog IC 190' (see FIG. 4B) that is used to measure the voltage at the stimulus outputs. Such measurement circuitry is detailed in FIG. 11A. The architecture for the measurement strategy used by the circuit shown in FIG. 11A revolves around the selection of signals that are transmitted from the circuit side of the electrode coupling capacitor C through a 16-to-1 multiplexor 730 into a buffer amplifier 732. (In FIG. 11A, the current source 734 represents the output current source 4C06 programmed by the NDAC 4C07, assuming monopolar stimulation is applied between one of the sixteen electrodes En and the indifferent electrode 4C11, as shown in FIG. 4C.) The voltage signal to be measured is the difference between the voltage on the circuit side of the coupling capacitor C connected to electrode En when VH is applied with no current flowing (I=0), and when a current of I'=1 mA is flowing through the electrode En having a pulse width of 20 microseconds (µs). Advantageously, the narrow pulse width (20 µs) and low current amplitude (1 mA) reduce the chances of undesirable activation of excitable tissue and unpleasant sensations. The current amplitude during an impedance measurement may be increased or decreased as needed to accommodate impedance measurements over larger or smaller ranges. The 1-to-16 multiplexor 730 allows separate voltage measurements to be made for each electrode En.

Figure 11A:
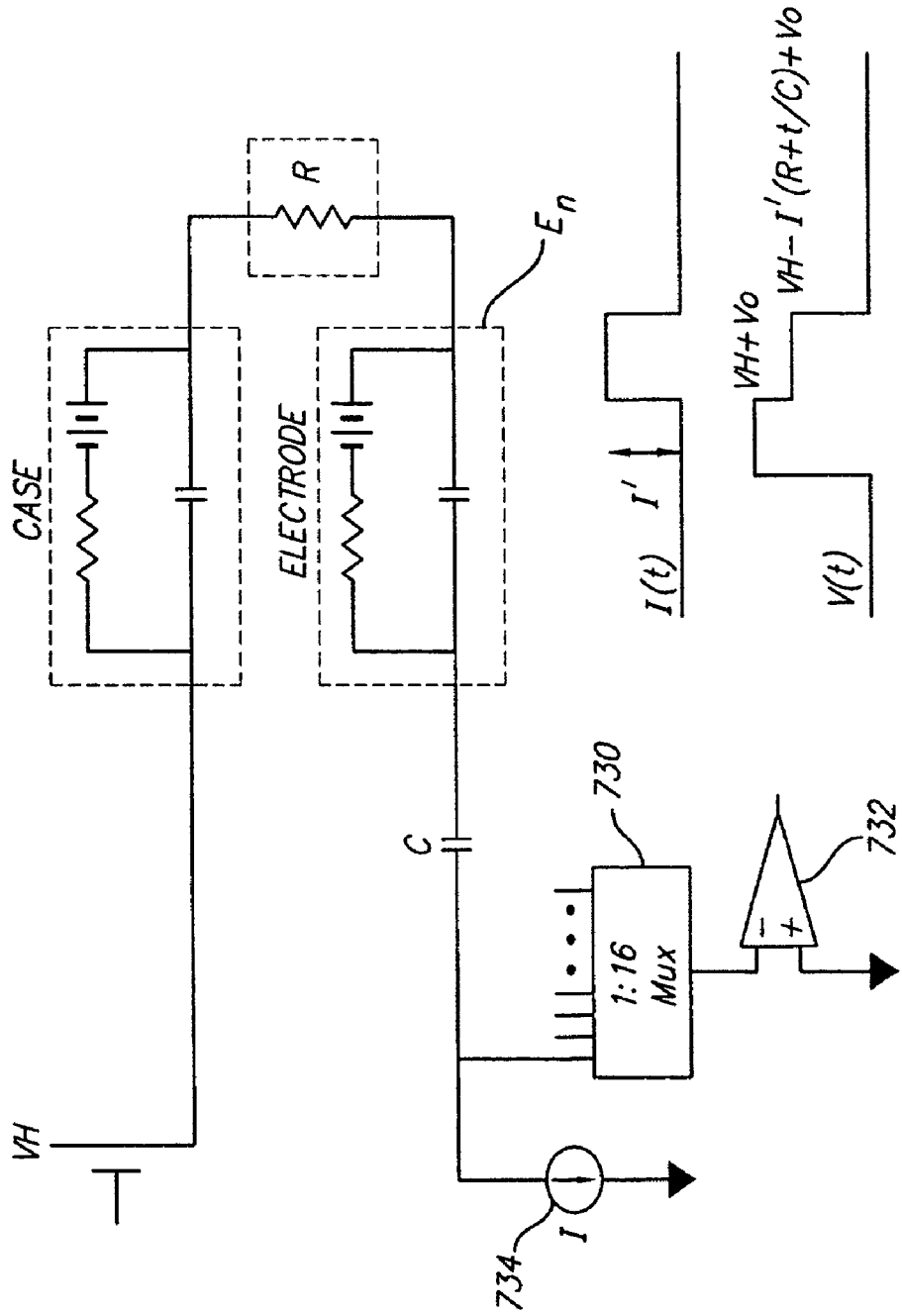
FIG. 11A depicts electronic circuitry used to make an electrode impedance measurement in accordance with the invention.
Figures 1, 11B:
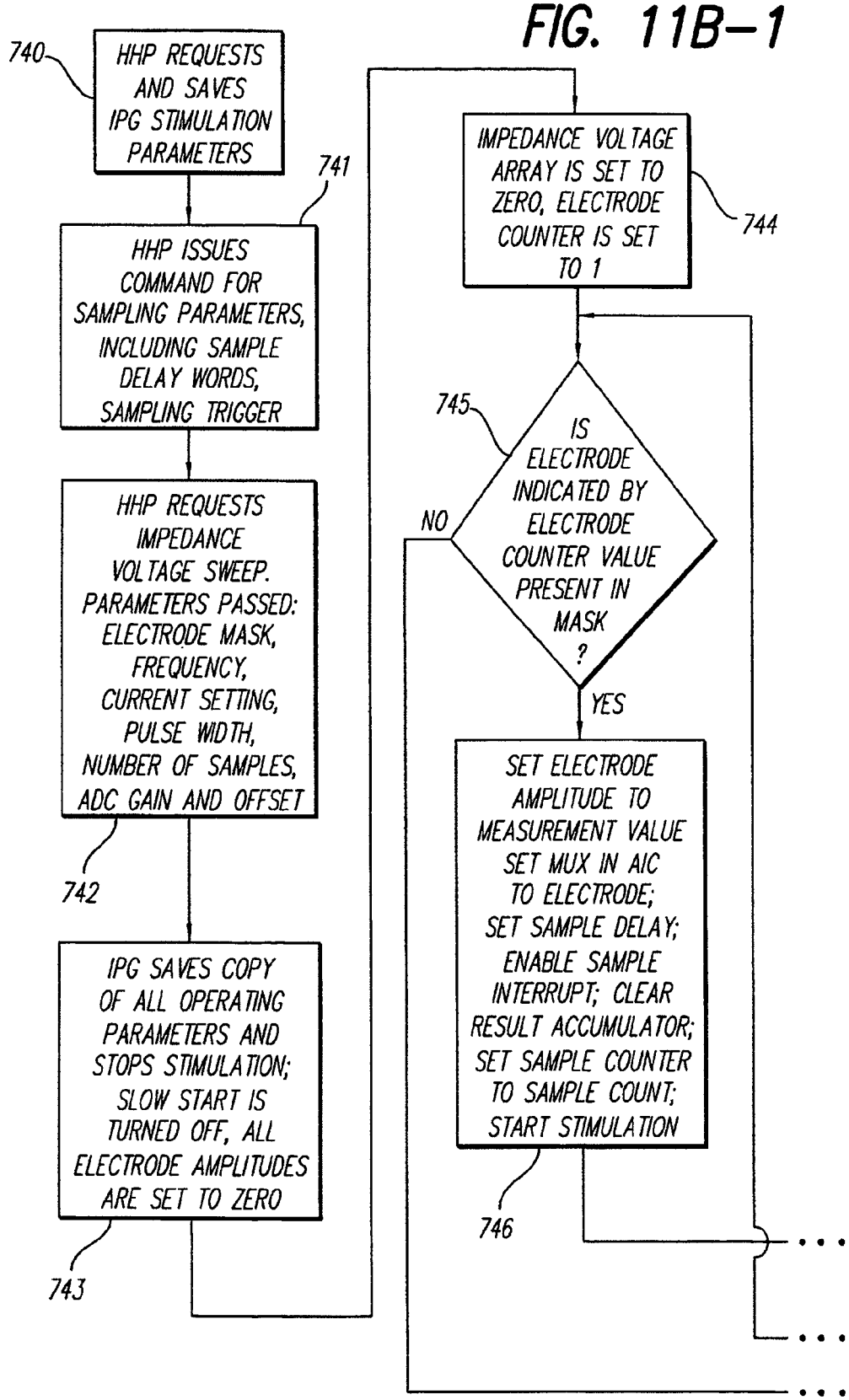
FIG. 11B is a flow diagram that depicts a preferred technique used by the invention to make electrode impedance measurements.

The measurement circuitry within the IPG 100, as depicted in FIG. 11A, thus measures voltages on the internal connection of the electrode coupling capacitors. Using sampling circuitry contained within the analog IC 190', the voltage on these points for each electrode may be selectively captured in a sample and hold circuit and then converted by the analog to digital converter (ADC) circuit 734 within the processor 160' to a digital value. This digital value may then be sent to the HHP 202 when a communication link is established, and the processor within the HHP may then compute the impedance from these measurements.

Advantageously, because the voltage measurement performed using the circuitry shown in FIG. 11A is of general utility to the HHP, as well as the Clinician's Programming System, several commands may be used to perform various functions of voltage measurement and impedance calculation. Such functions include: (1) read the voltage on a single designated electrode; (2) read the voltage on up to 16 electrodes (defined by an electrode mask value); (3) program sampling parameters; (4) perform an impedance voltage sweep on all electrodes in the mask; and (5) report voltage array values.

The most common of the above functions that is performed is the impedance voltage sweep on all the electrodes indicated by a mask value. (A "mask value" is just a way of defining which electrodes are available for use with a given patient, inasmuch as not all patients will have all sixteen electrodes available for their use.) The method of making such an impedance voltage sweep measurement is illustrated in the flow diagram of FIG. 11 B.

Figures 2, 11B:
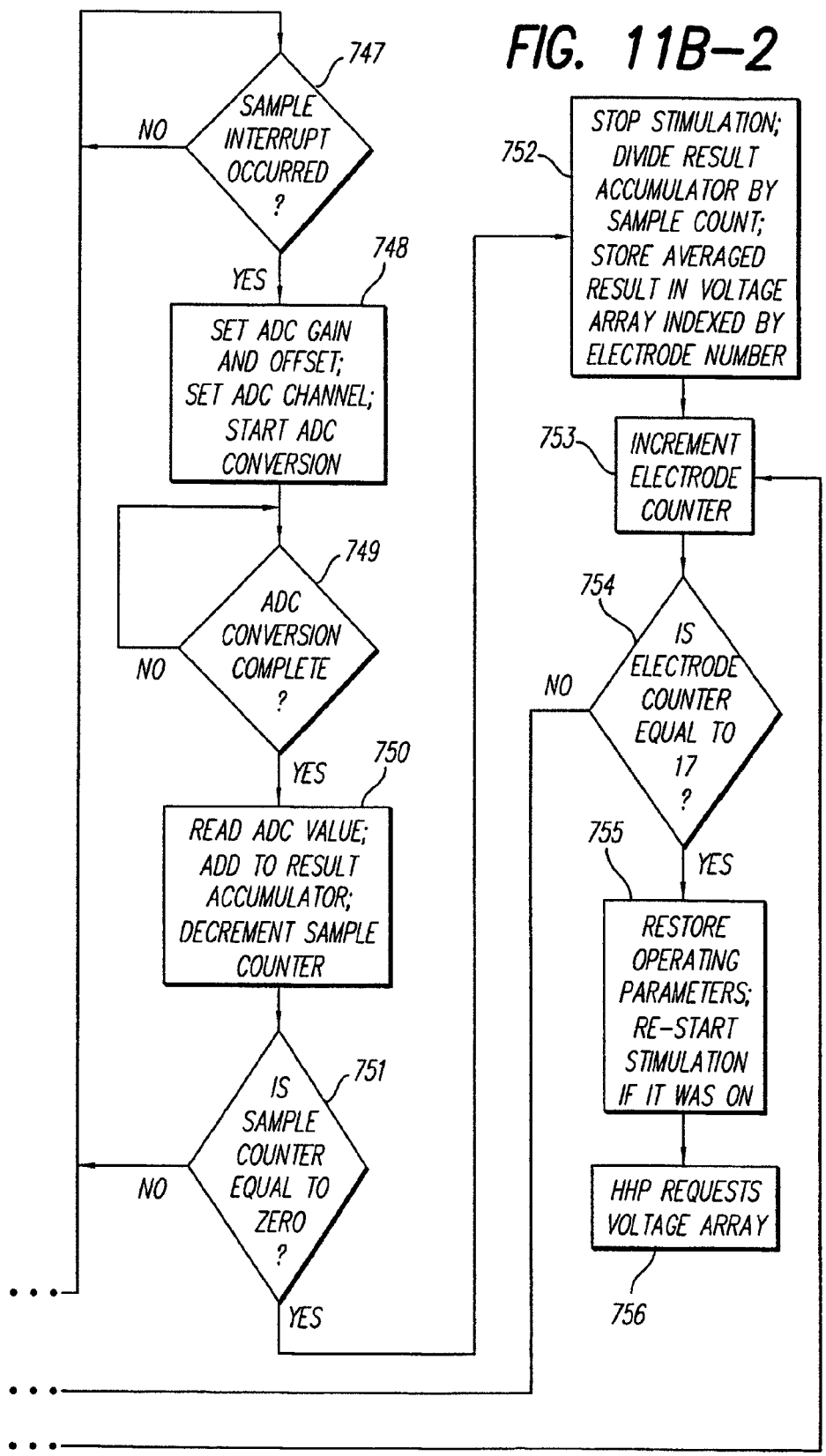

As seen in FIG. 11 B, a first step in the impedance voltage sweep measurements is for the HHP to request and save the IPG stimulation parameters (block 740). Next, the HHP issues a command for sampling parameters, including the sample delay words, and sampling trigger (block 741). Then, the HHP requests that an Impedance Voltage Sweep be performed (block 742), which typically includes sending at least the following parameters to the IPG: electrode mask, frequency, current setting, pulse width, number of samples, and ADC gain and offset. When received by the IPG, the IPG saves a copy of all operating parameters and stops stimulation (block 743). Additionally, slow (or soft) start is turned off, and all electrode amplitudes are set to zero. Then, the impedance voltage array (the location where the measurements are to be stored within the IPG) is set to zero, and an electrode counter is set to one (block 744).

Next, a decision is made as to whether the electrode indicated by the electrode counter value is present in the mask (block 745). If YES, then the amplitude of the stimulus current for the electrode indicated by the electrode counter is set to the measurement amplitude (block 746), e.g., 1 mA, and other parameters are appropriately set. That is, the MUX 730 in the analog IC 190' is set for the electrode being measured, the sample delay is set, the sample interrupt is enabled, the result accumulator is cleared, and a sample counter is set to the sample count. Then, the stimulus current is generated. If NO, then the electrode counter is incremented (block 753); and, unless the electrode count equals 17 (block 754), the process repeats. That is, a decision is made as to whether the electrode indicated by the electrode counter value, which has now been incremented, is present in the mask (block 745).

After generation of the stimulus current (block 746), the system waits for the occurrence of a sample interrupt (block 747). When the sample interrupt occurs, the ADC gain and offset are set, the ADC channel is set, and the ADC conversion process is initiated (block 748). When the ADC conversion process is complete (block 749), the ADC value is read and added to the result accumulator, and the sample counter is decremented (block 750). If the sample counter is not equal to zero (block 751), then the sampling process (blocks 747-750) repeats until all of the samples specified for the measurement have been taken. Once all of the samples have been taken, the stimulation is stopped, and the value in the result accumulator is divided by the sample count in order to provide an average value of the measurements. The averaged result is then stored in the voltage array and indexed by the electrode number (block 752).

After the averaged result has been stored, the electrode counter is incremented (block 753). If the value in the electrode counter is less than seventeen (block 754), then the process repeats for other electrodes (blocks 745-753) until all of the electrodes in the mask have been measured. When all electrodes have been measured, the operating parameters are restored and stimulation is restarted, if it was on (block 755). Then, when a link is established with the HHP, the averaged results in the voltage array are sent to the HHP (block 756). The HHP then uses these values to compute impedance, or for other purposes.

An alternate method that may be used to measure electrode impedance in accordance with the present invention is to automatically sample the voltage applied across a stimulating electrode node and corresponding reference electrode (i.e., across an electrode pair) using a pair of counters, a control register, a sample and hold circuit, an analog-to-digital (A/D) converter, and a result register. In operation, the two counters are loaded with values corresponding to the cathodic pulse duration and ½ that duration. The control register synchronizes the operation of the two counters, and when the ½-duration counter counts down to zero, the control register causes the sample and hold circuit to measure or sample the electrode voltage, after which the A/D converter is instructed to convert the sampled voltage to a digital value which is stored in a result register. A controlling processor, e.g., the microcontroller 160 or 160' in the IPG (FIG. 4A or 4B), may then determine the apparent impedance of the electrode by knowing the voltage measured and the amount of current generated for the pulse. Alternatively, the impedance computation may take place in the HHP using the processor within the HHP 202. In this manner, changes in the electrode tissue properties, as well as failures in leads, connectors, and electrodes, may readily be recognized by the controlling system.

One technique that may be used to achieve the impedance measuring method described in the previous paragraph is depicted in the flow diagram of FIG. 11C. As seen in FIG. 11C, once the impedance measuring method has been started, a current pulse of a known amplitude and width is generated (block 332). This pulse is applied to the electrode pair whose impedance is to be measured. The value of the pulse width is loaded into a first register (also block 332). One half (½) of the value of the first register is then loaded into a second register (block 334). Both the first and second registers are then counted down under synchronous control (block 336). This count down continues until the contents of the second register are zero (block 338). This represents roughly the mid-point of the stimulation pulse that has been generated, and represents a sample time when transients and spikes that might otherwise be present in the measured voltage have settled down. At this mid-point value, or sample time, the voltage across the electrode node(s) of the electrode pair is sampled and measured (block 340). The sampled voltage value is held in a sample and hold circuit (block 342). From the sample and hold circuit, the sampled and measured voltage value is passed on to an A/D converter, where the voltage measurement is digitized (block 344), and held in a result register (block 346). The value of the current applied to the electrode while making the voltage measurement is retrieved (block 348). A suitable processor, e.g., the microcontroller 160, is then used to compute the impedance as the ratio of the sampled voltage over the known current (block 349). This impedance may then be stored and/or otherwise processed so that any significant changes in impedance can be immediately noted and communicated (e.g., through back telemetry) to the external programming devices (hand held programmer 202 and/or clinician programmer 204) used by the user or clinician.

While the invention herein disclosed has been described by means of specific embodiments and applications thereof, numerous modifications and variations could be made thereto by those skilled in the art without departing from the scope of the invention set forth in the claims.

What is claimed is:

1. An implantable stimulator device, comprising:
   a plurality of electrode nodes implantable adjacent to tissue to be stimulated;
   programmable current source circuitry configured for sourcing a first one or more output currents respectively to a first one or more of the plurality of electrode nodes, wherein the current source circuitry comprises a plurality of adjustable positive current sources;
   programmable current sink circuitry configured for sinking a second one or more output currents respectively from a second one or more of the plurality of electrode nodes, wherein the current sink circuitry comprises a plurality of adjustable negative current sources;
   a programmable switch matrix;
   control circuitry configured for programming the current source circuitry and the current sink circuitry, such that the a total sum of the first one or more output currents equals a total sum of the second one or more output currents in each of one or more channels, and further configured for programming the switch matrix to selectively couple one or more of the positive current sources respectively to the first one or more of the electrode nodes, and for programming the switch matrix to selectively couple one or more of the negative current sources respectively to the second one or more of the electrode nodes.

2. The implantable stimulator device of claim 1, wherein one of the positive current sources and one of the negative current sources are coupled to one of the electrode nodes via a common node.

3. The implantable stimulator device of claim 1, wherein the adjustable positive current sources are PDACs, and the adjustable negative current sources are NDACs.

4. The implantable stimulator device of claim 1, wherein the first one or more output currents comprises a first plurality of output currents, the first one or more electrode nodes comprises a first plurality of electrodes nodes, the second one or more output currents comprises a second plurality of output currents, and the second one or more electrode nodes comprises a second plurality of electrodes nodes.

5. The implantable stimulator device of claim 1, wherein the one or more channels comprises a plurality of channels.

6. The implantable stimulator device of claim 1, wherein the first one or more output currents and the second one or more output currents are pulsed.

7. The implantable stimulator device of claim 1, wherein the control circuitry comprises a microcontroller.

8. The implantable stimulator device of claim 1, further comprising one or more stimulation electrode leads coupled to the electrode nodes.

9. The implantable stimulator device of claim 1, wherein the control circuitry is configured for storing stimulation parameters with which the control circuitry is configured for programming the current source circuitry and the current sink circuitry.

10. The implantable stimulator device of claim 9, wherein the control circuitry is configured for being telemetrically programmed with the stimulation parameters.

11. The implantable stimulator device of claim 1, further comprising a case coupled to one of the electrode nodes.

12. A method of treating a patient, comprising:
    implanting the implantable stimulator device of claim 1 into a patient; and
    respectively coupling a plurality of electrodes to the electrode nodes.

13. The method of claim 12, further comprising stimulating neural tissue of the patient with the first one or more output currents.

14. The method of claim 13, wherein the neural tissue is spinal cord tissue.

* * * * *